US008273955B2

(12) United States Patent
Tirichine et al.

(10) Patent No.: US 8,273,955 B2
(45) Date of Patent: Sep. 25, 2012

(54) SPONTANEOUS NODULATION IN PLANTS

(75) Inventors: Leila Tirichine, Levallois-Perret (FR); Jens Stougaard Jensen, Aarhus C (DK); Niels Sandal, Tilst (DK); Lene Heegaard Madsen, Risskov (DK)

(73) Assignee: Aarhus Universitet, Arhus C (DK)

( * ) Notice: Subject to any disclaimer, the term of this patent is extended or adjusted under 35 U.S.C. 154(b) by 909 days.

(21) Appl. No.: 11/995,422

(22) PCT Filed: Jul. 13, 2006

(86) PCT No.: PCT/DK2006/050029
§ 371 (c)(1),
(2), (4) Date: Sep. 29, 2008

(87) PCT Pub. No.: WO2007/006318
PCT Pub. Date: Jan. 18, 2007

(65) Prior Publication Data
US 2011/0078814 A1    Mar. 31, 2011

Related U.S. Application Data

(60) Provisional application No. 60/699,209, filed on Jul. 14, 2005.

(51) Int. Cl.
*A01H 5/00* (2006.01)
*A01H 5/10* (2006.01)
*A01H 1/06* (2006.01)
*A01H 1/02* (2006.01)
*C12N 15/82* (2006.01)

(52) U.S. Cl. ......... 800/298; 800/278; 800/295; 800/320
(58) Field of Classification Search .................. None
See application file for complete search history.

(56) References Cited

FOREIGN PATENT DOCUMENTS

| EP | 1555321 | 7/2005 |
|---|---|---|
| WO | WO 97/35968 | 10/1997 |
| WO | WO 02/102841 A2 | 12/2002 |

OTHER PUBLICATIONS

Patil et al. (PNAS, 92:4897-4901; Published 1995).*
Gleason et al. (Nature, 441:1149-1152, 2006).*
Sathyanarayanan et al. (J. Biol. Chem., 276:32940-32947, Published 2001).*
Communication issued in EP Application No. 06761874, dated Oct. 19, 2010, 4 pages.
Response to Communication issued in EP Application No. 06761874 on Oct. 19, 2010, filed Dec. 15, 2010.
Communication issued in EP Application No. 06761874, dated Jun. 25, 2009, 4 pages.
Response to Communication issued in EP Application No. 06761874 on Jun. 25, 2009, filed Dec. 18, 2009.
Communication issued in EP Application No. 06761874, dated May 29, 2008, 5 pages.
Response to Communication issued in EP Application 06761874 on May 29, 2008, filed Aug. 11, 2008.
Mitra Raka M. et al., "A Ca2+/calmodulin-dependent protein kinase required for symbiotic nodule development: Gene identification by transcript-based cloning" Proceedings of the National Academy of Sciences of the United States of America, vol. 101, No. 13, Mar. 30, 2004, pp. 4701-4705.
Tirichine Leila et al., "Deregulation of Ca2+/calmodulin-dependent kinase leads to spontaneous nodule development" Nature (London), vol. 441, No. 7097, Jun. 2006, pp. 1153-1156.
Szczyglowski, K. et al., Lotus genome: pod of gold for legume research, Trends Plant Sci. Oct. 13, 2008(10): 515-7.
"Putative calcium/calmodulin-dependent protein kinase", Sep. 13, 2004, retrieved from EBI accession No. UNIPROT:Q6AVM3.
Sathyanarayana, P.V. et al. "Calcium-stimulated Autophosphorylation Site of Plant Chimeric Calcium/Calmodulin-dependent Protein Kinase." The Journal of Biological Chemistry. vol. 276. No. 35, (2001) pp. 32940-29427.
Sathyanarayana, P.V. et al. "Autophosphorylation-dependent inactivation of plant chimeric calcium/calmodulin-dependent protein kinase." Euopean Journal of Biochemistry, vol. 269 No. 10, (2002) pp. 2457-2463.
Patil, Shameekumar et al. "Chimeric plant calcium/calmodulin-dependent protein kinase gene with a neural visinin-like calcium-binding domain." Proceedings fo the National Academy of Sciences of the United States of America. vol. 92 No. 11 (1995) pp. 4897-4901.
Takezawa D. et al. "Dual Regulation of a chimeric plant serine/threonine kinase by calcium and calcium/calmodulin." Journal of Biological Chemistry. vol. 271 No. 14 (1996) pp. 8126-8132.
Pichon M. et al. "ENOD12 gene expression as a molecular marker for comparing Rhizobium-dependent and—independent nodulation in alfalfa" Molecular Plant-Microbe Interactions. vol. 7 No. 6 (1994) pp. 740-747.
Jimenez-Zurdo, Jose et al. "Expression profiles of 22 novel molecular markers for organogenetic pathways acting in alfalfa nodule development" Molecular Plant-Microbe Interactions vol. 13 No. 1 (2000) pp. 96-106.

(Continued)

*Primary Examiner* — Vinod Kumar
(74) *Attorney, Agent, or Firm* — Faegre Baker Daniels LLP

(57) ABSTRACT

Formation of nitrogen fixing root nodules in legumes is induced by perception of lipochitin-oligosaccharide signal molecules secreted by compatible *Rhizobium* bacteria, which triggers a common symbiotic pathway. The present invention provides a spontaneous nodule formation (snf1-5g) mutant, in which the formation of symbiotic nodules is deregulated, leading to nodule development in the absence as well as in the presence of *Rhizobium* bacteria and/or exogenous rhizobial signals. The invention further provides an isolated DNA sequence encoding a mutant chimeric $Ca^{2+}$/calmodulin dependent protein kinase whose activity results in this `gain of function' phenotype of spontaneous nodule formation. Furthermore the snf1-5g gene is shown to confer a spontaneous nodule formation phenotype to plants having a nodulation deficient genetic background. A gene of the invention, that confers a spontaneous nodulation phenotype, has utility for the transfer and establishment of nitrogen fixing capability in non-nodulating plants, and thereby reducing the nitrogen fertilizer dependence of non-nodulating crop plants.

30 Claims, 8 Drawing Sheets

OTHER PUBLICATIONS

Levy, Julien et al. "A putative Ca2+ and calmodulin-dependent protein kinase required for bacterial and fungal symbioses." Science (Washington D.C.) vol. 303 No. 5662 (2004) pp. 1361-1364.

Godfroy, Olivier et al. "A Rice Calcium- and Calmodulin- Dependent Protein Kinase Restores Nodulation to a Legume Mutant." MPMI vol. 19 No. 5 (2006) pp. 495-501.

Oldroyd, Giles E.D. et al. "Calcium, Kinases and Nodulation Signalling in Legumes." Nature Reviews: Molecular Cell Biology. vol. 5. (2004) pp. 566-576.

Geurts, Rene, et al. "Nod factor signaling genes and their function in the early stages of *Rhizobium* infection." Current Opinion in Plant Biology 2005.

Pawlowski, Katharina et al. "Rhizobial and Actinorhizal Symbioses: What Are the Shared Features?" The Plant Cell, vol. 8 (1996) pp. 1899-1913.

Hiei, Yukoh et al. "Efficient transformation of rice (*Oryza sativa* L.) mediated by Agrobacterium and sequence analysis of the boundaries of the T-DNA." The Plant Journal vol. 6 Issue 2 (1994) pp. 271-282.

Perry, Jillian A. et al. "A TILLING Reverse Genetics Tool and a Web-Accessible Collection of Mutants of the Legume *Lotus japonicus*" Plant Physiology vol. 131 (2003) pp. 866-871.

Handberg, Kurt et al. "Lotus japnicus, an autogamous, diploid legume species for classical and molecular genetics" The Plant Journal vol. 2. Issue 4 (1992) pp. 487-496.

Broughton, W.J. et al. "Control of Leghaemoglobin Synthesis in Snake Beans." Biochemistry Journal. vol. 125 (1971) pp. 1075-1080.

Jiang, Qunyi, et al. "Classical and Molecular Genetics for the Model Legume *Lotus japonicus*" MPMI. vol. 10. No. 1. (1997) pp. 59-68.

Vincent, JM. "A Manual for the Practical Study of Root-Nodule Bacteria" Published for International Biological Programme by Blackwell Scientific Publications.

Wopereis, Judith, "Short root mutant of *Lotus japonicus* with a dramatically altered symbiotic phenotype." The Plant Journal vol. 23 Issue 1 (2000) pp. 97-114.

Wegel, Eva. "Mycorrhiza Mutants of *Lotus japnicus* Define Genetically Independent Steps During Symbiotic Infection." MPMI vol. 11 No. 9 (1998) pp. 933-936.

Vierheilig, Horst, et al. "Ink and Vinegar, a Simple Staining Technique for Arbuscular-Mycorrhizal Fungi." Applied and Environmental Microbiology. (Dec. 1998) pp. 5004-5007.

Levy, Julien, et al. A Putative $Ca^{2+}$ $^{and}$ Calmodulin-Dependent Protein Kinase Required for Bacterial and Fungal Symbioses. Science vol. 303 (2004) pp. 1361-1365.

Stougaard, Jens, et al. "*Agrobacterium rhizogens* as a Vestor for Transforming Higher Plants." Methods in Molecular Biology. vol. 49.

Turner, G.L., et al. Measurement of Nitrogen Fixation by Indirect Means. Methods for Evaluating Biological Nitrogen Fixation. Edited by F.J. Bergersen. (1980) John Wiley & Sons Ltd.

* cited by examiner

SPONTANEOUS NODULATION IN PLANTS

SEQUENCE LISTING

The sequence listing, submitted electronically on Mar. 5, 2009 and entitled "83196-375888_Sequence_Listing.txt," with a creation date of Mar. 5, 2009, and a size of 158 KB, is hereby incorporated by reference in its entirety.

BACKGROUND OF THE INVENTION

The growth of agricultural crops is generally limited by the availability of nitrogen, and at least 50% of global requirement is met by the application of synthetic fertilisers in the form of ammonia, nitrate or urea. However, there is a growing need to exploit one of the most important natural sources of nitrogen for agriculture, namely biological nitrogen fixation.

The primary source of biological nitrogen fixation are *Rhizobium* or *Rhizobia* spp and the actinobacterium *Frankia* spp, which are a small group of prokaryotes that produce nitrogenases, and form endosymbiotic associations with plants conferring the ability to fix nitrogen. Although many plants can associate with nitrogen-fixing bacteria, only a few plants, all members of the Rosid I Clade, form endosymbiotic associations with *Rhizobia* spp and *Frankia* spp., which are unique in that most of the nitrogen is transferred to and assimilated by the host plant. The Leguminosae plant family, which includes soybean, bean, pea, peanut, chickpea, cowpea, lentil, pigeonpea, alfalfa and clover, are the most agronomically important members of this small group of nitrogen-fixing plants. Biological nitrogen fixation via the endosymbiotic association reduces the need for expensive nitrogen fertilizers in legume crops and is an important feature of sustainable agriculture. Legumes can also utilize nitrogen available in the soil, such that when levels of soil nitrate are high, nodule formation is suppressed and the plant shifts from nitrogen metabolism to growth on nitrate (Wopereis et al., 2000).

*Rhizobium*-legume symbiosis involves the interaction of a set of plant and bacterial genes in a complex process leading to the initiation and development of root nodules. Organogenesis of nodules is triggered by the rhizobial microsymbiont, but the legume host plant encodes the developmental program responsible for building the nodule tissues and for regulating the process. Lipo-chitin-oligosaccharides (Nod-factors) synthesized and secreted by *Rhizobia* are major signal molecules that trigger this process. The major Nod-factor secreted by the *Mesorhizobium loti* microsymbiont of *Lotus* is a pentameric N-acetylglucosamine carrying a cis-vaccenic acid and a carbamoyl group at the non-reducing terminal residue together with a 4-O-acetylfucose at the reducing terminal residue. Perception of Nod-factor in *Lotus* is mediated by NFR1 and NFR5 receptor kinases (Radutoiu et al., 2003 Nature 425: 585-592; Madsen et al., 2003 Nature 425: 637-640), that together with an LRR receptor-kinase gene, SymRK, communicate with a common signal transduction pathway, shared with mycorrhizal symbiosis (Oldroyd and Downie, 2004 *Mol. Cell Biology* 5: 566-576). This common pathway is encoded by seven genes, SymRK, Castor, Pollux, Nup133, Sym15, Sym6 and Sym24. Analysis of mutants has shown that NFR1/NFR5 receptor(s), SymRK encoded LRR protein kinase, CASTOR/POLLUX cation channel(s) and nucleoporin133 are required for the induction of calcium spiking, one of the earliest physiological responses detectable in root hairs exposed to purified Nod-factor.

To establish symbiosis, *Rhizobia* gain access to single plant cells where they are installed in symbiosomes surrounded by a peribacteroid membrane. In Lotus, infection occurs via an infection thread that takes the bacteria through root hairs into the root cortex and distributes them to cells, which become infected symbiosome containing nitrogen-fixing cells. In response to attached bacteria, root hairs deform and curl, setting up a pocket that provides a site for infection thread initiation (Geurts et al., 2005 *Curr. Opinion Plant Biol.*, 8: 346-352). Infection threads are plant-derived structures originating from plasma membrane invagination, accompanied by external deposition of cell wall material. In advance of the inward progressing intracellular thread, root cortical cells dedifferentiate and re-enter the cell cycle to initiate the nodule primordium. Later in the process, pattern formation and cell differentiation specify tissue and cell types including the infected cells that endocytose *Rhizobia*. In the mature functional nodule, peripheral vascular bundles are connected to the root vasculature and the main tissues/cell types can be distinguished (Pawlowski and Bisseling, 1996, *Plant Cell* 8: 1899-1913).

Analysis of a group of nodulation mutants, including some that fail to show calcium oscillations in response to Nod-factor signals, has revealed that in addition to the lack of nodulation, these mutants are unable to form endosymbioses with arbuscular mycorrhizal fungi. This implies that a common symbiotic signal transduction pathway is shared by two types of endosymbiotic relationships, namely root nodule symbiosis, which is largely restricted to the legume family, and arbuscular mycorrhizal symbiosis, which is common to the majority of land plant species. This suggests that there may be a few key genes which dispose legumes to engage in nodulation, and which are missing from crop plants such as cereals. The identification of these key genes, which encode functions which are indispensable for establishing a nitrogen fixing system in legumes, and their transfer and expression in non-nodulating plants, has long been a goal of molecular plant breeders. This could have a significant agronomic impact on the cultivation of cereals such as rice, where production of two harvests a year may require fertilisation with up to 400 kg nitrogen per hectare.

In summary, there is a need to transfer the nodule formation capability and nitrogen fixation properties of legume crops into non-nodulating crops in order to meet the nutritional needs of a growing global population, while minimising the future use of nitrogen fertilisers and their associated negative environmental impact.

SUMMARY OF THE INVENTION

A first embodiment of the invention is a DNA molecule encoding a Calcium and Calmodulin-dependent protein kinase (CCaMK) polypeptide comprising an amino acid sequence selected from among: SEQ ID NO: 7, 8, 9, 10, 11, 15, 26 and 27, wherein the amino acid residue corresponding to Xaa is selected from among isoleucine, leucine, valine, methionine, alanine, phenylalanine, tyrosine, tryptophan, arginine, lysine, glycine, histidine, aspartate, asparagine, glutamate, glutamine, proline and cysteine, an orthologue of (a) and a truncation of (a) or (b), capable of inducing spontaneous nodule formation in a plant.

A second embodiment of the invention is a Calcium and Calmodulin-dependent protein kinase (CCaMK) polypeptide consisting of an amino acid sequence selected from among: (a) SEQ ID NO: 7, 8, 9, 10, 11, 15, 26 and 27, wherein the amino acid residue corresponding to Xaa is selected from among isoleucine, leucine, valine, methionine, alanine, phenylalanine, tyrosine, tryptophan, arginine, lysine, glycine, histidine, aspartate, asparagine, glutamate, glutamine, proline and cysteine; (b) an autophosphorylation-deficient CCaMK allelic variant of (a); (c) an autophosphorylation-deficient CCaMK orthologue of (a); and (d) a truncation of (a), (b) or (c).

A further embodiment of the invention is a genetically modified plant characterised by having a nucleotide sequence encoding a polypeptide comprising an Calcium and Calmodulin-dependent protein kinase (CCaMK) consisting of an amino acid sequence selected from among: (a) SEQ ID NO: 7, 8, 9, 10, 11, 15, 26 and 27, wherein the amino acid residue corresponding to Xaa is selected from among isoleucine, leucine, valine, methionine, alanine, phenylalanine, tyrosine, tryptophan, arginine, lysine, glycine, histidine, aspartate, asparagine, glutamate, glutamine, proline and cysteine; (b) an autophosphorylation-deficient CCaMK allelic variant of (a); (c) an autophosphorylation-deficient CCaMK orthologue of (a); and (d) a truncation of (a), (b) or (c), wherein said plant is capable of spontaneous nodule formation.

The invention is further directed to the use of a nucleic acid molecule encoding a Calcium and Calmodulin-dependent protein kinase (CCaMK) consisting of an amino acid sequence selected from among: (a) SEQ ID NO: 7, 8, 9, 10, 11, 15, 26 and 27, wherein the amino acid residue corresponding to Xaa is selected from among isoleucine, leucine, valine, methionine, alanine, phenylalanine, tyrosine, tryptophan, arginine, lysine, glycine, histidine, aspartate, asparagine, glutamate, glutamine, proline and cysteine; (b) an orthologue of (a); and (c) a truncation of (a) or (b), as a transgene to produce the genetically modified plant of the invention in its various embodiments.

The invention is further directed a method of producing a genetically modified plant according to the invention in its various embodiments, characterised by introducing a gene cassette comprising said nucleotide sequence encoding said polypeptide and selecting a transgenic plant and its progeny expressing said polypeptide.

The invention further includes a genetically modified plant produced according to a process of DNA mutagenesis and selecting a plant capable of spontaneous nodule formation, or by a method of transformation with a transgene encoding a CCaMK of the invention.

The invention further includes a seed or a crop obtained from the genetically modified plant of the invention. Furthermore the invention is directed to the use of a genetically modified plant according to the invention in a breeding program, and a plant selected in the breeding program comprising a nucleotide sequence encoding a polypeptide comprising a Calcium and Calmodulin-dependent protein kinase (CCaMK) consisting of an amino acid sequence selected from among: (a) SEQ ID NO: 7, 8, 9, 10, 11, 15, 26 and 27 wherein the amino acid residue corresponding to Xaa is selected from among isoleucine, leucine, valine, methionine, alanine, phenylalanine, tyrosine, tryptophan, arginine, lysine, glycine, histidine, aspartate, asparagine, glutamate, glutamine, proline and cysteine; (b) an autophosphorylation-deficient CCaMK allelic variant of (a); (c) an autophosphorylation-deficient CCaMK orthologue of (a), and (d) a truncation of (a), (b) or (c), wherein said plant is capable of spontaneous nodule formation.

(A), (B), (C) nfr1-1snf1-1 plants 5 weeks post-inoculation with *M. loti*. Arrowheads indicate pink nodules (seen as black nodules). Arrows indicate white (non-infected) nodules. The aerial part of the plants with pink nodules is dark green and has significant growth (indicated by the stippled line) compared to the nitrogen-starved plants with white nodules. (D) Pink nodule formed on nfr1-1snf1-1 double mutant 5 weeks post-inoculation. (E), (F) nfr1-1snf1-1 plants upon inoculation with *M. loti* nodC::Tn5. Pink nodules are indicated by arrowheads. The plant developing a pink nodule shows a difference in growth (indicated by a stippled line) compared to the one with a white nodule.

Figure 6:
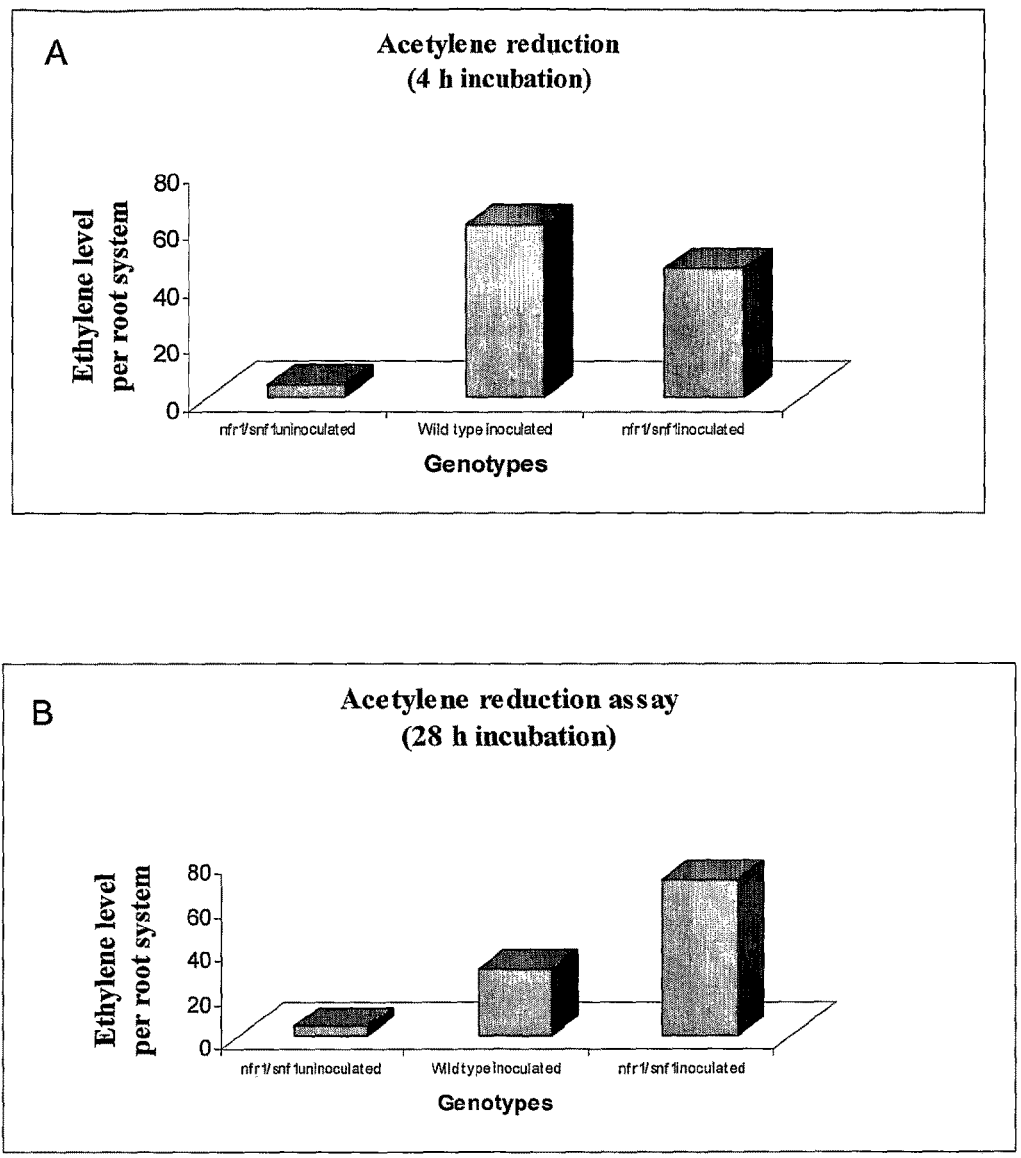

FIG. 6: Acetylene reduction rates in wild-type and double mutant (nfr1/snf1-5g) Lotus japonicus plants with or without inoculation with *Mesorhizobium* lot strain NZP2235, measured after 4 (A) and 28 hours (B) incubation.

Figure 7:
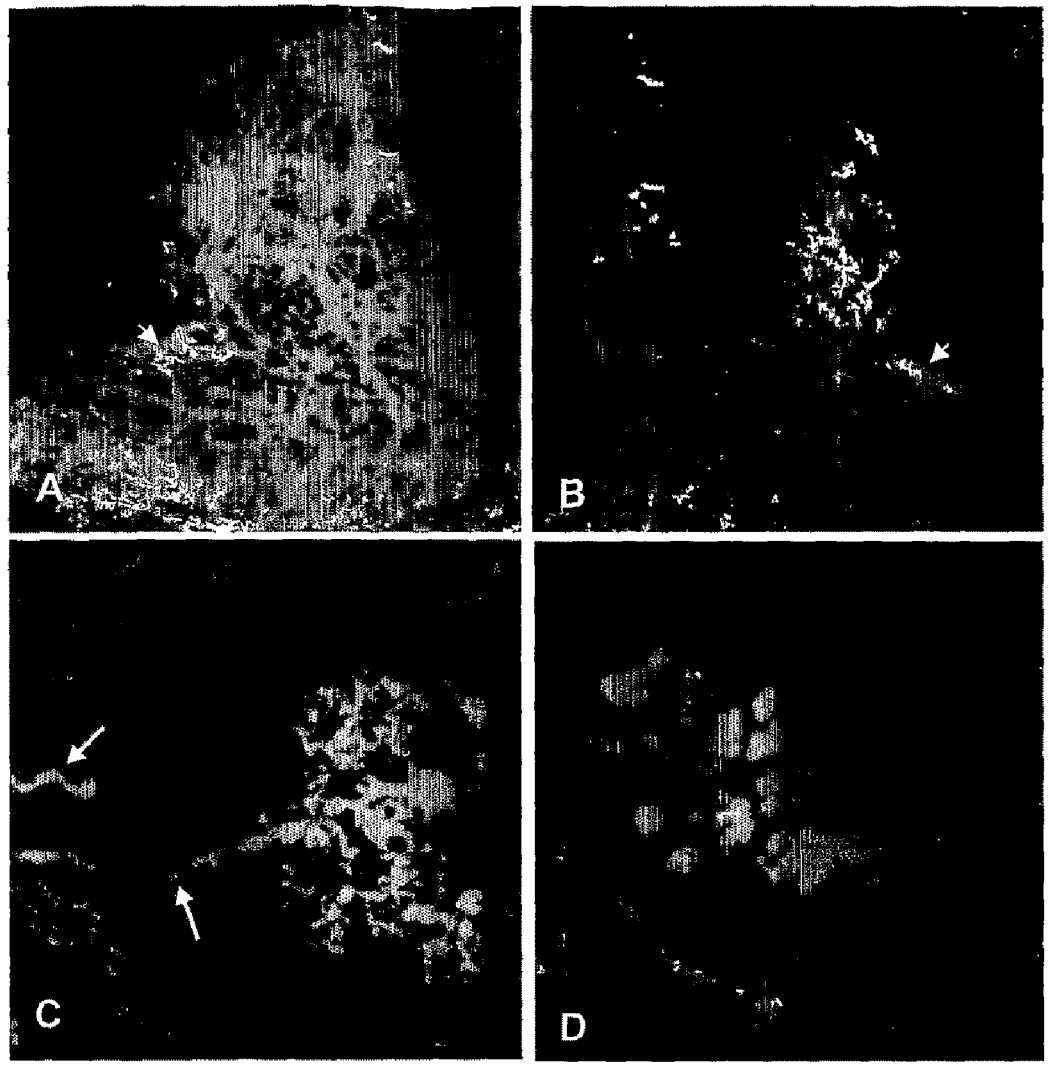

FIG. 7: Confocal microscopy analysis of nfr1-1/snf1-5g nodules.

(A), (B): entire nodule inoculated with *M. loti* carrying a GFP reporter gene. White arrowheads indicate fluorescent green bacteria accumulated on the sides of the nodule, which may correspond to the site of entry of the bacteria into the nodule.

(C), (D): thick sections of a nfr1-1snf1-5g nodule showing the presence of clumps of fluorescent bacteria. In (C) the white arrows indicate a fluorescent stream of bacteria which may be the intercellular space the bacteria recruit to reach the cortical cells. In each of FIGS. 3A, B, C and D, the fluorescent bacteria appear grey.

Figure 8:
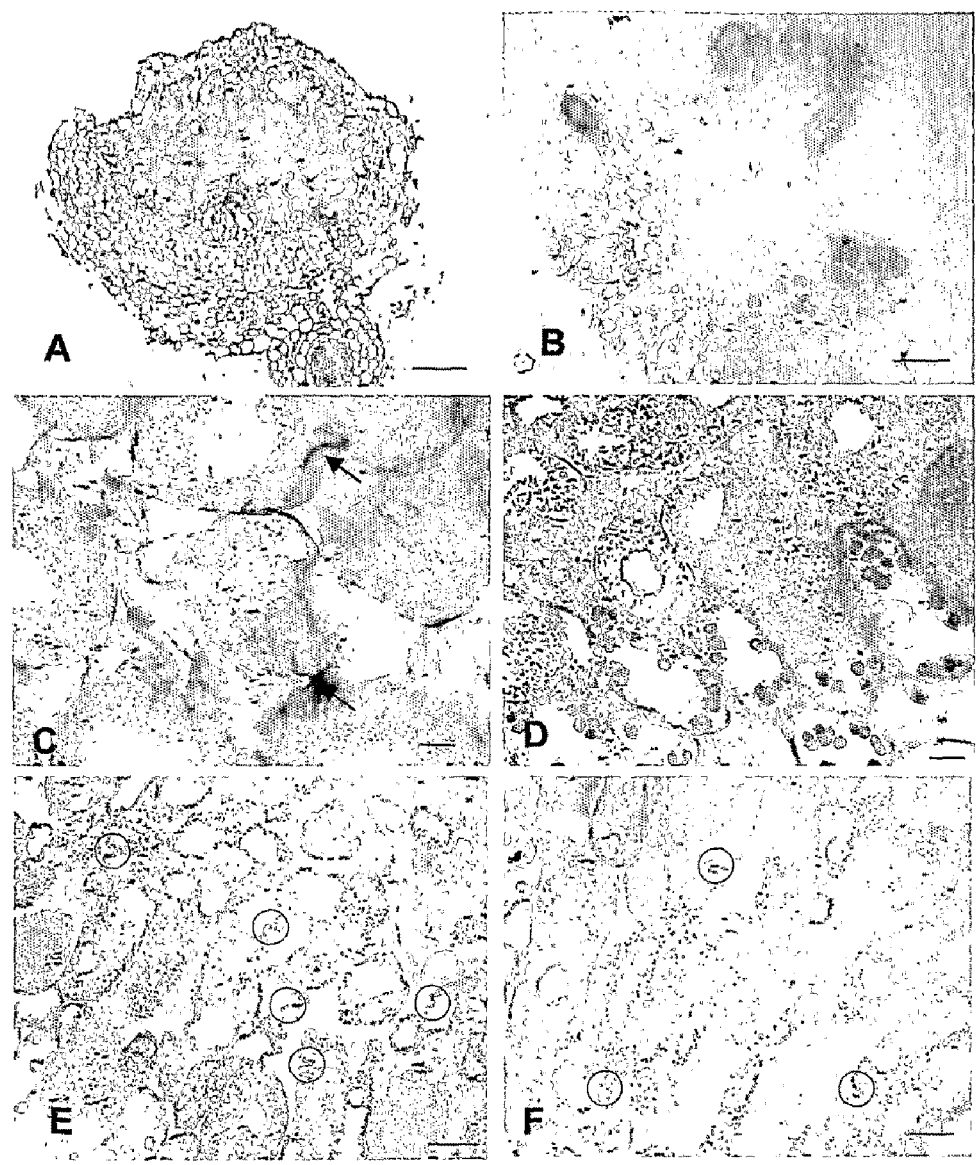

FIG. 8: Light microscopy analysis of nfr1-1/snf1-5g nodules.

Thin sections (6 μm) of nodules formed on nfr1-1/snf1-5g plants upon inoculation with *M. loti* hemA::lacZ, stained with toluidine blue (A), or for lacZ activity (B). The toluidine blue stained bacteria, and the lacZ expressing bacteria appear grey in FIG. 8. Scale bar (A), (B)=200 μm.

(C), (D) close up of respectively (A) and (B) showing the presence of bacteria within and between the cells in the nodule. The bacteria appear dark grey and fill the large cells of the nodule. Arrows indicate bridge-like structures or infection pockets. Scale bar (C), (D)=10 μm, (E), (F) lacZ activity in thin sections of nfr1-1/snf1-5g nodule showing intercellular invaginations (indicated by black circles), putative sites of penetration of the bacteria into the cells. Scale bar (E), (F)=20 μm.

DETAILED DESCRIPTION OF THE INVENTION

Formation of legume root nodules is triggered by Nod-factors synthesised by rhizobial microsymbionts. In the absence of *Rhizobia*, purified Nod-factors can act as mitogens/morphogens and induce the formation of empty nodules when applied in nano- to pico-molar concentrations to the roots of compatible legumes.

The present invention provides a plant expressing a modified $Ca^{2+}$/calmodulin dependent protein kinase (CCaMK) that triggers de-differentiation and reactivation of root cortical cells independent of Nod-factor perception and Nod-factor induced $Ca^{2+}$ spiking, leading to spontaneous nodule formation. A plant expressing this modified CCaMK, encoded by an mutant allele (snf1-5g) of a wild type Snf1 gene was isolated from a mutagenised population of Lotus seedlings, that were screened for the ability to nodulate in the absence of either *Rhizobium* or nod factors, under conditions of nitrogen-starvation.

The modified CCaMK protein expressed by the plant of the invention has a predicted mass of about 60 kD (Table 3). The CCaMK is characterised by various structural and functional domains (Table 4), including a putative bipartite nuclear localization sequence in the N-terminal domain, followed by a kinase domain of about 300 amino acids comprising motifs characteristic of serine/threonine kinases, followed by a putative calmodulin-binding domain, and finally three or four motifs with similarity to the visinin-like EF hands of lily CCaMK kinase, located in the C-terminal domain. According to the present invention, the modified CCaMK protein expressed by the plant is characterised by the absence of a threonine residue at a position corresponding to $T^{265}$ of wild type CCaMK encoded by the *Lotus japonicus* Snf1 gene. Accordingly, the amino acid residue, corresponding to $T^{265}$ of wild type Snf1 CCaMK may be deleted, or may be substituted by any amino acid other than threonine in the modified CCaMK of the invention. Said amino acid residue may be conservatively substituted by an amino acid selected from among alanine, valine, isoleucine, methionine, tryptophan, phenylalanine and tyrosine; or, alternatively, by an amino acid selected from among isoleucine, leucine, valine or alanine. This modified CCaMK of the invention includes homologues from a number of plants, including lily, tobacco, pea, *Medicago truncatula, Physcomitrella* and a cereal, e.g. rice, in which the amino acid residue, corresponding to $T^{265}$ of wild type Snf1 CCaMK may be deleted, or may be substituted by any amino acid other than threonine (based on sequence alignment; see Table 3).

The modified CCaMK protein of the invention is a component of the common signal transduction pathway that regulates both *Rhizobial* nodulation and arbuscular mycorrhizae symbiosis in legumes. The modified CCaMK was identified in mutant *Lotus* plants that exhibit both normal nod-factor perception and calcium spiking, indicating that CCaMK acts downstream of $Ca^{2+}$ spiking in the common signal transduction pathway. While not wishing to be bound by theory, it is believed that wild type CCaMK protein kinase is activated in response to root hair calcium spiking, and transduces the $Ca^{2+}$ oscillations in legume root hairs to stimulate the common pathway to form nodules. In plants expressing the modified CCaMK, this pathway is activated in the absence of *Rhizobium* and/or nod-factors leading to re-initiation of cell division in the root cortex and development of spontaneous nodules.

The modified CCaMK encoded by the snf1-5g gain of function allele in Lotus is characterised by a substitution of $T^{265}$ to I. In the lily CCaMK protein the corresponding $T^{267}$ is the site for calcium-dependent autophosphorylation, which serves to increase its affinity for CaM, and subsequently leads to both activation of the kinase domain as well as a fast, time-dependent inactivation associated with protein aggregation. In vivo activity of wild type *Lotus* CCaMK may therefore be regulated by the balance between calcium mediated activation processes and inactivation by protein aggregation, constituting a very sensitive molecular switch mechanism. It is proposed that the absence of an autophosphorylation site in modified CCaMK would keep the kinase in its ground state, with a low but stable activity that is not subject to autophosphorylation-dependent inactivation through aggregation. This hypothesis together with a multimeric protein composition would explain the recessive nature of the snf1-5g mutation. Heterozygotes would still make autophosphorylated multimeric protein destined for rapid aggregation, while the enzyme in homozygous snf1-5g plants would be stable. Hence, a further embodiment of the invention provides a plant expressing said modified CCaMK protein that also lacks a functional autophosphorylation site, and is capable of spontaneous nodulation. In a further embodiment the autophosphorylation site in the expressed autophosphorylation-deficient CCaMK is located in a position in the CCaMK polypeptide that corresponds to $T^{265}$ in *Lotus* CCaMK or to the corresponding autophosphorylation site in lily CCaMK.

The present invention provides a plant expressing said genetically modified CCaMK from *Lotus* having SEQ ID NO: 26 [or SEQ ID No: 6, wherein Xaa=I), or (genetically) modified CCaMK homologues derived from *Medicago truncatula* (SEQ ID NO: 7), *Pisum sativum* (SEQ ID NO: 8), *Nicotiana tabacum* (SEQ ID NO: 9, 10), *Lilium longiflorum* (SEQ ID NO: 11), *Oryza sativum* (SEQ ID NO: 27 [or SEQ ID NO: 14 wherein Xaa=I]), and *Physcomitrella patens* (SEQ ID NO: 15) wherein the amino acid residue corresponding to Xaa is any residue other than S or T, or wherein Xaa is deleted. Furthermore, the invention encompasses truncations of the modified CCaMK of the invention, wherein said truncated CCaMK retains its functional activity, namely that it confers the ability to form spontaneous nodules when expressed in a plant. In a further embodiment the invention encompasses orthologues or allelic variants (encoded variants of the same gene) that share sequence identity with the modified CCaMK having any one of SEQ ID NO: 7, 8, 9, 10, 11, 15, 26 [or SEQ ID No: 6, wherein Xaa=I], and 27 [or SEQ ID NO: 14, wherein Xaa=I] wherein the amino acid residue corresponding to X is any residue other than S or T, or wherein Xaa is deleted. The terms orthologue and allelic variant embrace proteins having substantial sequence identity and serving the same function in an organism, and commonly located in a similar position in the genome. The orthologue or allelic variant of the CCaMK of the invention shares a percent sequence identity with said modified CCaMK, selected from the group consisting of at least 60, 65, 70, 75, 80, 85, 90, 95, and 98 percent, and has all of the functional properties of the modified CCaMK of the invention, such that when expressed in a plant of the invention it confers the ability to form spontaneous nodules. In a further embodiment the orthologue/variant allele is a CCaMK that is autophosphorylation deficient.

In a further embodiment, the invention provides a plant comprising a gene encoding the modified CCaMK, wherein said gene is a snf1-5g or snf1-6 gene consisting of the DNA sequence of SEQ ID NO: 4, 16, or fragments thereof, or the snf1-5g or snf1-6 cDNA comprising the DNA sequence of SEQ ID NO: 5, 17 or fragments thereof, wherein said sequence or fragments thereof encode a full-length or truncated functional modified CCaMK capable of causing spontaneous nodulation when expressed in a plant. In an alternative embodiment, the DNA sequence encoding the modified CCaMK is the rice snf1 gene comprising the DNA sequence of SEQ ID NO: 12, or the rice snf1 cDNA comprising the DNA sequence of SEQ ID NO: 13 or fragments thereof encoding a full-length or truncated functional modified CCaMK capable of causing spontaneous nodulation when expressed in a plant.

According to the present invention the DNA sequence encoding the modified CCaMK protein of the invention is operably linked to a promoter DNA sequence capable of driving expression of said CCaMK in a plant, and to a 3' terminator sequence. The promoter can be a promoter directing expression of said CCaMK in root tissues of a plant and/or in cells destined to become nodule primordia and mature into nodules. Suitable examples of a promoter and terminator include the promoter and terminator sequence of the corresponding wild type CCaMK gene. An example of a heterologous constitutive promoter includes the 35SCaMV promoter (Acc. No: V00141, J02048). A transgene (gene cassette) comprising a DNA sequence encoding a modified CCaMK protein of the invention operably fused to a promoter sequence and optionally a terminator sequence can be constructed by recombinant DNA techniques.

According to the present invention, a transgene comprising a DNA sequence encoding the modified CCaMK can be used to generate a plant expressing the modified CCaMK of the invention. The transgene can be stably integrated into the genome of a host plant by transformation techniques well know to one skilled in the art, as illustrated in example 6 and 7. Furthermore, binary vectors and *Agrobacterium tumefaciens*-based methods for the stable integration of transgenes into all major cereal plants are know, as described for example for rice (Hiei et al, 1994, *The Plant J.* 6; 271-282), and maize (Yuji et al, 1996, *Nature Biotech.* 14: 745-750). A DNA sequence encoding a modified CCaMK can also be introgressed into another plant by crossing with a genetically modified plant expressing the modified CCaMK of the invention.

The genetically modified plant of the invention comprising a DNA sequence encoding a modified CCaMK, can also be obtained by mutagenesis, whereby the genetically modified plant of the invention having a mutation in the CCaMK gene and encoding a modified CCaMK may be selected, as illustrated in example 1.

The genetically modified plant of the invention, whether generated by mutagenesis, transformation with a transgene of the invention, or introgression of said mutated gene or transgene, can be used in a breeding program, in order to select plants with the ability to fix nitrogen, or enhanced nitrogen fixation ability, that have inherited the gene encoding the modified CCaMK. The invention thus encompasses a genetically modified plant, produced by transformation of a natural plant that is capable of nitrogen fixation. The expression of a gene encoding a modified CCaMK in a nitrogen-fixing plant, such as a member of the Leguminoseae (such as soybean, bean, pea, peanut, chickpea, cowpea, lentil, pigeonpea, alfalfa and clover), has particularly utility with respect to enhancing the nitrogen-fixing ability of said plant under one or more environmental growth conditions. The expression of a gene encoding a modified CCaMK in a crop plant that does not naturally fix nitrogen, such as a monocotyledenous plant including a member of the cereals (such as wheat, rye, oats, barley, sorghum, millet, maize, Poaceae grass and rice), has particularly utility with respect to enabling nitrogen-fixation. Plants, as well as plant progeny, selected in such a breeding program may be cultivated for the purpose of harvesting a crop, where the crop may be the vegetative plant parts, e.g. leaf, stem or tuber, or reproductive parts, including flowers, seed, caryopsis, cob or fruit.

The examples given below serve to illustrate the various embodiments of the invention and their respective features. They demonstrate that a plant, e.g. *Lotus*, that is homozygous for a gene encoding the modified CCaMV polypeptide of the invention, forms spontaneous nodules that can be infected by nitrogen-fixing symbiotic bacteria e.g. *M. loti*, and which are capable of fixing nitrogen and supporting plant growth under nitrogen-limiting conditions. The formation of nitrogen-fixing nodules following inoculation with nitrogen-fixing bacteria in said spontaneously nodulating plants is not dependent on nod factor production by the infecting bacteria or nod factor perception by the infected plant. This indicates that only a subset of nodulation-related genes are required in order for nitrogen fixation to occur in a spontaneously nodulating plant expressing a modified CCaMV following inoculation with a rhizobium bacterium. The unique properties of the modified CCaMV of the invention may be exploited both to enhance nitrogen fixation in existing nitrogen fixing plants, as well as in establishing nitrogen fixation in non-nodulating plants.

Example 1

Isolation of Spontaneous Nodule Formation (snf) Mutants of *Lotus japonicus*

Six genetically stable spontaneous root nodule formation (snf) mutant lines of *Lotus japonicus*, isolated from a mutagenised population, are described. Large scale screening for snf mutants was performed in the model legume *Lotus japonicus* ecotype Gifu, which has a small diploid genome, particularly suited for genetic studies. Mutant screening was carried out on plants derived from an EMS mutagenised population known to produce mutants with high frequency (Perry et al., 2003 *Plant Physiol.* 131: 866-871), according to the following procedure.

A. Six Genetically Stable snf Mutant Lines of *Lotus japonicus* Isolated

Seeds of 2400 M3 pools, composed of seeds from 12665 independent M2 plants, were surface sterilised, as described previously (Handberg and Stougaard, 1992 *Plant J.*, 2: 487-496), pre-soaked in sterile water overnight and germinated in a double-tray arrangement containing clay granules in the upper tray. The lower tray, containing 3 liters of half-concentration B&D nutrients, without $KH_2PO_4$, (Broughton and Dilworth, 1971 *Biochem J.* 125: 1075-1080), was connected to the upper tray through a wick. Double-trays were covered with foil, autoclaved and the $KH_2PO_4$ component of the B&D nutrients was added before sowing the seeds. Screening was performed under *Rhizobium*- and nitrogen-free conditions by autoclaving or filter sterilizing all material and solutions before use. The seeds were germinated and grown in isolation at high density, 90% humidity and 25° C., under *Rhizobium*-free axenic conditions, in the absence of nitrogen-containing nutrients, for 5 weeks before screening. In total more than 500,000 individual plants were screened for spontaneous nodule formation.

In the primary screen, putative mutants displaying nodule-like structures were found in 86 out of 2400 seed pools. Each of these putative mutants were rescued by transfer to nitrogen-containing nutrients and grown for seed production. Progeny of each self-fertilized plant were subsequently screened for spontaneous nodulation in order to confirm the presence of the snf phenotype and its inheritance. Mutants from 6 pools retained their mutant phenotype, demonstrating the stability of the snf phenotype. Progeny of the 80 remaining putative mutant plants lacked nodule-like structures.

A summary of the primary screening is shown in Table 1. Mutations causing spontaneous nodulation were rare, since only 0.04% of the 12665 EMS M2 lines gave rise to snf mutants. The snf assignment for spontaneous nodule formation was given to each mutant line, followed by a number according to the order in which they were found. Where more than one mutant plant was found in a pool, they were given the same number and considered as likely siblings.

TABLE 1

Summary of primary screening for snf mutants of *L. japonicus*.

| Category* | Number of pools | Number of mutants/pool | Number of nodules/mutant | Genetically-stable mutants |
|---|---|---|---|---|
| 1 | 2 | >2 | >2 | 2 (snf1, snf2) |
| 2 | 3 | 1 | >2 | 3 (snf3, snf5, snf6) |
| 3 | 1 | >2 | 1 | 1 (snf4) |
| 4 | 80 | 1 | 1 | 0 |
| 5 | 2313 | 0 | 0 | 0 |

*Putative mutants were divided into different catagories. The number of genetically stable snf mutant lines resulting from the primary screening of the EMS treated *Lotus japonicus* is listed.

B. snf1 Segregates as a Single Recessive Locus

All snf mutants were selfed and crossed to wild type *L. japonicus* ecotype Miyakojima as described previously (Jiang and Gresshoff, 1997 *Mol. Plant-Microbe Interactions* 10: 59-68). DNA from the F1 leaves was extracted as described in Handberg and Stougaard, 1992 (supra) and heterozygosity in the F1 plant was confirmed using microsatellite markers showing polymorphisms between Gifu and Miyakojima. Segregating F2 generations were screened for spontaneous nodulation, 5 weeks post-germination, to determine the genetic inheritance.

The F2 progeny from snf1 crosses segregated 69 snf phenotypes and 289 wild type phenotypes (wild type Snf), wherein $\chi^2$ is 1.74 and $\alpha=0.05$ is 3.84, indicating monogenic recessive inheritance of snf1.

Example 2

Growth, Development and Nodulation of Spontaneous Nodule Formation (snf1) Mutants of *Lotus japonicus*

A. snf1 Mutants have a Normal Growth Phenotype

The snf1 mutants of *Lotus*, more specifically snf1-5g belonging to the snf1 category, show normal growth and development to maturity, indicating an absence of pleiotropic effects of the snf1 mutation. When snf1 mutant plants are grown under axenic nitrogen-deficient conditions, they show symptoms of nitrogen-starvation, including anthocyanin accumulation in the stem, light green leaves and poor growth of the aerial part of the plants (FIG. 1A). Their nodules are white, round shaped and distributed on a normal looking root system (FIGS. 1A, B, C, F).

B. Nodules of Axenically Grown snf1 Mutants are Devoid of *Rhizobia*

The bacterial content of nodules of snf mutants was examined in order to confirm that spontaneous nodule formation was a plant mutant phenotype and not, for example, due to delayed infection from accidentally contaminating *Rhizobium*. Five spontaneous nodules from five different plants of each snf line were surface sterilized in 12% hypochloride, washed and then crushed in sterile water, and serial dilutions thereof were plated on standard rhizobial YMB medium and incubated at 28° C. for 48 h before counting the *Rhizobium* colony forming units, according to the procedure of Vincent in 'A manual for the practical study of root nodule bacteria' IBP handbook no: 15, Oxford Blackwell Scientific Publ., (1970). No *Rhizobium* or other bacteria were recovered from these thirty nodules. Further evidence for the absence of *Rhizobium* was obtained by inoculating wild type *Lotus* plants with suspensions of three crushed, non-surface sterilized nodules derived from each snf line. None of these inoculated wild type *Lotus* plants developed nodules, thereby confirming that snf nodules were empty and devoid of bacteria capable of nodulating *Lotus* plants.

C. Nodules of Axenically Grown snf1 Mutants are Genuine Nodules

Spontaneous nodules in snf mutants comprise structural features characteristic of wild type root nodules with respect to their tissue and cellular histology, and ontogeny. Spontaneous root nodules from snf mutants, examined by light microscopy and Scanning Electron Microscopy (SEM), have the features of fully differentiated root nodules, including a globular shape; attachment in the root cortex; and two peripheral vascular bundles, as in wild type rhizobial nodules (FIG. 1G). Peripheral vascular bundles, in particular, distinguish root nodules from lateral roots, which only have a central vascular bundle. The only detectable structural differences between snf and wild type nodules were the absence of bacteroids and infection threads in snf nodules, and the presence of starch granules, which is also typical of wild type plants inoculated with rhizobial mutants unable to fix nitrogen (FIG. 2ABC). Cells in snf nodules show a dense cytoplasm with many mitochondria and lipid bodies. Sections of vascular tissue show xylem vessels with many branched wall ingrowths (FIG. 2D).

The ontogeny of spontaneous nodule formation in snf mutants is initiated from nodule primordia derived from cell division in the root cortex as occurs in *Rhizobium*-induced nodulation. This was demonstrated by the pattern of expression of a Nin-GUS transgene transformed into snf1-5g plants. The Nin gene encodes a putative transcription factor whose expression during nodulation provides a marker for both initiation and development of nodule primordial. During the formation of spontaneous nodules, the Nin-GUS gene was expressed in nodule primordial cells developing in front of xylem poles in snf roots (FIG. 1J,L). However, Nin-GUS expression was only detected in the rhizobial invasion zone, immediately behind the root tip, following inoculation with *M. loti*. This confirms that snf1-5g allele confers both the ability to form *Rhizobium* nodules and spontaneous nodules.

D. snf Mutants Exhibit Both Spontaneous Nodulation and *Rhizobium*-Induced Nodulation The regulation of *Rhizobium*-infected nodule formation by the host plant in wild type *Lotus* plants is conserved in snf mutants, even though spontaneous nodulation events in these mutants are completely uncoupled from bacterial infection. In wild type plants, germinated on agar plates, *Rhizobium*-induced nodules are first visible under a stereo-microscope about 7 days post-germination and inoculation (FIG. 3A), reaching a plateau of 4.5 nodules/plant after 40 days. snf mutants develop normal nodules on inoculation with *Rhizobium*, which are visible 7 days post-inoculation, with 4.5 nodules/plant as in wild type plants. On average, *Rhizobium*-induced nodule numbers in snf1 mutants reach a plateau a week earlier than in wild type plants and nodule development appears to progress slightly faster in snf1 mutants. Interestingly, *Rhizobium*-induced nodules on snf mutants do not completely suppress spontaneous nodulation (FIG. 1N) as spontaneous and rhizobial nodules are occasionally observed on the same root. These data indicate that snf mutants are not compromised in *Rhizobium*-induced nodulation and mutant nodulation genes in snf serve a functional and integral role in this process.

Figure 3:
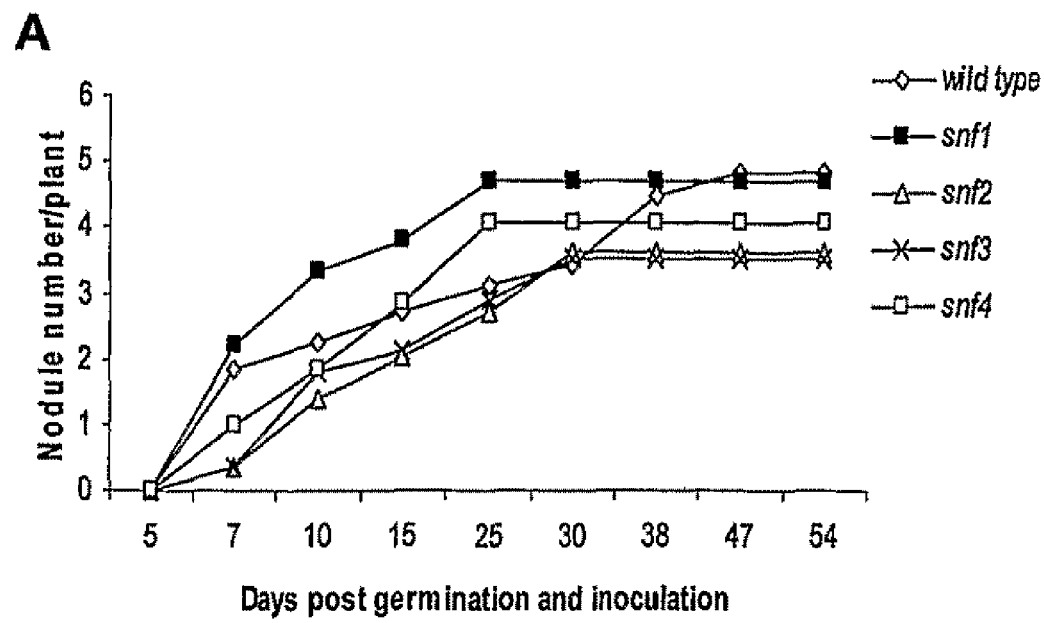
FIG. 3: Nodulation time course for snf mutants in comparison to wild type Lotus (Gifu). (A) nodulation in the presence of *Rhizobium*. (B) Spontaneous nodulation in snf mutants in the absence of *Rhizobium*. Approximately 80 plants for each mutant were scored for nodulation at regular intervals.
Figure 3:
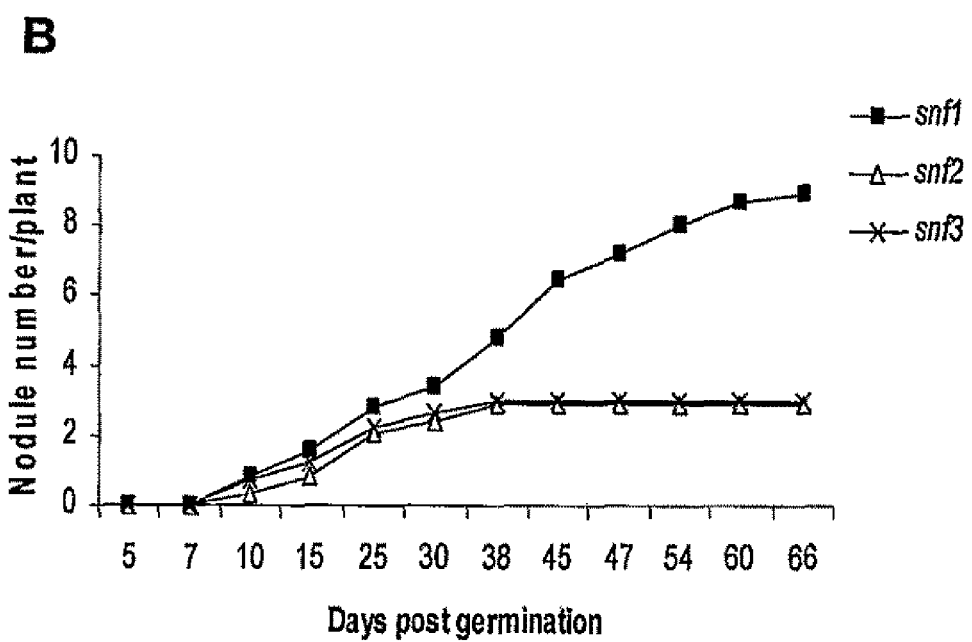

Spontaneous nodulation in the snf1, in the absence of *Rhizobium*, is observed 10 days post germination, reaching a plateau 30 days post germination (FIG. 3B). The snf1 mutant develops around 8 nodules and the nodule number stabilizes later, approximately 66 days post inoculation (FIG. 3B).

E. Nitrogen Inhibits Spontaneous Nodulation in snf Mutants

Spontaneous nodulation in snf mutants is regulated by nitrogen in the same manner as *Rhizobium*-induced nodulation in wild type *Lotus* plants, where nitrogen-limiting conditions promote nodulation. Under non-limiting nitrate conditions, wild type *Lotus* shifts its nitrogen metabolism towards nitrate assimilation and nodulation is suppressed, and development of some nodules is prematurely arrested (Wopereis et al., 2000, *The Plant J.*, 23: 97-114).

Figure 4:
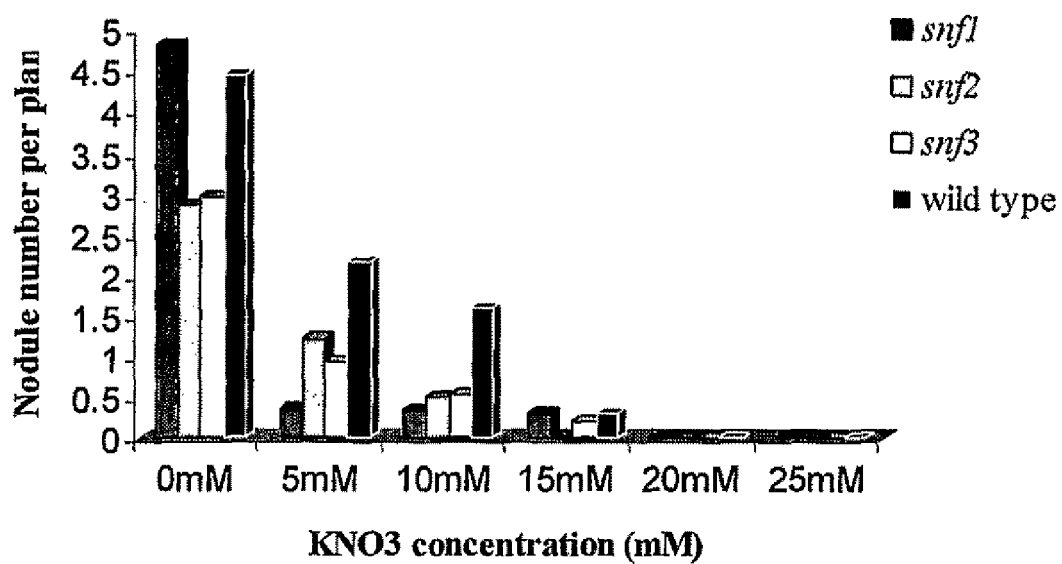
FIG. 4: Suppression of nodulation. Effect of increasing nitrate concentration on *Rhizobium* induced nodulation of wild type (Gifu) and spontaneous nodulation of snf mutants. Nodule number was assessed 5 weeks post germination.

The nitrogen sensitivity of spontaneous nodulation in snf mutants was demonstrated by growing snf mutant seedlings axenically on solid ¼ B&D growth media containing different concentrations of potassium nitrate. Nodule number were significantly decreased at 5 mM $KNO_3$, particularly in snf1 mutants, and completely suppressed by 20 mM $KNO_3$ (FIG. 4), paralleling the nitrogen sensitivity of wild type plants.

F. snf Mutants are Mycorrhized

*Lotus*, like other legumes, can enter into symbiosis with mycorrhizal fungi of the *Glomales*, whose hyphae colonize the roots and establish vesicular arbuscular mycorrhizal symbiosis. One week old snf seedlings were transferred to chive nurse pots containing clay granules mixed with dried fungal inoculum and grown in a humid growth cabinet at 25° C. for 4 to 5 weeks (Wegel et al., 1998, *Mol. Plant-Microbe Interactions* 14: 839-847). Plants were scored for mycorrhizal colonization using the ink staining procedure (Vierheilig et al., 1998, *Appl. and Environmental Microbiol.*, 64: 5004-5007). The screening for mycorrhizal infection was performed in the absence of *Rhizobium*.

Figure 1:
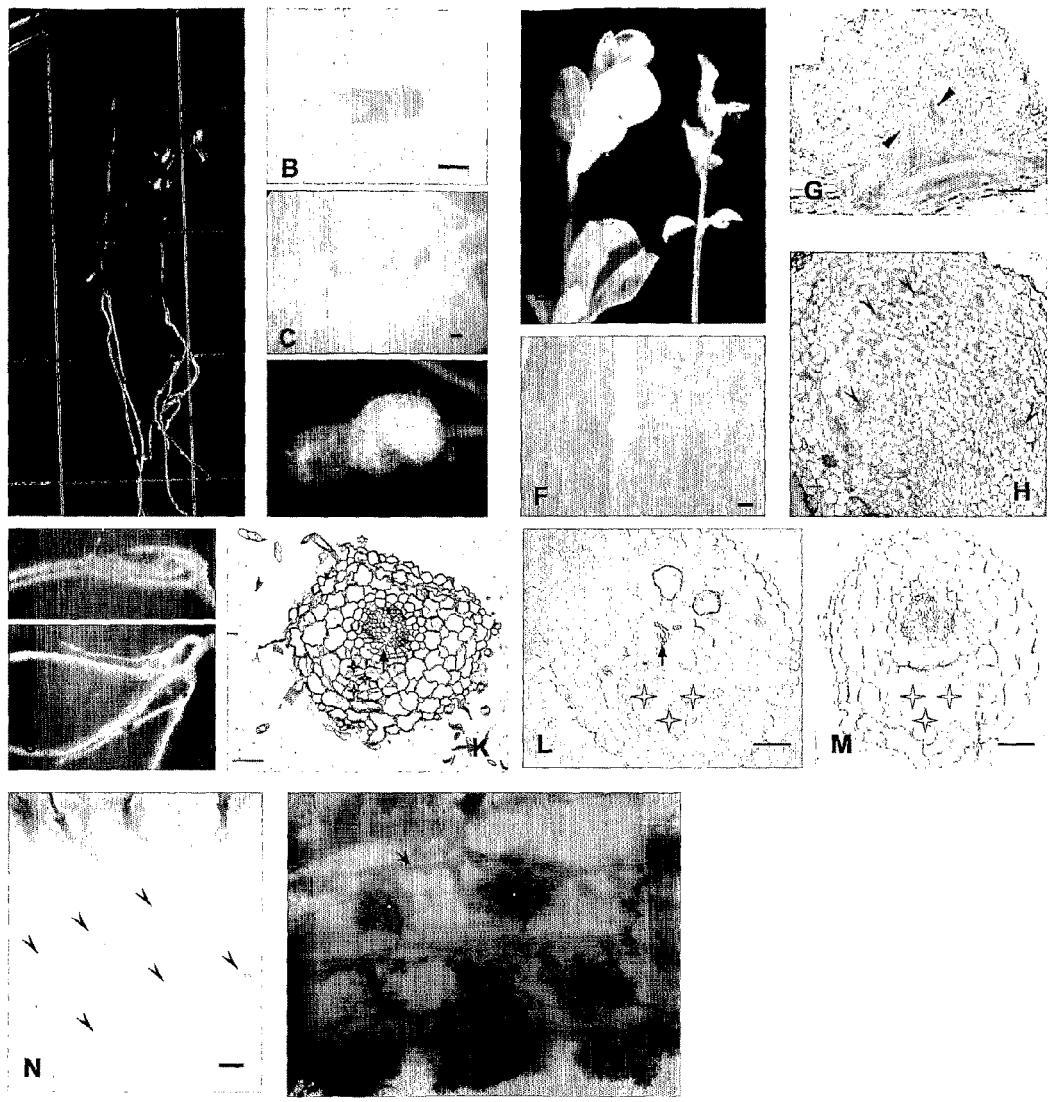
FIG. 1: Phenotype of spontaneous nodulation mutants. (A, E) To the left a *Lotus japonicus* wild type plant inoculated with *M. loti*. Symbiotic nodules marked with arrows. To the right, a snf mutant with spontaneous nodules (arrowheads) grown without nitrogen and in the absence of *Rhizobium*. Wild-type and mutant plants are 5 weeks post germination. (B) Symbiotic root nodules induced on wild type *Lotus japonicus* ecotype Gifu after inoculation with *M. loti*. Bar=1000 µm. (C, D, F) Spontaneous nodules formed on snf mutant, 5 weeks post germination. Bar=500 µm. (G) Longitudinal thin section (4 µm) of snf nodule 8 weeks post germination. Bar=100 µm. (H) Longitudinal thin section (4 µm) of snf nodule after staining with potassium iodide. Upper arrows show accumulation of starch granules. Lower arrows indicated vascular strands. Bar=50 µm (I) Roots of Nin-GUS transformed line of wild type *Lotus japonicus*. (J) Roots of Nin-GUS transformed line of snf mutant *Lotus japonicus* showing GUS expression in nodule primordia. (K) Transverse section of infected root nodule from wild type *Lotus japonicus*; (L, M) and nin-GUS expressing snf spontaneous nodule, where stars indicate cell divisions, and arrows indicate xylem poles. Only primordial cells in front of xylem poles show GUS expression. (N) *Rhizobium* induced (white arrowheads) and spontaneous nodules (black arrowheads) developing on snf mutants 5 weeks post germination. The plants were inoculated with *Mesorhizobium loti* strain NZP2235. Bar=5 mm. (O) Cleared and vinegar stained root of snf mutant showing arbuscule development of mycorrhiza (white stars). White arrows show fungal hyphae growth. Bar=5 µm.
Figure 2:
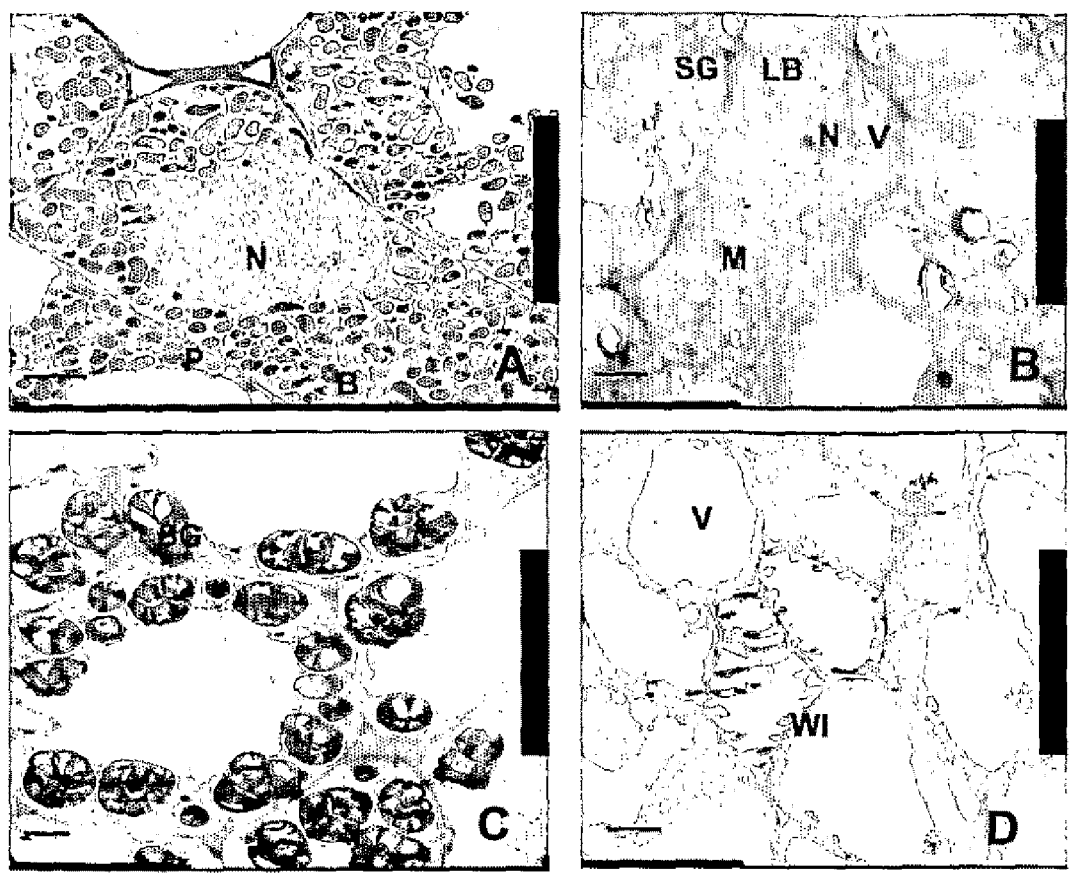
FIG. 2: Electron micrographs. (A) wild type *Rhizobium* induced root nodule and (B) spontaneous snf1 nodule 5 weeks after germination. (A) shows infected cells full of bacteroids while (B) shows non infected cells without any bacteria. (C) Electron micrograph of large cells in snf1 nodule containing a large number of starch grains. (D) Electron micrograph of vascular tissue in 5 weeks old spontaneous nodule from the snf1 mutant showing xylem vessels and xylem parenchyma with wall ingrowth. N nucleus; M mitochondria; V vacuole; SG starch grain; B, bacteroid; P plasma membrane; LB lipid body; WI wall ingrowth. Bar in (A), (B), (C) and (D)=4 µm.

All snf mutants retain the ability to establish mycorrhizal symbiosis, as demonstrated by the colonization, appressoria development, hyphae penetration and branching of *Glomales intraradices* on roots of snf plants (FIG. 1-O). Mycorrhizal infection was as widely spread in snf plants as in wild type control plants (data not shown).

Example 3

Loss of Function Alleles of the Snf Locus

When inoculated with *M. loti* the gain of function (snf1-5g) mutants develop normal nitrogen fixing and bacteria filled root nodules. In contrast, loss of function allelic mutants, snf1-2, are non-nodulating, while leaky snf1-1 mutants regularly develop up to two functional nodules. Loss of function snf1 mutants retain the ability to perceive Nod-factors applied to their roots, as indicated by root hair swelling and root deformation and $Ca^{2+}$ spiking, comparable to the response of wild type plants. This indicates that 'loss of function' and 'gain of function' snf mutations affect a component of the nodulation signal transduction pathway that is down-stream of $Ca^{2+}$ spiking.

Example 4

Map-Based Cloning of snf1-5g

Map-based cloning was employed to localise the recessive gain of function snf1 (snf1-5g) allele and loss of function alleles (snf1-1 and snf1-2). On the genetic map of *Lotus* the Snf1 locus is located on the short arm of chromosome 3, approximately 35 cM from the top. Fine mapping in an F2 population established from an ecotype (Miyakojima MG-20) cross and genotyping of 1745 mutant plants identified markers delimiting the Snf1 locus to a 0.11 cM region (Table 2).

TABLE 2

Genetic map of *Lotus japonicus* snf1

Chromosome 3

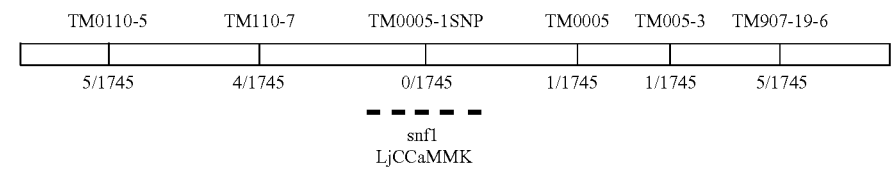

Positions of flanking markers are indicated together with the number of recombinant plants/total number of mapping individuals.

A physical map of this chromosomal region was made from assembled BAC clones. A candidate Snf1 gene, and its mutant allele snf1-5g, was identified in the mapped region based on their sequence homology and functional homology to a Calcium Calmodulin-dependent Kinases, CCaMK, which are known to act downstream of calcium spiking in the symbiotic pathway of Medicago (Lévy et al., 2004, Science 303: 1361-1364) and Pea. Two point mutations were found in the mutant allele snf1-5g (snf1-5g gene: SEQ ID NO: 4 versus wild type Snf1 gene SEQ ID NO: 1), comprising a C to T transition in the coding sequence of the gene, leading to the substitution of threonine$^{265}$ by isoleucine$^{265}$ in the encoded protein (snf1-5g encoded protein: SEQ ID NO: 6 versus wild type Snf1 protein SEQ ID NO: 3) and a further C to T transition in intron 1, that has a length of circa 2 kb (Table 5).

Sequencing of full-length cDNAs isolated from a Lotus nodule library determined the transcription start site 30 nucleotides upstream of the start codon and a 3' untranslated region of 188 nucleotides (snf1-5g cDNA: SEQ ID NO: 5; Snf1 cDNA: SEQ ID NO: 2) and an open reading frame of 1554 nucleotides. Alignment of genomic and cDNA sequences defined a primary structure of Snf1 consisting of 7 exons (Table 5). Southern hybridisation and analysis of the 165 Mb genome sequence available in data bases indicates that Snf1 is represented by a single gene in Lotus.

Example 5

A 'Gain of Function' Calcium Calmodulin-Dependent Protein Kinase (CCaMK)

The isolated snf1-5g gene encodes a CCaMK protein of 518 amino acids with a predicted mass of 57.5 kD, whose structural and functional CCaMK orthologues are present in Medicago truncatula (SEQ ID NO: 7), pea (SEQ ID NO: 8), tobacco (SEQ ID NO: 9, 10), lily (SEQ ID NO: 11), rice (SEQ ID NO: 14, 27), Physcomitrella (SEQ ID NO: 15) (Table 3).

TABLE 3

Multiple alignment of 'gain of function' snf1 CCaMK protein sequences

```
                     • • • •10 • • • • •20 • • • • •30 • • • • •40 • • • • •50 • • • • •60 • • • • •70 • • • • •80
LjCCaMK       1:  MGYDQ.TRKLSDEYEISELGRGGFSVRKCTKKSGN...EKTQ........VAIKTIRRLCSSPS......GTGGGQ:  60
MtCCaMK       1:  MGYG..TRKLSDEYEVSEILGRGGFSVRKCTKKSSIE.EEKSQSQ.......VAIKTIRRLCASNNPSGLPRKKDIGE:  69
PsCCaMK       1:  MGYG..TRKLSDVYEVSEILGRGGFSVRKCTRKSNND.DEKSQSQSKSQSQVAIKTIRRLCTSNN...LPRKKDGGE:  74
NtCCaMK       1:  MGQREDGKTLSDEYEVTDILGRGGFSVRKCTRRRTLH.SGQHHEV........VAIKTIRRFCPPPAP.....EKKSLN:  66
LlCCaMK       1:  MSRHE.SRKLSDDYEVVDVLGKGGFSVRKCISKSRGKN............NDVAIKTIRRYCYTLPGAQR...SQPGQ:  63
OsCCaMK       1:  MSKTE.SRKLSDDYEVVDVLGRGGFSIVRECVSKSEEK............TQVAIKTIRRLCPAMAGMK....Q..GT:  59
Physc.CCaMK   1:  MSDPYGRRLLVDDFHVGPYLGTGGESVVRAGVRKQDN..............LQVAIKTIKKFCYGRG........DHGR:  57

• • • •90 • • • • 100 • • • 110 • • • 120 • • • 130 • • • 140 • • • 150 • • • 160
LjCCaMK      61:  KSTATVMGFRSLRQVSVSDALLTNEILVMRRIVENVSPHPNVIDLYDVCEDSNGVHLVLELCSGGELFDRIVAQDKYAPT: 140
MtCCaMK      70:  KST...IGPFTMRQVSVSDTLLTNEILVMRRIVENVSPHPNVIDLYDVSEDTNGVHLVLELCSGGELFDRIVAQDKYSPT: 146
PsCCaMK      75:  NSTETMMKFRTMRQVSVSDALLTNEILVMRRIVENVSPHPNVIDLYDVSEDTNGVHLVLELCSGGELFDRIVAQDKYSPT: 154
NtCCaMK      67:  KSR...V....PQAALISETLLTNELLVMIKIVEDVSPHPNVIHLYDVCEDPSGVHLVLELCSGGELFDRIAGQARYNRA: 139
LlCCaMK      64:  RGLSP.LGMPTLKQVSVSDALLTNEILVMRRIVEDVSPHPNVIHLHDVSEDANGVHLVLELCSGGELFDRIVAQDRYSPS: 142
OsCCaMK      60:  KPVPG.SGLPMWKQVSISDALLTNEILVMRRIVESVAPHPNVINLHDVSEDVHGVHLVLELCSGGELFDRIVGRDRYSPF: 138
Physc.CCaMK  58:  PGA........QMS.QAEALVKNEIMVMMRIVDEVSPHPNVIHLIDVSEDDGAVHLVLELCRGGELFDRIVQHERYSER: 127

• • • 170 • • • 180 • • • 190 • • • 200 • • • 210 • • • 220 • • • 230 • • • 240
LjCCaMK     141:  RAAAWRQIIAGIPAVIKADIVHRDLKPENCLFLDSRKDSPLKIMDFGLSSVEREFTDPVVGLFGSIDYVSPEALSQGKIT: 220
MtCCaMK     147:  EAATVIHQIASGIPAVHRANIVHRDLKPENCLFLDVRKDSPLKIMDFGLSSVEREFTDPVVGLFGSIDYVSPEALSQGKIT: 226
PsCCaMK     155:  EASIVIHQIVAGIPAIHRANIIHRDLKPENCLFLDVGKDSSLKIMDFGLSSVEREFTDPVVGLFGSIDYVSPEALSQGKIT: 234
NtCCaMK     140:  GAAAVRQIAKGIEALHGASIVHRDLKPENCLFLNQEKRSTLKIMDFGLSSVEDPTDFIVALFGSIDYVSPEALSRENII: 219
LlCCaMK     143:  EAABWQQIASGIAALHKSTIIHRDLKPENCLFLNQEKRSTLKIMDFGLSSVEDPTDFIVALFGSIDYVSPEALSRQVS: 222
OsCCaMK     139:  DAAMVIRQIASGIRALHKASIVHRDLKPENCLFSDKDEKSTLKIMDFGLSSVEDEESDPIVALFGSIDYVSPEALSRQEVS: 218
Physc.CCaMK 128:  DAAKVWRQIASGIAALHQAQIVHRDLKPENCLYVNPLAEAPLKIMDFGLSYIHHNTNSIVGIFGSIDYMAPEQLSLSGIM: 207

• • • 250 • • • 260 • • • 270 • • • 280 • • • 290 • • • 300 • • • 310 • • • 320
LjCCaMK     221:  AKSDWWSLGVILYILLSCYPPFIAONNRQKCQMIINGNFSEYEKKVKGITQSAKQLISSLITVDRSKRPSAQELLSHPWV: 300
MtCCaMK     227:  TKSDVWSLGVILYILLSCYPPFIAONNRQKCQMIINGNFSEYEKKVKGISQPAKNLISSLITVDRSKRPSALELLSDPWV: 306
PsCCaMK     235:  TKSDVWSLGVILYILLSCYPPFIAONNRQKCQMIINGNFSEYEKKVKGISQSAKNLISSLITVDPAKRPSAQELLSDPWV: 314
NtCCaMK     220:  TKSDIWSLGVILYILLCYPPFIAPSNRKKCQMILNGQFSFDEKKAKNIISSAKDLISSLKVLDNMRPTAQELLEHPWV: 299
LlCCaMK     223:  SASDVWSLGVILYILLCCPPFHAPSVHKTLAGDRSFEEKKTLTSSAKDLISSLISVDPYKRPTANDLLKHPWV: 302
OsCCaMK     219:  AASDVWSLGVILYILLCCPPFHAATNREKCQRILSGEESYQDHKAKTISSAKDLISRLLSVQPYKRPTASDLLRHPWV: 298
Physc.CCaMK 208:  PANDWWSLGVILYILLCGYPPFRARSSRDKQMQLLTGSYSMEEEXARGISHEAKQLIRRLISVDRFAREPARELLSHPWV: 287
                                                                                        *

• • • 330 • • • 340 • • • 350 • • • 360 • • • 370 • • • 380 • • • 390 • • • 400
LjCCaMK     301:  RQDKRKDEQMDPEIVSRLQSENARRKLRAATASVWSSTTFPLRTKKRSIVGTYDLKEEBIESRLRIHKKTCGNGDNAITL: 380
MtCCaMK     307:  KGEKRKDVQMDPEIVSRLQSENARRKLRAATASVWSSTTFPLRTKKISIVGSYDLKEEBIENRMHEKKICADRDNATL: 386
PsCCaMK     315:  KGEKRKDDQMDPEIVSRLQRFNARRKLRAATASVWSSTTFPLRTKKISIVGSYDLKEEBIENRMHEKKICADRDNATL: 394
NtCCaMK     300:  TCDLAKQEQMDAEIVSRLQSENRRKFRAAAMAGVLSSSFSLRTKKLKKIGSYDLKPEEIQNLSHNRKICKNGENSTL: 379
LlCCaMK     303:  IGDSAKQELTEPEVVSRLRSFNARRKLRATAIASVSSKVLLRTKKLRNLLGSHDMKSELAIHRAHEKRICANGDNATL: 382
OsCCaMK     299:  IGDCAKQDLMDARVVSKLQKFNARRKLRAAIASVLSCKVALRTKRRLCTHDLTSEEDNRLHEGRICADGENATL: 378
Physc.CCaMK 288:  SGDIANRDLLHKQVFMRLQHENARRKFRATAYASIVRTKFLLRTRYLKEHLGDRVLTDSBLEALRVNEMRISSNGQTATL: 367

• • • 410 • • • 420 • • • 430 • • • 440 • • • 450 • • • 460 • • • 470 • • • 480
LjCCaMK     381:  SLEVEVLKAMKMPSLIPLAPPTEDLFDMRDCTIDMRETLCGRSIKNSKGDDALRLCQMYDTDRSCCITKRDVASMLC: 460
MtCCaMK     387:  SEREEVLKAMNMLSLIPLASRTELFDNRDGTIDMRETLCGSSIKNSKGEDALRLCEQMYDTDRSGCIKKDVASMLR: 466
PsCCaMK     395:  CEREEVLKAMNMLSLIPLPAARTEDLFDMRDCTIDMRETLCGSSIKNSKGEDALRLCQARD..RSCCINKKDVASMLR: 472
NtCCaMK     380:  LEREEVLKAMEMSLVPLAPPTEDLFDMRDCTIDMRETLCGRSSIKYSGGDDALRLCQMYDTDRSCCIKKDVASMLR: 459
LlCCaMK     383:  PEREEVLKAMKMNSLIPLAPPRIEDLFDMRDCTIDMRETLCGLSNIRNSQGDDALQLCQMYDADRSCCIKKDVASMLR: 462
OsCCaMK     379:  SEREEGVLRAMKMDSLIPLAPPRVEDLFDMRDCTIDMRETLCGPSLRNSEGDDALRLCQMYDARSCCIKKDVASMLR: 458
Physc.CCaMK 368:  KEREEVLRSINLHCFVELPPRTEDLFDYLHDCGILLRDVVCGRSLLRTSHLDDALQVCEKIYLRDDSCYLSKGDLARVLG: 447
```

TABLE 3 -continued

Multiple alignment of 'gain of function' snf1 CCaMK protein sequences

```
              · · · 490 · · · 500 · · · 510 · · · 520 · · · 530 · · · ·
LjCCaMK   461: ALPEECLEADITEPGKLDEIEDLMDANSDGKVTFEEKAMMQRDSSLQDMLLSSLRPS: 518
MtCCaMK   467: ALPYDCLPTBITEPGKLDEIEDLMDANNDGKVTFDEEKAMQRDSSLQDVVLSSIRP.: 523
PsCCaMK   473: ALPYDCLPTBITEPGKLDEIEDLMDANSDGKVTFDEEKAMQRDSSLQ.........: 520
NtCCaMK   460: ALPEDCLPINITEPGKLDEIEDLMDANSDCKVTFDEEKAMQRDSSLQDVVLSSLRPS: 517
LlCCaMK   463: ALPEDCVEADITEPGKLDEIEDQMDANSDGKVTFDEEKAMQRDSSLQDVVLSSLRTI: 520
OsCCaMK   459: ALPEECLPGDITEPGKLDEVEDQMDADSDGKVTFDEEKAMMKDSALQDVLLSSLRPQ: 516
Physc.CCaMK 448: ALPEDYLEADISQ.VQMDDIEBHVETDSDGRISYQEERRELSLQDAVMNHFRMEGQVQ: 504
```

X at the position indicated by * is any amino acid other than T or S

TABLE 4

Structural domains of Lotus CCaMK.

```
MGYDQTRKLSDEYEISEILGRGGFSVVRKGTKKSGNEKTQVAIKTLRRLGSSPSGTGGGQ
                 I                      II                        k
KSTATVMGFPSLRQVSVSDALLTNEILVMRRIVENVSPHPNVIDLYDVCEDSNGVHLVLE    i
              III                     IV                        n
LCSGGELFDRIVAQDKYAETEAAAVVRQIAAGLEAVHKADIVHRDLKPENCLFLDSRKDS    a
                                         VI                     s
PLKIMDFGLSSVEEFTDPVVGLFGSIDYVSPEALSQGKITAKSDMWSLGVILYILLSGYPPFIA e
        VII             VIII             IX
QNNRQKQQMIINGNFSFYEKTWKGITQSAKQLISSLLTVDPSKRPSAQELLSHPWVRGDK autophosphorylation site:*

AKDEQMDPEIVSRLQS
FNARRKLRAAAIASV                        autoinhibition F and calmodulin binding domain
WSSTIFLRTKKLRSLVGTYDLKEEEIE
SLRIHFKKICGNGDNATLSEFVEVLKAMKMPSLI     (EF-hand?)
PLAPRIFDLFDNNRDGTIDMREILCGFSSLKNSKGDD  EF-hand
ALRLCFQMYDTDRSGCTTKEEVASMLCALPEECLPADITEPG  EF-hand
KLDEIFDLMDANSDGKVTFEEFKAAMQ            EF-hand
RDSSLQMLLSLLRPS
```

The structural and functional domains in Lotus CCaMK (Table 4) and its snf1-5g mutant, that are common to this CCaMK group of chimeric serine-threonine protein kinases include: a putative bipartite nuclear localization sequence located between amino acids 28-48 of the N-terminus, followed by a kinase domain of 300 amino acids, a putative calmodulin-binding domain between amino acid residues 321 to 335, and finally three visinin-like EF hands motifs between amino acid residues 397 and the C-terminus. A fourth EF hand motif is predicted between amino acid residue 363 and 396. No direct homolog/ortholog is found in Arabidopsis, which appears to lack a gene encoding a chimeric CCaMK protein. Lotus snf1-5g CCaMK shares the following amino acid sequence identity with its CCaMK homologues: 72% with rice (AAT77292.1; SEQ ID NO:14), 73% with lily (AAC49008.1; SEQ ID NO:11), 83% with pea (AAS55544.1; SEQ ID NO:8) and 86% with M. truncatula (AAS75146, SEQ ID NO:7).

The mutant CCaMK, encoded by the 'gain of function' snf1-5g gene, has a hydrophobic isoleucine$^{265}$ in substitution for the hydrophilic threonine$^{265}$ in wild type CCaMK encoded by Lotus Snf1. A threonine residue at the corresponding position in lily CCaMK protein is attributed to be the site for autophosphorylation-dependent activation of this chimeric CCaMK. Interaction of Ca$^{2+}$ with the C-terminal EF hands of Lily CCaMK results in autophosphorylation of this threonine residue, leading to increased affinity for calmodulin. Subsequent binding of Ca$^{2+}$/CaM to CCaMK displaces the autoinhibitory domain from the active site allowing substrate level phosphorylation, which in turn leads to fast time-dependent loss of enzyme activity. It is predicted that this family of chimeric CCaMK recognise and decode the calcium spiking oscillations in the symbiotic signal transduction pathway, whereby calcium sensing leads to activation from a ground state and subsequent inhibition (Lévy et al., 2004 supra).

A plant having a 'gain of function' snf1 genotype, is one that expresses a mutant CCaMK gene, which encodes a CCaMK in which the amino acid residue, corresponding to T$^{265}$ in wild-type Lotus Snf1 CCaMK, is substituted by isoleucine, or any other amino acid other than threonine or serine or deleted, and whose functional activity is modified, facilitating both spontaneous nodulation and Rhizobium nodulation of homozygous 'gain of function' snf1 plants.

Example 6

Complementation Identifies the Mutant Alleles of Snf1

Complementation tests with snf1 mutants of Lotus japonicus, described below, demonstrate that snf1-2 and snf1-5g mutants are allelic to the wild type Snf1 gene. Complementation analyses were performed with a gene cassette comprising the wild type or mutant Snf1 genes (10 kb DNA sequence; Table 5), consisting of a 3.1 kb promoter region, a coding sequence, and a 1.3 kb downstream 3' region of the respective Snf1 gene. The wild type or mutant Snf1 gene cassettes were cloned into a vector (pIV10), and the vector was recombined into the T-DNA of Agrobacterium rhizogenes strain AR12 and AR1193 by triparental mating. Agrobacterium rhizogenes-mediated transformation was then used to transform the wild type and mutant Snf1 gene cassettes into snf1 mutant plants, employing a standard protocol (Stougaard 1995, Methods in Molecular Biology Vol. 49, Plant Gene Transfer and Expression Protocols, p 49-63). In parallel control tests, snf1 mutant plants were transformed with Agrobacterium rhizogenes comprising an empty T-DNA vector lacking a Snf1 gene. The nodulation phenotype of the transgenic hairy root tissue of the transformed Lotus plants was scored after inoculation with Mesorhizobium loti (M. loti).

TABLE 5

Replacement strategy for transgene cassettes for Snf1

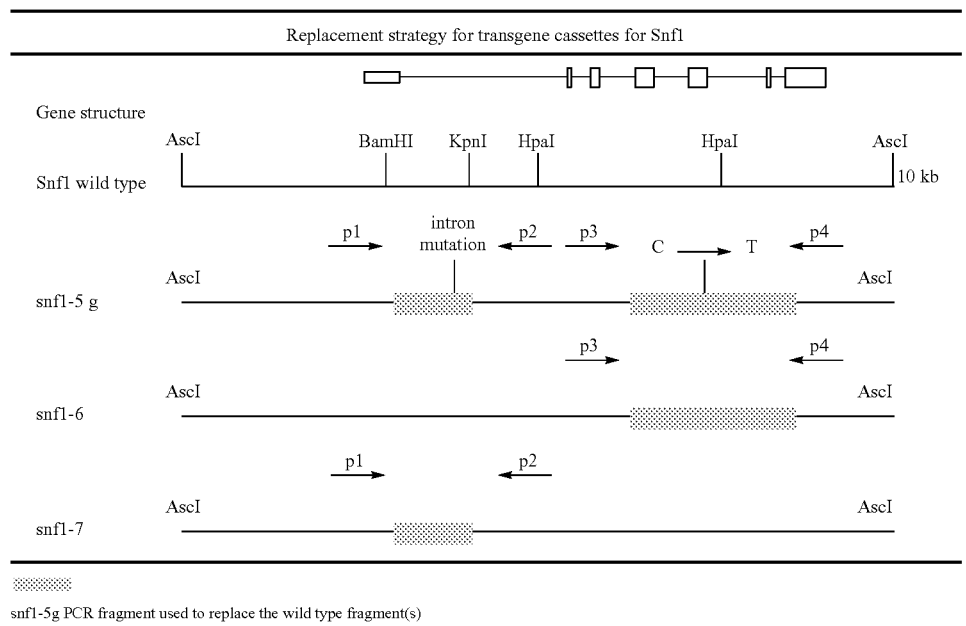

snf1-5g PCR fragment used to replace the wild type fragment(s)

The snf1-2 mutant was complemented for rhizobial nodulation with high efficiency by the wild type Snf1 gene and the snf1-5g gene (Table 6a), demonstrating that the "loss of function" snf1-2 non-nodulation mutant gene is an allele of the Snf1 gene and the snf1-5g gene.

TABLE 6

The snf1-5g transgene confers spontaneous nodulation

| Construct | Total plants | noduled | % nodulation | Nodule number/ plant | Nodule number/ nodulated plant |
|---|---|---|---|---|---|
| a. Complementation of snf1-2 mutants in presence of *Rhizobium* ||||||
| AR12 control | 79 | 0 | 0 | 0 | 0 |
| wild type Snf1 | 28 | 19 | 67.85 | 4.82 | 7.1 |
| snf1-5g allele | 60 | 52 | 86.66 | 3.8 | 4.38 |
| snf1-6 T/I265 allele | 23 | 13 | 56.52 | 2.86 | 5.07 |
| snf1-7 intron allele | 54 | 37 | 68.51 | 4.03 | 6.13 |
| b. Complementation of snf1-2 mutants in absence of *Rhizobium* ||||||
| AR12 control | 37 | 0 | 0 | 0 | 0 |
| wild type Snf1 | 67 | 0 | 0 | 0 | 0 |
| snf1-5g allele | 91 | 10 | 10.98 | 0.25 | 2.3 |
| snf1-6 T/I265 allele | 77 | 18 | 23.37 | 0.4 | 1.72 |
| snf1-7 intron allele | 32 | 0 | 0 | 0 | 0 |
| c. Complementation of snf1-5g mutants in absence of *Rhizobium* ||||||
| AR12 control | 15 | 10 | 66.66 | 3.26 | 4.45 |
| wild type Snf1 | 49 | 19 | 38.77 | 1.53 | 4.16 |
| snf1-5g allele | 64 | 53 | 82.81 | 3.6 | 4.35 |
| snf1-7 intron allele | 43 | 16 | 37.2 | 0.62 | 1.68 |
| d. Complementation of snf1-5g mutants in presence of *Rhizobium* ||||||
| AR12 control | 21 | 12 | 57.14 | 1.76 | 3.08 |
| wild type Snf1 | 30 | 18 | 60 | 2.86 | 4.77 |
| snf1-5g allele | 31 | 21 | 67.74 | 1.38 | 2.09 |
| snf1-7 intron allele | 33 | 25 | 75.75 | 2.06 | 2.72 |

Example 7

The snf1-5g Transgene Confers Spontaneous Nodulation and Rhizobial-Induced Nodulation on a Nodulation-Deficient *Lotus* Plant The snf1-5g allele has two point mutations with respect to Snf1. Alleles of snf1-5g having either the T/I265 substitution (snf1-6) or the intron mutation (snf1-7) were constructed by restriction fragment replacement. Transgenic expression of each allele revealed that snf1-6, with the T/I265 substitution confers the 'gain of function' spontaneous nodulation phenotype (Table 6).

The wild type Snf1 gene is cloned on a 10 kb AscI-AscI fragment (wild type Snf1 gene cassette), of which a 6485 bp region comprising the gene is sequenced (SEQ ID NO: 1). The mutations in snf1-5g are at position 1320 (intron mutation; snf1-7) located within a BamHI-KpnI fragment (positions 933-1991) and position 3637 (T/I265 substitution; snf1-6) located within an HpaI fragment (positions 2621-5162). snf gene cassettes comprising the snf1-5g, snf1-6, and snf1-7 alleles were constructed as follows:

Construction of snf1-6 (SEQ ID NO: 16): The fragment between the two HpaI sites was PCR amplified from snf1-5g mutant DNA using primer p3+p4 (see below) using proofreading Taq polymerase. The resulting fragment was cloned, sequence-confirmed and used to replace the HpaI fragment in the wild type Snf1 gene cassette by conventional cloning methods.

Construction of snf1-7 (SEQ ID NO: 19): The fragment between the BamHI and KpnI sites was PCR amplified from snf1-5g mutant DNA using primers p1+p2 (see below) using proofreading Taq polymerase. The resulting fragment was cloned, sequence-confirmed and used to replace the BamHI-KpnI fragment in the wild type Snf1 gene cassette using conventional cloning methods.

Construction of the snf1-5g: The fragment between the two HpaI sites was PCR amplified from snf1-5g mutant DNA using primer p3+p4 using proofreading Taq polymerase. The resulting fragment was cloned, sequence-confirmed and used to replace the HpaI fragment in the snf1-7 gene cassette using conventional cloning techniques.

Primers for construction of snf1-6 and snf1-7:

```
                                       (SEQ ID NO: 22)
p1:    5'-GGTTGTTTGGATCCATTGATTATGTTTCAC-3'

(SEQ ID NO: 23)
p2:    5'-CATGGGTACCCGATCCGATTTGAC-3'

(SEQ ID NO: 24)
p3:    5'-GCGACCCTTCATATATTGTGTCT-3'

(SEQ ID NO: 25)
p4:    5'-GTGTTCATGGATATGTTTGAGTAAATAG-3'
```

The gene cassettes were transferred to binary vectors as AscI fragments, and transformed into snf1-2 and snf1-5g mutant *Lotus* plants by *Agrobacterium*-mediated transformation, employing *A. rhizogenes* for hairy root transformation.

Only snf1-5g (both mutations) and the snf1-6 (T/I$^{265}$) transgene cassettes conferred a spontaneous nodulation phenotype on transgenic roots of snf1-2 mutants, in contrast to snf1-7 (single nucleotide change in intron 1) or the wild type transgene cassettes (Table 6b). However, all three constructs complemented snf1-2 mutants for rhizobial nodulation, demonstrating that they each encode a functional CCaMK protein (Table 6a). This differential response illustrates the effect of the amino acid substitution and confirms that spontaneous nodulation is caused by a change in CCaMK protein properties. This conclusion is further supported by the opposite effect of wild type Snf1 and snf1-5g transgene expression in transgenic roots of snf1-5g mutants (Table 6c). Both the wild type allele and the intron 1 allele suppress spontaneous nodulation (Table 6c) while rhizobial nodulation occurs with normal frequency (Table 6d).

Example 8

The snf1-5g Gene Confers Spontaneous Nodulation on *Lotus* Mutants Deficient in nod Factor Perception Spontaneous nodule formation is independent of *Rhizobium*-induction and exogenous Nod-factor signalling, and hence independent of functional Nod-factor receptors. These properties were demonstrated in double mutant *Lotus* plants comprising both the snf1-5 and nfr1-1 mutations that were generated by traditional crossing. In nfr1-1 mutants the earliest electrophysiological responses to Nod-factor are perturbed, there is no Ca$^{2+}$ spiking, no visible root hair deformation and no initiation of nodule primordia after inoculation with *Rhizobium*. Expression of the snf1-5 gene in nfr1-1 non-functional receptor mutant background was shown to confer the ability to form spontaneous nodules, despite the lack of nod-factor perception. When grown in the absence of *Rhizobium*, nfr1-1/snf1-5g double mutants form root nodules spontaneously, which are indistinguishable from spontaneous nodules developed in snf1-5g mutants.

Example 9

Spontaneous Nodules Formed in Plants Expressing 'Gain of Function' snf1-5g Gene can Establish Nitrogen-Fixing Endosymbiosis

*Lotus* mutants lacking a functional nod-factor receptor called nfr1, are blocked at the first step of *Rhizobium* nodule formation, characterised by an inability to respond to *Rhizobium* or nod factors (no root hair deformation, no branching and no calcium spiking). However, the snf1-5g gene not only confers the ability to form spontaneous nodules to the nfr1/snf1-5g double mutant, but also confers the ability to fix nitrogen when the plants are inoculated with *Mesorhizobium loti* strain NZP2235. As shown in FIGS. 5A, 5B, 5C and 5D, nfr1-1snf1-1 mutants inoculated with *Mesorhizbium loti* form spontaneous nodules, some of which turn pink five weeks post-inoculation indicating the presence of leghemoglobin (the pink nodules appear dark grey in (A), (B), (C) and (D) as indicated).

Figure 5:
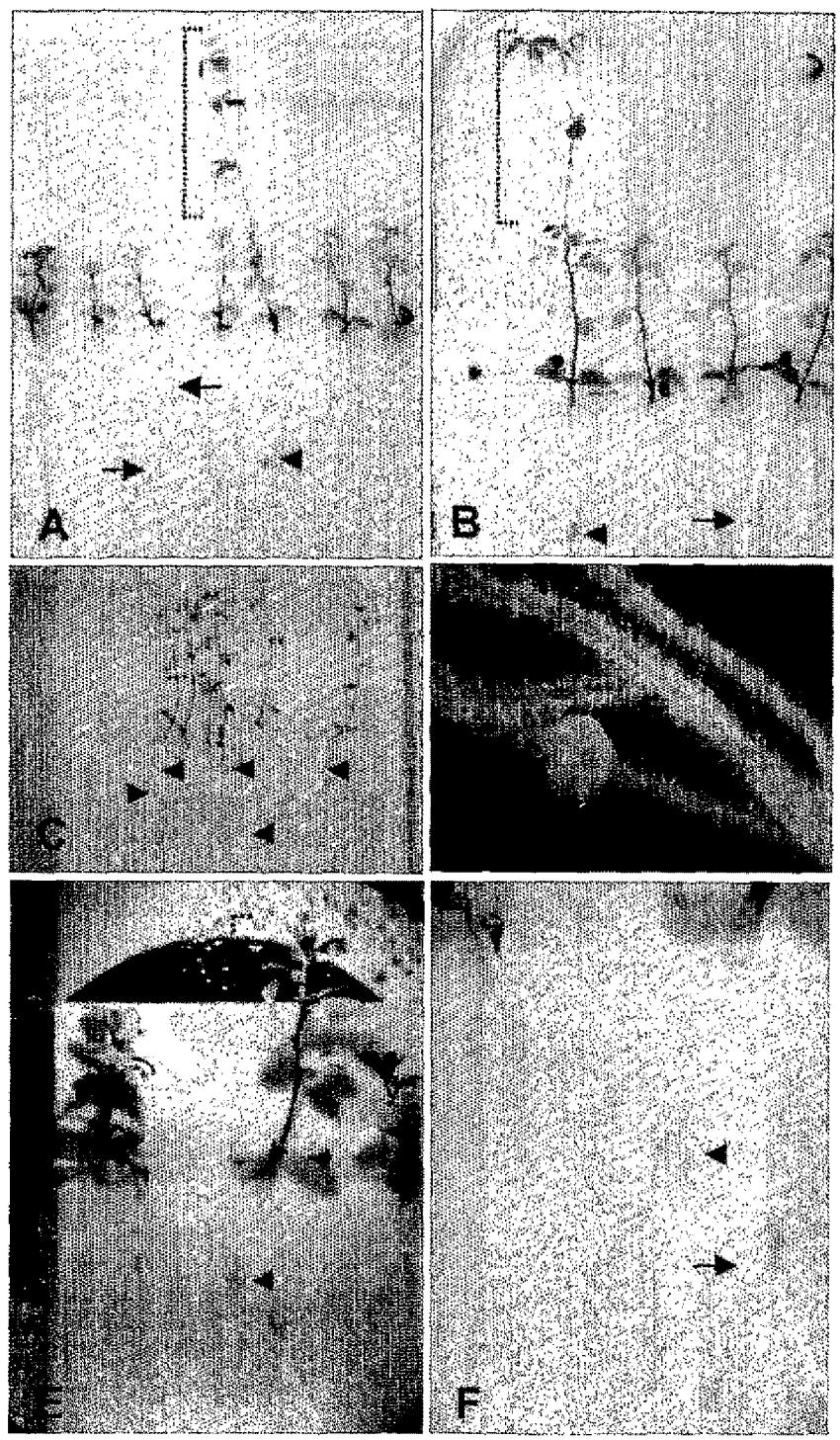
FIG. 5: Characterisation of nfr1-1/snf1-5g double mutant plants inoculated with *M. loti* or *M. loti* nodC::Tn5.

When nfr1 mutants or un-inoculated nfr1/snf1-5g double mutant plants are grown in nitrogen-deficient conditions they display typical nitrogen starvation symptoms (short shoot, yellow leaves). However, when the double nfr1/snf1 mutant plants are inoculated with *M. loti* and form functional nodules, they develop dark-green leaves and longer shoots, indicative of nitrogen fixation (FIGS. 5A, B and C).

The formation of functional nodules on nfr1-1/snf1-5g double mutants can also occur with mutant *M. loti* bacteria that are unable to produce nod factors. *M. loti* nodC::Tn5 mutant is impaired in Nod factor synthesis and carries a neomycin resistance gene as a marker. Inoculation of the nfr1-1/snf1-5g double mutants with *M. loti* nodC::Tn5 produces infected pink nodules (FIGS. 5E and 5F, where the pink nodules appear darker grey), while inoculation of wild-type *Lotus* plants with *M. loti* nodC::Tn5 fails to result in nodulation. The *M. loti* nodC::Tn5 infected nodules, formed on nfr1-1/snf1-5g double mutants, were surface sterilised, crushed and the resulting suspension was plated on neomycin-containing media in order to propagate the neomycin-resistant bacteria from the infected nodules. When the bacteria recovered from the neomycin containing plates was used to inoculate wild type plants they failed to form nodules, while inoculated nfr1-1/snf1-5g plants formed spontaneous nodules which were invaded and turned pink. These data demonstrate that both spontaneous nodulation and the formation of functional nodules in Lotus plants under the control of the snf1-5g gene is neither dependent on nod factor production by the cognate infecting rhizobial strain nor detection of nod factors by the inoculated host plant.

An acetylene reduction assay was used to demonstrate and quantify nitrogenase activity and nitrogen-fixation by double mutant nfr1/snf1 plants. Nitrogen fixation converts molecular N$_2$ into NH$_3$ via a series of ATP-dependent enzymatic steps (Turner and Gibson, 1980, "Measurements of Nitrogen fixation by Indirect Means" in "Methods for Evaluating Biological Nitrogen Fixation" Edited by F. J. Bergersen 1980, Publisher: John Wiley & Sons Ltd). Although molecular nitrogen is the natural substrate for nitrogenase, other triple-bonded nitrogen analogues such as acetylene (HC≡CH) can be reduced by the nitrogenase complex. Acetylene is reduced to ethylene according the following reaction:

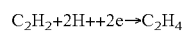

According to the assay procedure, entire plants were exposed to 6% acetylene in air mixture in a suitable airtight glass container and incubated at 25° C. After 4 and 28 hours incubation, air samples were withdrawn and the amount of ethylene produced was determined by gas chromatography (FIG. 6A, B).

After 4 and 28 hours of incubation, the difference in detectable ethylene between the double mutant nfr1/snf1-5g, inoculated with *Rhizobium*, and control un-inoculated nfr1/snf-5g plants, was highly significant. Although the amount of ethylene produced in inoculated wild type plants was higher than the double mutant nfr1/snf1-5g at 4 hours, after 28 hours the level of ethylene in the wild type had declined, while the level of ethylene in the double mutant nfr1/snf1-5g had increased. These data demonstrate that spontaneously nodulated snf1-5g plants are capable of establishing an efficient nitrogen-fixing capacity following inoculation with *Rhizobium*, suggesting that *Rhizobium* can establish *Rhizobial* endosymbiosis within spontaneously formed nodules.

Example 10

Infection Pathway of Spontaneous Nodulation in a snf1-5g *Lotus* Plant

The *Lotus* nfr1/snf1-5g double mutant lacks the nod factor receptor and thus the nitrogen-fixing ability of these plants cannot be attributed to *Rhizobium*-nodulation via the root hair and infection thread pathway, characteristic of wild type nodulation.

The mechanism of bacterial invasion of the spontaneous nodules of nf1-1/snf1-5g double mutants was examined in mutant plants infected with a *M. loti* strain transformed with a GFP reporter gene. The location of this bacterial strain in infected tissue can be detected by virtue of their green fluorescence.

The roots of wild type and nfr1-1/snf1-5g double mutant plants were screened for infection threads and fluorescent bacteria by confocal microscopy at different time points, from one to five weeks post-inoculation. In the wild type plants, infection threads were formed one week post inoculation, but at no stage could infection threads be detected in the roots of the double mutant. However, a massive accumulation of fluorescent bacteria was observed on the side surfaces of their spontaneous nodules (FIGS. 7A and 7B, indicated by arrows) which were also invaded, as shown by fluorescent bacteria inside the nodule (FIGS. 7C and 7D). The green fluorescence appears grey in FIGS. 7A, B, C, and D. This suggests an infection process similar to that observed in the tropical legume *Sesbania rostrata* where the bacteria penetrate the intercellular spaces via the so-called fissure- or crack-entry made by the emerging nodule (Tsien et al., 1983, *Journal of Bacteriology*, 156: 888-897; Ndoye et al., 1994, *Journal of Bacteriology*, 176: 1060-1068).

This infection process was analysed further in *Lotus* nfr1-1snf1-5g double mutants inoculated with *M. loti* strain 2235 transformed with a hemA::lacZ fusion gene. Serial thin sections of nodules from the infected plants were stained for the lacZ activity (FIGS. 8A and 8B), which demonstrated the presence of *M. loti* inside the nodule in a manner comparable to rhizobial-induced nodules in wild type plants. The serial thin sections of the nfr1-1snf1-1 nodules further revealed the presence of "bridge like" structures between the cortical cells inside the invaded nodule (FIGS. 8C and 8D). These structures resemble the infection pockets reported for *Sesbania rostrata* (Tsien et al., 1983; Ndoye et al., 1994). Intercellular invaginations which may facilitate the penetration of bacteria in the cells are seen in FIGS. 8E and 8F.

The invention claimed is:

1. A genetically modified and non-naturally occurring plant comprising a nucleotide sequence encoding a modified Calcium and Calmodulin-dependent protein kinase (CCaMK) polypeptide which is autophosphorylation deficient and having at least 85% sequence identity to an amino acid sequence selected from the group consisting of SEQ ID NO: 7, SEQ ID NO: 8, SEQ ID NO: 9, SEQ ID NO: 10, SEQ ID NO: 11, SEQ ID NO: 15, SEQ ID NO: 26, and SEQ ID NO: 27; wherein amino acid residue designated as Xaa in said amino acid sequence is at an autophosphorylation site in a native and unmodified CCaMK polypeptide; wherein said modified CCaMK is autophosphorylation-deficient at the amino acid residue corresponding to said Xaa; wherein said Xaa is selected from the group consisting of isoleucine, leucine, valine, methionine, alanine, phenylalanine, tyrosine, tryptophan, arginine, lysine, glycine, histidine, aspartate, asparagine, glutamate, glutamine, proline, and cysteine; and wherein expression of said modified CCaMK polypeptide in said genetically modified plant results in spontaneous nodule formation which is independent of *Rhizobium*-induction and exogenous Nod-factor signalling in said plant.

2. The genetically modified plant of claim 1, wherein the encoded polypeptide has at least 90% sequence identity to an amino acid sequence selected from the group consisting of SEQ ID NO: 7, SEQ ID NO: 8, SEQ ID NO: 9, SEQ ID NO: 10, SEQ ID NO: 11, SEQ ID NO: 15, SEQ ID NO: 26, and SEQ ID NO: 27.

3. The genetically modified plant of claim 1, wherein Xaa of said amino acid sequence is selected from the group consisting of isoleucine, leucine, valine, glycine, and alanine.

4. The genetically modified plant of claim 1, wherein Xaa of said amino acid sequence is isoleucine.

5. The genetically modified plant of claim 1, wherein the modified CCaMK polypeptide is encoded by a mutated nucleic acid molecule having a nucleotide sequence selected from the group consisting of SEQ ID NO: 4 and SEQ ID NO: 5.

6. A method for producing a genetically modified and non-naturally occurring plant having spontaneous nodule formation which is independent of *Rhizobium*-induction and exogenous Nod-factor signalling, the method comprising the steps of:
a) mutating a plant's genome;
b) obtaining progeny of mutated plants from the mutated plant of step a); and
c) selecting a mutant plant from the progeny of mutated plants of step b) that expresses a nucleotide sequence encoding a modified Calcium and Calmodulin-dependent protein kinase (CCaMK) polypeptide which is autophosphorylation deficient and having at least 85% sequence identity to an amino acid sequence selected from the group consisting of SEQ ID NO: 7, SEQ ID NO: 8, SEQ ID NO: 9, SEQ ID NO: 10, SEQ ID NO: 11, SEQ ID NO: 15, SEQ ID NO: 26, and SEQ ID NO: 27; wherein amino acid residue designated as Xaa in said amino acid sequence is at an autophosphorylation site in a native and unmodified CCaMK polypeptide; wherein said modified CCaMK is autophosphorylation-deficient at the amino acid residue corresponding to said Xaa; wherein said Xaa is selected from the group consisting of isoleucine, leucine, valine, methionine, alanine, phenylalanine, tyrosine, tryptophan, arginine, lysine, glycine, histidine, aspartate, asparagine, glutamate, glutamine, proline, and cysteine; and wherein expression of said modified CCaMK polypeptide in said genetically modified plant results in spontaneous nodule formation which is independent of *Rhizobium*-induction and exogenous Nod-factor signalling in said selected mutant plant.

7. The method of claim 6, wherein Xaa of said amino acid sequence is selected from the group consisting of isoleucine, leucine, valine, alanine, and glycine.

8. The method of claim 6, wherein Xaa of said amino acid sequence is isoleucine.

9. The genetically modified plant of claim 1, further comprising a homologous promoter nucleotide sequence operably linked to the nucleotide sequence encoding the modified CCaMK polypeptide.

10. The genetically modified plant of claim 1, further comprising a heterologous promoter nucleotide sequence operably linked to the nucleotide sequence encoding the modified CCaMK polypeptide.

11. The genetically modified plant of claim 10, wherein said promoter is a constitutive promoter.

12. The genetically modified plant of claim 1, wherein said plant is a monocotyledonous plant.

13. The genetically modified plant of claim 1, wherein said plant is a dicotyledonous plant.

14. The genetically modified plant of claim 12, wherein said plant is selected from the group consisting of rice, barley, maize, oats, rye, sorghum, wheat, and Poaceae grass.

15. The method of claim 6, wherein said mutating a plant's genome comprises introducing into said plant's genome a gene cassette comprising said nucleotide sequence encoding said modified CCaMK polypeptide and selecting a transgenic plant or progeny comprising said gene cassette and expressing said modified CCaMK polypeptide.

16. The method of claim 15, wherein the gene cassette is introduced into the plant by transformation.

17. The method of claim 15, wherein the gene cassette is introduced into the plant by sexual crossing with a transgenic plant comprising said gene cassette.

18. A genetically modified plant produced by the method of claim 15, wherein said plant comprises said gene cassette.

19. A seed of the genetically modified plant of claim 1, wherein said seed comprises said nucleotide sequence encoding said modified CCaMK polypeptide.

20. A crop comprising the genetically modified plant of claim 1.

21. A seed of the genetically modified plant of claim 2, wherein said seed comprises said nucleotide sequence encoding said modified CCaMK polypeptide.

22. A progeny plant produced from the genetically modified plant of claim 1, wherein said progeny plant comprises said nucleotide sequence encoding said modified CCaMK polypeptide.

23. The genetically modified plant of claim 1, wherein the encoded polypeptide has the amino acid sequence of SEQ ID NO: 7.

24. The genetically modified plant of claim 1, wherein the encoded polypeptide has the amino acid sequence of SEQ ID NO: 8.

25. The genetically modified plant of claim 1, wherein the encoded polypeptide has the amino acid sequence of SEQ ID NO: 9.

26. The genetically modified plant of claim 1, wherein the encoded polypeptide has the amino acid sequence of SEQ ID NO: 10.

27. The genetically modified plant of claim 1, wherein the encoded polypeptide has the amino acid sequence of SEQ ID NO: 11.

28. The genetically modified plant of claim 1, wherein the encoded polypeptide has the amino acid sequence of SEQ ID NO: 15.

29. The genetically modified plant of claim 1, wherein the encoded polypeptide has the amino acid sequence of SEQ ID NO: 26.

30. The genetically modified plant of claim 1, wherein the encoded polypeptide has the amino acid sequence of SEQ ID NO: 27.

* * * * *

SEQUENCE LISTING

```
<160> NUMBER OF SEQ ID NOS: 27

<210> SEQ ID NO 1
<211> LENGTH: 6485
<212> TYPE: DNA
<213> ORGANISM: Lotus japonicus
<220> FEATURE:
<221> NAME/KEY: 5'UTR
<222> LOCATION: (1)..(323)
<220> FEATURE:
<221> NAME/KEY: exon
<222> LOCATION: (324)..(1036)
<220> FEATURE:
<221> NAME/KEY: Intron
<222> LOCATION: (1037)..(3265)
<220> FEATURE:
<221> NAME/KEY: exon
<222> LOCATION: (3266)..(3320)
<220> FEATURE:
<221> NAME/KEY: Intron
<222> LOCATION: (3321)..(3611)
<220> FEATURE:
<221> NAME/KEY: exon
<222> LOCATION: (3612)..(3722)
<220> FEATURE:
<221> NAME/KEY: Intron
<222> LOCATION: (3723)..(4114)
<220> FEATURE:
<221> NAME/KEY: exon
<222> LOCATION: (4115)..(4347)
<220> FEATURE:
<221> NAME/KEY: Intron
<222> LOCATION: (4348)..(4715)
<220> FEATURE:
<221> NAME/KEY: exon
<222> LOCATION: (4716)..(4923)
<220> FEATURE:
<221> NAME/KEY: Intron
<222> LOCATION: (4924)..(5593)
<220> FEATURE:
<221> NAME/KEY: exon
```

```
<222> LOCATION: (5594)..(5653)
<220> FEATURE:
<221> NAME/KEY: Intron
<222> LOCATION: (5654)..(5737)
<220> FEATURE:
<221> NAME/KEY: exon
<222> LOCATION: (5738)..(5914)

<400> SEQUENCE: 1
ttttcaagtc ggctaaatag tgaatagaag aattttagag tacaaaatgg tagcagttga    60
ctctctctct gtcccttcta aaacagcccc taccagccat tgtttattct cttgtaccta   120
tctgaatttg cttcatattt tatgccataa actaatgcag aaactctcac aaaggctaat   180
gtcaacatca accattttca atacgcgttt tgtaggccga tcattgaaac ttgaagtcat   240
gttatattat acatacctct tctcattgat cattgaacat tttctgagtc tgaaaagatt   300
ccaatatttt caaacactct gcc atg gga tat gat caa acc aga aag ctc tct   353
                         Met Gly Tyr Asp Gln Thr Arg Lys Leu Ser
                          1               5                  10 gat gag tat gag att tca gag att cta gga aga ggt gga ttc tct gtt   401
Asp Glu Tyr Glu Ile Ser Glu Ile Leu Gly Arg Gly Gly Phe Ser Val
            15                  20                  25 gtc aga aaa gga acc aaa aaa tca ggc aat gag aaa acc caa gta gcc   449
Val Arg Lys Gly Thr Lys Lys Ser Gly Asn Glu Lys Thr Gln Val Ala
        30                  35                  40 atc aaa aca ctc aga agg tta ggt agt tct ccc tct ggg aca ggt ggt   497
Ile Lys Thr Leu Arg Arg Leu Gly Ser Ser Pro Ser Gly Thr Gly Gly
    45                  50                  55 gga cag aag agc aca gca act gtg atg ggg ttc cct tct ttg aga cag   545
Gly Gln Lys Ser Thr Ala Thr Val Met Gly Phe Pro Ser Leu Arg Gln
60                  65                  70 gtt tca gtc tca gat gct ttg ctc acc aat gag att ctt gtg atg agg   593
Val Ser Val Ser Asp Ala Leu Leu Thr Asn Glu Ile Leu Val Met Arg
            75                  80                  85                  90 agg ata gtg gaa aac gtt tcg cca cat cca aac gtg att gat ctc tat   641
Arg Ile Val Glu Asn Val Ser Pro His Pro Asn Val Ile Asp Leu Tyr
            95                 100                 105 gat gtg tgt gag gac tca aat ggg gtg cat ctt gtg ctg gag ctt tgt   689
Asp Val Cys Glu Asp Ser Asn Gly Val His Leu Val Leu Glu Leu Cys
        110                 115                 120 tct ggt ggg gag ctg ttt gat agg att gtt gca cag gat aag tat gct   737
Ser Gly Gly Glu Leu Phe Asp Arg Ile Val Ala Gln Asp Lys Tyr Ala
    125                 130                 135 gag acg gaa gct gcc gcg gtg gtt cgc cag att gcg gcg ggg cta gag   785
Glu Thr Glu Ala Ala Ala Val Val Arg Gln Ile Ala Ala Gly Leu Glu
140                 145                 150 gcg gtt cac aag gct gac att gtt cac agg gat ttg aag cct gag aat   833
Ala Val His Lys Ala Asp Ile Val His Arg Asp Leu Lys Pro Glu Asn
155                 160                 165                 170 tgc ctt ttc ttg gat tcc agg aag gac tct cct ctc aag atc atg gac   881
Cys Leu Phe Leu Asp Ser Arg Lys Asp Ser Pro Leu Lys Ile Met Asp
            175                 180                 185 ttt ggg ttg agc tct gtt gag gag ttc act gac cct gtt gtt ggg ttg   929
Phe Gly Leu Ser Ser Val Glu Glu Phe Thr Asp Pro Val Val Gly Leu
        190                 195                 200 ttt gga tcc att gat tat gtt tca cca gag gct ctt tct caa ggg aag   977
Phe Gly Ser Ile Asp Tyr Val Ser Pro Glu Ala Leu Ser Gln Gly Lys
    205                 210                 215 atc act gcc aag agt gac atg tgg tct ctg gga gtg att cta tat atc   1025
Ile Thr Ala Lys Ser Asp Met Trp Ser Leu Gly Val Ile Leu Tyr Ile
220                 225                 230
```

| | |
|---|---|
| ttg ctc tct gg gtatgttgtc tttcacttgt tgaaattgtt catattgtgt<br>Leu Leu Ser Gly<br>235 | 1076 |
| tggttgctcc ccatccacct tttgcagagc ccatttggat acaagcttat tgatgtttat | 1136 |
| tgaagcttat ctactagaaa atgcactaaa taagcttcca caatactctt tggcttgcat | 1196 |
| ccaaacggct acttagtgca gtaaatatgg atgccaagaa ggaaatttta gtttctcact | 1256 |
| tattaggtgg cattagtctt tgaaacttaa aaaaaaaaac ccactgataa catgctcgaa | 1316 |
| aatcattcta caattgatta tgaaaaatta attgttagaa tataatataa aagcattaaa | 1376 |
| gtgacccttta cccaacagct taagcttttg ggattaagtg gttatttgac atggtatcac | 1436 |
| tagggatggc aacgggtagg atcgggcatg ggttttacaa ttaccaaacc caaacccaaa | 1496 |
| tcccagaacc caaacccaaa cccaaacaca aaccccttatg ggcgataaaa tgaaattcat | 1556 |
| gcccaaatcc attgggtttc ggatttaccc gaaactcaaa cccaaacccca ttagttaggt | 1616 |
| agcaactcaa tccagaactt actttcatat aaaagaaaag tgaaattcat ataaagaaaa | 1676 |
| aaaaaacaaa tactattcat catcctcatc catcactaaa gtgagacaac aatagtttaa | 1736 |
| agtttacttt ctcaaacata caaaagtaca attaatcatc aaacactaag aacaaagttt | 1796 |
| ataaatatat atatgtatga gggttttttt gtaatttat gtttcgggta tctttgggtt | 1856 |
| cgggtttggg cggggtatgg gcatgaattt aactaatacc aaaatccaaa ctcataaatg | 1916 |
| gcttcagtaa cgggcaaaac tcaaacccaa acccaaatcc agtcaactcg gattttgccc | 1976 |
| gtcaaatcgg atcgggtacc catgggtttg ggcaaaattt ccatccctag gtatcagagc | 2036 |
| ctctatgacc gagaggtcta gagttcgatc cttgctcccc tcactttcta attaaaaaag | 2096 |
| tggaattttaa ttaagcacat ggtaggtgga cctgtgcatt tatccacgct acaagcccaa | 2156 |
| agggctcttg cgtgaggagg cgtgttagaa tataatataa aaccattaaa gtgaccctta | 2216 |
| cccaacagct taagcttttg ggataagtgg ttgtttgaca ttaatacttg agagaaactt | 2276 |
| atatgaatag cttctgaatg atgttccata attcattttg agaaagaaaa aaagctaatc | 2336 |
| caaacatgtg ttagaaaatg aacatgcttg atcgtgatga aataactttc cttaaagtat | 2396 |
| ttcaagcact ctctaaattt cgtcttagag tttggatgca agaatacccca ggataatcag | 2456 |
| ccttgattcg agtttgcaca agactaatga aaactcgaaa tgaagagaag tgattttctg | 2516 |
| gaaaacagag gatatgattg tgtgttatga attctgaaca tggactctat ttataggcaa | 2576 |
| aacagaacaa tatataaggt tgcgacccctt catatattgt gtctgttaac aacagtcgca | 2636 |
| aaaatcaaat tcaaaaagag caaaaacaaa cggacgttac ggcaaccgcg tagccgtcgt | 2696 |
| tgcgtctaca agccgccact agcgcctcta cgcccacgcc tgtgacaccg gcgaggggtg | 2756 |
| gtgtgagtgg aatatgtgac ataaaagctt gggaccacca aactatgcac atgtggcact | 2816 |
| atatcctctt tttgtctctt tgttgaatgg ttgacattta atgatatata aatgctttga | 2876 |
| aaagttgctc cactttctat gtgagacttc attccaattc attcaatgca aaatcaacac | 2936 |
| acttatcatt ttggaacact aagtaattat tacaacaaca tgttgtaagg gaagtcatca | 2996 |
| cttcattaca tgaaaaataa atgagttatg agttggtctg ggtatcacct caaaattcct | 3056 |
| caaaattggg ggggggggg gggttaagga atgagttttt caataaatct ggtcactcaa | 3116 |
| cttttgcacat tatgctgacc agttgttcct tgcttcatta catatatttc cttgtaggaa | 3176 |
| catcaataga tggaagactt tttagtatttt ctcttaagta atcaaactaa ctcagtatta | 3236 |
| tcctcctatg taacttttttt cttttgcag g tat ccg cct ttc att gca caa aat<br>                                            Tyr Pro Pro Phe Ile Ala Gln Asn<br>                                            240                    245 | 3290 |

```
aat cgc caa aaa caa caa atg ata atc aat gtaagcaaca tctcgcgttg         3340
Asn Arg Gln Lys Gln Gln Met Ile Ile Asn
            250                 255 attaagtgtg tgtgtcttct taggtagaat gagtaatgca ggcagagtca aaattagcaa     3400
tgtaacaaga agtgatatat gttcaaatat attatccaag ttagttcctg ggttttttcc     3460
tttattttag attaatcata gtaacatatc acttttatca caaaattat atagcacgcg      3520 cacacacata cactatattt agatagatat atagacacac catttgcatt ctgtaaaaaa     3580
attgcttacc aaatgaaaca ttttccaaca g ggg aat ttc agt ttc tat gag        3632
                                 Gly Asn Phe Ser Phe Tyr Glu
                                                      260 aag act tgg aag ggc att acc caa tca gcg aag caa ttg att tca agt       3680
Lys Thr Trp Lys Gly Ile Thr Gln Ser Ala Lys Gln Leu Ile Ser Ser
            265                 270                 275 ctt ttg act gtt gat cca agt aag agg cct agt gct caa gag                3722
Leu Leu Thr Val Asp Pro Ser Lys Arg Pro Ser Ala Gln Glu
280                 285                 290 gtatatcaat tgtatattct tactaacttc actaatgtga actaggcagc atatctcatt     3782
ctttactaat aacatggaat gaagtgcatc tcctatgata agagcccttt atagcagaaa     3842
attgccataa aatccaatta catgcattca ttttttttta taaggacatc tgagggaaaa     3902
aaagtacttt ttctaataat attttgctga tcagaaagca tgactaataa tcacttagca     3962
attccacaaa gtagcaatgc ctttgcatct caaatacagt atgcacattt cttcaacatt     4022
ttgcatcata ttattttcag tttcaaggtg ttttattgac ataattaagc acaacaataa     4082
ccccagacac aattctgttg tacttggaac ag ctc ttg agt cat cca tgg gtc       4135
                                    Leu Leu Ser His Pro Trp Val
                                                295             300 aga ggt gac aaa gcc aaa gat gag caa atg gac cct gag att gtc tca       4183
Arg Gly Asp Lys Ala Lys Asp Glu Gln Met Asp Pro Glu Ile Val Ser
            305                 310                 315 agg ctg cag agc ttt aat gca aga cgc aaa ctc cgc gca gct gca att       4231
Arg Leu Gln Ser Phe Asn Ala Arg Arg Lys Leu Arg Ala Ala Ala Ile
            320                 325                 330 gct agt gtt tgg agc agc aca atc ttc ctg aga acc aaa aag ctg aga       4279
Ala Ser Val Trp Ser Ser Thr Ile Phe Leu Arg Thr Lys Lys Leu Arg
            335                 340                 345 tcc ttg gta gga act tat gat ctc aaa gaa gag gaa att gaa agt ctc       4327
Ser Leu Val Gly Thr Tyr Asp Leu Lys Glu Glu Glu Ile Glu Ser Leu
            350                 355                 360 agg ata cac ttt aag aag at  gtaagtactc acaagtctcc aaattaatca          4377
Arg Ile His Phe Lys Lys Ile
365                 370 tagatagtta aattagtccc taaaaattta caatcggtta tcttagtcag tgaatcataa     4437
aaatttacac ttgaagtcct tcaattgtac tttgtagtca tattagtctt tccatcaagt     4497
acttcaggac taatttaacc aagaagacac atatgtagag actacttcga tggacaaaat    4557
gtcaatgtag acatctaaaa taagtttcat tattcaaaga ctaacatcat tgagcttgtg    4617
tttattgagt tgagactgtg ttgacaattt agtacaaata tttctgtgca gcacactagc    4677
atttgacaat tttgactaat tcctgtggtt gctaacag a tgt gga aat gga gac       4731
                                           Cys Gly Asn Gly Asp
                                                           375 aat gca act ctg tct gag ttt gtg gag gtg ctg aaa gca atg aag atg       4779
Asn Ala Thr Leu Ser Glu Phe Val Glu Val Leu Lys Ala Met Lys Met
            380                 385                 390 ccc tca ttg atc cct cta gca ccg cgt ata ttt gac ttg ttt gac aac       4827
Pro Ser Leu Ile Pro Leu Ala Pro Arg Ile Phe Asp Leu Phe Asp Asn
```

```
                      395                  400                    405
aac cgt gat gga aca att gac atg aga gag ata cta tgt ggg ttt tct     4875
Asn Arg Asp Gly Thr Ile Asp Met Arg Glu Ile Leu Cys Gly Phe Ser
    410                 415                 420 agc ctc aag aac tcc aaa gga gat gat gct ctc cgt ttg tgc ttc cag     4923
Ser Leu Lys Asn Ser Lys Gly Asp Asp Ala Leu Arg Leu Cys Phe Gln
425                 430                 435                 440 gtgagtcttt ttaagttccg gtcttggtag agcttatttt ctactataat aagtacttaa   4983
gcagggtttt ggttaagttt ataaaaatag ctcatgacat atataaactc ttttgagctt   5043
aattaacttg tatgaataac catttatact tacatctaag ctcttttgag ctaatttcaa   5103
taagtttctc aaattagatt atgagaatat cattagtgtt tgctgacata attgcttagt   5163
taacctattt actcaaacat atccatgaac acatgcacat agacaagaat gcacacatat   5223
agcagtgact cgtgagagct tcaatagtta catccaagaa tatcaattta tgaagcaaaa   5283
aagaaatatc atatatgaga gaagatagta gtattataag taattacata tttactaaca   5343
caaacttttg tgaaaagat gtggttgtta aatgacaaac aaaaagtttg taattgtaat    5403
tacaattatg ttatatgaat gaatgaatgt tacaattttc accaccctct aagtttcaac   5463
aactctggaa aaagactaca acaaacacaa gacaaagaaa agaaacaacc caaaagcatt   5523
tgatacagta caaagtaaaa gtgttcagca tgatcagcta attttcctca ctgattttct   5583
tggccaacag atg tat gac aca gat aga tca ggg tgc atc acc aag gaa     5632
            Met Tyr Asp Thr Asp Arg Ser Gly Cys Ile Thr Lys Glu
                        445                 450 gaa gta gca tcc atg ctc tgt gtaattaatg caccttcctt tcaattaact        5683
Glu Val Ala Ser Met Leu Cys
455                 460 atagccttat cttgtgactt tcttctttct aacacaaatc aattcactga acag gct     5740
                                                           Ala ttg cca gag gaa tgt ctt cca gct gat atc act gaa cct ggg aaa ttg     5788
Leu Pro Glu Glu Cys Leu Pro Ala Asp Ile Thr Glu Pro Gly Lys Leu
        465                 470                 475 gat gag ata ttt gac tta atg gat gcc aac agt gat gga aaa gtt aca     5836
Asp Glu Ile Phe Asp Leu Met Asp Ala Asn Ser Asp Gly Lys Val Thr
            480                 485                 490 ttt gaa gaa ttc aaa gct gct atg cag aga gat agc tct ctc caa gac     5884
Phe Glu Glu Phe Lys Ala Ala Met Gln Arg Asp Ser Ser Leu Gln Asp
    495                 500                 505 atg ctc ctc tct tct ctt cgt cca tca tag tttttttttt tttccattca       5934
Met Leu Leu Ser Ser Leu Arg Pro Ser
510                 515 tggtgttatg gtctttcaaa ctttgatatt gactacacct tttacgtttc ttttaatctc   5994
ttttggggct atccttctct tgaggtatt catactacat ggaaaagggg tggtaaagag    6054
ggtgaaattg tgtcatctaa cttttgctat gacaactagg aacttttgca ttctcatgta   6114
atactacaac tagcttaaga gagcggctca atgaatgtca aggcttaaaa tgaaatttaa   6174
gaggagattt tttaaattaa ttaaatagtt ttattgaaat tattgtaatt ctatttttta   6234
tattaatctt ttgtagtttg agttaagtta ttaatcattt aacatttctt ttttgaatta   6294
atcatagaat aaaattgtcaa tcaatttaat cacagttgat agttgaggca ctgttgatat  6354
tagataaggc aaataatagt aaagttaatt cattgaatat tgagagggga aaacaaagaa   6414
cggtttataa tcttgatgat aataattttg aaagaatgga ggtagaagat ttcaattgca   6474
atatatgaaa a                                                        6485
```

```
<210> SEQ ID NO 2
<211> LENGTH: 1557
<212> TYPE: DNA
<213> ORGANISM: Lotus japonicus
<220> FEATURE:
<221> NAME/KEY: CDS
<222> LOCATION: (1)..(1557)

<400> SEQUENCE: 2
```

| | | | | | | | | | | | | | | | | |
|---|---|---|---|---|---|---|---|---|---|---|---|---|---|---|---|---|
| atg | gga | tat | gat | caa | acc | aga | aag | ctc | tct | gat | gag | tat | gag | att | tca | 48 |
| Met | Gly | Tyr | Asp | Gln | Thr | Arg | Lys | Leu | Ser | Asp | Glu | Tyr | Glu | Ile | Ser | |
| 1 | | | | 5 | | | | | 10 | | | | | 15 | | |
| gag | att | cta | gga | aga | ggt | gga | ttc | tct | gtt | gtc | aga | aaa | gga | acc | aaa | 96 |
| Glu | Ile | Leu | Gly | Arg | Gly | Gly | Phe | Ser | Val | Val | Arg | Lys | Gly | Thr | Lys | |
| | | | 20 | | | | | 25 | | | | | 30 | | | |
| aaa | tca | ggc | aat | gag | aaa | acc | caa | gta | gcc | atc | aaa | aca | ctc | aga | agg | 144 |
| Lys | Ser | Gly | Asn | Glu | Lys | Thr | Gln | Val | Ala | Ile | Lys | Thr | Leu | Arg | Arg | |
| | | 35 | | | | | 40 | | | | | 45 | | | | |
| tta | ggt | agt | tct | ccc | tct | ggg | aca | ggt | ggt | gga | cag | aag | agc | aca | gca | 192 |
| Leu | Gly | Ser | Ser | Pro | Ser | Gly | Thr | Gly | Gly | Gly | Gln | Lys | Ser | Thr | Ala | |
| | 50 | | | | | 55 | | | | | 60 | | | | | |
| act | gtg | atg | ggg | ttc | cct | tct | ttg | aga | cag | gtt | tca | gtc | tca | gat | gct | 240 |
| Thr | Val | Met | Gly | Phe | Pro | Ser | Leu | Arg | Gln | Val | Ser | Val | Ser | Asp | Ala | |
| 65 | | | | | 70 | | | | | 75 | | | | | 80 | |
| ttg | ctc | acc | aat | gag | att | ctt | gtg | atg | agg | agg | ata | gtg | gaa | aac | gtt | 288 |
| Leu | Leu | Thr | Asn | Glu | Ile | Leu | Val | Met | Arg | Arg | Ile | Val | Glu | Asn | Val | |
| | | | | 85 | | | | | 90 | | | | | 95 | | |
| tcg | cca | cat | cca | aac | gtg | att | gat | ctc | tat | gat | gtg | tgt | gag | gac | tca | 336 |
| Ser | Pro | His | Pro | Asn | Val | Ile | Asp | Leu | Tyr | Asp | Val | Cys | Glu | Asp | Ser | |
| | | | 100 | | | | | 105 | | | | | 110 | | | |
| aat | ggg | gtg | cat | ctt | gtg | ctg | gag | ctt | tgt | tct | ggt | ggg | gag | ctg | ttt | 384 |
| Asn | Gly | Val | His | Leu | Val | Leu | Glu | Leu | Cys | Ser | Gly | Gly | Glu | Leu | Phe | |
| | | 115 | | | | | 120 | | | | | 125 | | | | |
| gat | agg | att | gtt | gca | cag | gat | aag | tat | gct | gag | acg | gaa | gct | gcc | gcg | 432 |
| Asp | Arg | Ile | Val | Ala | Gln | Asp | Lys | Tyr | Ala | Glu | Thr | Glu | Ala | Ala | Ala | |
| | 130 | | | | | 135 | | | | | 140 | | | | | |
| gtg | gtt | cgc | cag | att | gcg | gcg | ggg | cta | gag | gcg | gtt | cac | aag | gct | gac | 480 |
| Val | Val | Arg | Gln | Ile | Ala | Ala | Gly | Leu | Glu | Ala | Val | His | Lys | Ala | Asp | |
| 145 | | | | | 150 | | | | | 155 | | | | | 160 | |
| att | gtt | cac | agg | gat | ttg | aag | cct | gag | aat | tgc | ctt | ttc | ttg | gat | tcc | 528 |
| Ile | Val | His | Arg | Asp | Leu | Lys | Pro | Glu | Asn | Cys | Leu | Phe | Leu | Asp | Ser | |
| | | | | 165 | | | | | 170 | | | | | 175 | | |
| agg | aag | gac | tct | cct | ctc | aag | atc | atg | gac | ttt | ggg | ttg | agc | tct | gtt | 576 |
| Arg | Lys | Asp | Ser | Pro | Leu | Lys | Ile | Met | Asp | Phe | Gly | Leu | Ser | Ser | Val | |
| | | | 180 | | | | | 185 | | | | | 190 | | | |
| gag | gag | ttc | act | gac | cct | gtt | gtt | ggg | ttg | ttt | gga | tcc | att | gat | tat | 624 |
| Glu | Glu | Phe | Thr | Asp | Pro | Val | Val | Gly | Leu | Phe | Gly | Ser | Ile | Asp | Tyr | |
| | | 195 | | | | | 200 | | | | | 205 | | | | |
| gtt | tca | cca | gag | gct | ctt | tct | caa | ggg | aag | atc | act | gcc | aag | agt | gac | 672 |
| Val | Ser | Pro | Glu | Ala | Leu | Ser | Gln | Gly | Lys | Ile | Thr | Ala | Lys | Ser | Asp | |
| | 210 | | | | | 215 | | | | | 220 | | | | | |
| atg | tgg | tct | ctg | gga | gtg | att | cta | tat | atc | ttg | ctc | tct | ggg | tat | ccg | 720 |
| Met | Trp | Ser | Leu | Gly | Val | Ile | Leu | Tyr | Ile | Leu | Leu | Ser | Gly | Tyr | Pro | |
| 225 | | | | | 230 | | | | | 235 | | | | | 240 | |
| cct | ttc | att | gca | caa | aat | aat | cgc | caa | aaa | caa | caa | atg | ata | atc | aat | 768 |
| Pro | Phe | Ile | Ala | Gln | Asn | Asn | Arg | Gln | Lys | Gln | Gln | Met | Ile | Ile | Asn | |
| | | | | 245 | | | | | 250 | | | | | 255 | | |
| ggg | aat | ttc | agt | ttc | tat | gag | aag | act | tgg | aag | ggc | att | acc | caa | tca | 816 |
| Gly | Asn | Phe | Ser | Phe | Tyr | Glu | Lys | Thr | Trp | Lys | Gly | Ile | Thr | Gln | Ser | |
| | | | 260 | | | | | 265 | | | | | 270 | | | |
| gcg | aag | caa | ttg | att | tca | agt | ctt | ttg | act | gtt | gat | cca | agt | aag | agg | 864 |
| Ala | Lys | Gln | Leu | Ile | Ser | Ser | Leu | Leu | Thr | Val | Asp | Pro | Ser | Lys | Arg | |

```
                    275                 280                 285
cct agt gct caa gag ctc ttg agt cat cca tgg gtc aga ggt gac aaa        912
Pro Ser Ala Gln Glu Leu Leu Ser His Pro Trp Val Arg Gly Asp Lys
    290                 295                 300 gcc aaa gat gag caa atg gac cct gag att gtc tca agg ctg cag agc        960
Ala Lys Asp Glu Gln Met Asp Pro Glu Ile Val Ser Arg Leu Gln Ser
305                 310                 315                 320 ttt aat gca aga cgc aaa ctc cgc gca gct gca att gct agt gtt tgg       1008
Phe Asn Ala Arg Arg Lys Leu Arg Ala Ala Ala Ile Ala Ser Val Trp
                325                 330                 335 agc agc aca atc ttc ctg aga acc aaa aag ctg aga tcc ttg gta gga       1056
Ser Ser Thr Ile Phe Leu Arg Thr Lys Lys Leu Arg Ser Leu Val Gly
            340                 345                 350 act tat gat ctc aaa gaa gag gaa att gaa agt ctc agg ata cac ttt       1104
Thr Tyr Asp Leu Lys Glu Glu Glu Ile Glu Ser Leu Arg Ile His Phe
        355                 360                 365 aag aag ata tgt gga aat gga gac aat gca act ctg tct gag ttt gtg       1152
Lys Lys Ile Cys Gly Asn Gly Asp Asn Ala Thr Leu Ser Glu Phe Val
    370                 375                 380 gag gtg ctg aaa gca atg aag atg ccc tca ttg atc cct cta gca ccg       1200
Glu Val Leu Lys Ala Met Lys Met Pro Ser Leu Ile Pro Leu Ala Pro
385                 390                 395                 400 cgt ata ttt gac ttg ttt gac aac aac cgt gat gga aca att gac atg       1248
Arg Ile Phe Asp Leu Phe Asp Asn Asn Arg Asp Gly Thr Ile Asp Met
                405                 410                 415 aga gag ata cta tgt ggg ttt tct agc ctc aag aac tcc aaa gga gat       1296
Arg Glu Ile Leu Cys Gly Phe Ser Ser Leu Lys Asn Ser Lys Gly Asp
            420                 425                 430 gat gct ctc cgt ttg tgc ttc cag atg tat gac aca gat aga tca ggg       1344
Asp Ala Leu Arg Leu Cys Phe Gln Met Tyr Asp Thr Asp Arg Ser Gly
        435                 440                 445 tgc atc acc aag gaa gaa gta gca tcc atg ctc tgt gct ttg cca gag       1392
Cys Ile Thr Lys Glu Glu Val Ala Ser Met Leu Cys Ala Leu Pro Glu
    450                 455                 460 gaa tgt ctt cca gct gat atc act gaa cct ggg aaa ttg gat gag ata       1440
Glu Cys Leu Pro Ala Asp Ile Thr Glu Pro Gly Lys Leu Asp Glu Ile
465                 470                 475                 480 ttt gac tta atg gat gcc aac agt gat gga aaa gtt aca ttt gaa gaa       1488
Phe Asp Leu Met Asp Ala Asn Ser Asp Gly Lys Val Thr Phe Glu Glu
                485                 490                 495 ttc aaa gct gct atg cag aga gat agc tct ctc caa gac atg ctc ctc       1536
Phe Lys Ala Ala Met Gln Arg Asp Ser Ser Leu Gln Asp Met Leu Leu
            500                 505                 510 tct tct ctt cgt cca tca tag                                            1557
Ser Ser Leu Arg Pro Ser
        515

<210> SEQ ID NO 3
<211> LENGTH: 518
<212> TYPE: PRT
<213> ORGANISM: Lotus japonicus

<400> SEQUENCE: 3

Met Gly Tyr Asp Gln Thr Arg Lys Leu Ser Asp Glu Tyr Glu Ile Ser
1               5                   10                  15

Glu Ile Leu Gly Arg Gly Gly Phe Ser Val Val Arg Lys Gly Thr Lys
            20                  25                  30

Lys Ser Gly Asn Glu Lys Thr Gln Val Ala Ile Lys Thr Leu Arg Arg
        35                  40                  45

Leu Gly Ser Ser Pro Ser Gly Thr Gly Gly Gly Gln Lys Ser Thr Ala
```

```
              50                  55                  60
Thr Val Met Gly Phe Pro Ser Leu Arg Gln Val Ser Val Ser Asp Ala
 65                  70                  75                  80

Leu Leu Thr Asn Glu Ile Leu Val Met Arg Arg Ile Val Glu Asn Val
                 85                  90                  95

Ser Pro His Pro Asn Val Ile Asp Leu Tyr Asp Val Cys Glu Asp Ser
                100                 105                 110

Asn Gly Val His Leu Val Leu Glu Leu Cys Ser Gly Gly Glu Leu Phe
                115                 120                 125

Asp Arg Ile Val Ala Gln Asp Lys Tyr Ala Glu Thr Glu Ala Ala Ala
130                 135                 140

Val Val Arg Gln Ile Ala Ala Gly Leu Glu Ala Val His Lys Ala Asp
145                 150                 155                 160

Ile Val His Arg Asp Leu Lys Pro Glu Asn Cys Leu Phe Leu Asp Ser
                165                 170                 175

Arg Lys Asp Ser Pro Leu Lys Ile Met Asp Phe Gly Leu Ser Ser Val
                180                 185                 190

Glu Glu Phe Thr Asp Pro Val Val Gly Leu Phe Gly Ser Ile Asp Tyr
                195                 200                 205

Val Ser Pro Glu Ala Leu Ser Gln Gly Lys Ile Thr Ala Lys Ser Asp
210                 215                 220

Met Trp Ser Leu Gly Val Ile Leu Tyr Ile Leu Ser Gly Tyr Pro
225                 230                 235                 240

Pro Phe Ile Ala Gln Asn Asn Arg Gln Lys Gln Gln Met Ile Ile Asn
                245                 250                 255

Gly Asn Phe Ser Phe Tyr Glu Lys Thr Trp Lys Gly Ile Thr Gln Ser
                260                 265                 270

Ala Lys Gln Leu Ile Ser Ser Leu Leu Thr Val Asp Pro Ser Lys Arg
                275                 280                 285

Pro Ser Ala Gln Glu Leu Leu Ser His Pro Trp Val Arg Gly Asp Lys
                290                 295                 300

Ala Lys Asp Glu Gln Met Asp Pro Glu Ile Val Ser Arg Leu Gln Ser
305                 310                 315                 320

Phe Asn Ala Arg Arg Lys Leu Arg Ala Ala Ile Ala Ser Val Trp
                325                 330                 335

Ser Ser Thr Ile Phe Leu Arg Thr Lys Lys Leu Arg Ser Leu Val Gly
                340                 345                 350

Thr Tyr Asp Leu Lys Glu Glu Ile Glu Ser Leu Arg Ile His Phe
                355                 360                 365

Lys Lys Ile Cys Gly Asn Gly Asp Asn Ala Thr Leu Ser Glu Phe Val
                370                 375                 380

Glu Val Leu Lys Ala Met Lys Met Pro Ser Leu Ile Pro Leu Ala Pro
385                 390                 395                 400

Arg Ile Phe Asp Leu Phe Asp Asn Asn Arg Asp Gly Thr Ile Asp Met
                405                 410                 415

Arg Glu Ile Leu Cys Gly Phe Ser Ser Leu Lys Asn Ser Lys Gly Asp
                420                 425                 430

Asp Ala Leu Arg Leu Cys Phe Gln Met Tyr Asp Thr Asp Arg Ser Gly
                435                 440                 445

Cys Ile Thr Lys Glu Glu Val Ala Ser Met Leu Cys Ala Leu Pro Glu
                450                 455                 460

Glu Cys Leu Pro Ala Asp Ile Thr Glu Pro Gly Lys Leu Asp Glu Ile
465                 470                 475                 480
```

```
Phe Asp Leu Met Asp Ala Asn Ser Asp Gly Lys Val Thr Phe Glu Glu
            485                 490                 495

Phe Lys Ala Ala Met Gln Arg Asp Ser Ser Leu Gln Asp Met Leu Leu
        500                 505                 510

Ser Ser Leu Arg Pro Ser
        515

<210> SEQ ID NO 4
<211> LENGTH: 6485
<212> TYPE: DNA
<213> ORGANISM: Lotus japonicus
<220> FEATURE:
<221> NAME/KEY: 5'UTR
<222> LOCATION: (1)..(323)
<220> FEATURE:
<221> NAME/KEY: exon
<222> LOCATION: (324)..(1036)
<220> FEATURE:
<221> NAME/KEY: Intron
<222> LOCATION: (1037)..(3265)
<220> FEATURE:
<221> NAME/KEY: exon
<222> LOCATION: (3266)..(3320)
<220> FEATURE:
<221> NAME/KEY: Intron
<222> LOCATION: (3321)..(3611)
<220> FEATURE:
<221> NAME/KEY: exon
<222> LOCATION: (3612)..(3722)
<220> FEATURE:
<221> NAME/KEY: Intron
<222> LOCATION: (3723)..(4114)
<220> FEATURE:
<221> NAME/KEY: exon
<222> LOCATION: (4115)..(4347)
<220> FEATURE:
<221> NAME/KEY: Intron
<222> LOCATION: (4348)..(4715)
<220> FEATURE:
<221> NAME/KEY: exon
<222> LOCATION: (4716)..(4923)
<220> FEATURE:
<221> NAME/KEY: Intron
<222> LOCATION: (4924)..(5593)
<220> FEATURE:
<221> NAME/KEY: exon
<222> LOCATION: (5594)..(5653)
<220> FEATURE:
<221> NAME/KEY: Intron
<222> LOCATION: (5654)..(5737)
<220> FEATURE:
<221> NAME/KEY: exon
<222> LOCATION: (5738)..(5914)

<400> SEQUENCE: 4
ttttcaagtc ggctaaatag tgaatagaag aattttagag tacaaaatgg tagcagttga      60
ctctctctct gtcccttcta aaacagcccc taccagccat tgtttattct cttgtaccta     120
tctgaatttg cttcatattt tatgccataa actaatgcag aaactctcac aaaggctaat     180
gtcaacatca accattttca atacgcgttt tgtaggccga tcattgaaac ttgaagtcat     240
gttatattat acatacctct tctcattgat cattgaacat tttctgagtc tgaaaagatt     300
ccaatatttt caaacactct gcc atg gga tat gat caa acc aga aag ctc tct     353
                         Met Gly Tyr Asp Gln Thr Arg Lys Leu Ser
                           1               5                  10 gat gag tat gag att tca gag att cta gga aga ggt gga ttc tct gtt      401
Asp Glu Tyr Glu Ile Ser Glu Ile Leu Gly Arg Gly Gly Phe Ser Val
             15                  20                  25 gtc aga aaa gga acc aaa aaa tca ggc aat gag aaa acc caa gta gcc      449
Val Arg Lys Gly Thr Lys Lys Ser Gly Asn Glu Lys Thr Gln Val Ala
         30                  35                  40
```

| | | | |
|---|---|---|---|
| atc aaa aca ctc aga agg tta ggt agt tct ccc tct ggg aca ggt ggt<br>Ile Lys Thr Leu Arg Arg Leu Gly Ser Ser Pro Ser Gly Thr Gly Gly<br>      45                         50                     55 | 497 |

| | |
|---|---|
| atc aaa aca ctc aga agg tta ggt agt tct ccc tct ggg aca ggt ggt | 497 |
| Ile Lys Thr Leu Arg Arg Leu Gly Ser Ser Pro Ser Gly Thr Gly Gly | |
|      45                 50              55 | |
| gga cag aag agc aca gca act gtg atg ggg ttc cct tct ttg aga cag | 545 |
| Gly Gln Lys Ser Thr Ala Thr Val Met Gly Phe Pro Ser Leu Arg Gln | |
|  60                 65                  70 | |
| gtt tca gtc tca gat gct ttg ctc acc aat gag att ctt gtg atg agg | 593 |
| Val Ser Val Ser Asp Ala Leu Leu Thr Asn Glu Ile Leu Val Met Arg | |
| 75               80               85                 90 | |
| agg ata gtg gaa aac gtt tcg cca cat cca aac gtg att gat ctc tat | 641 |
| Arg Ile Val Glu Asn Val Ser Pro His Pro Asn Val Ile Asp Leu Tyr | |
|            95                100             105 | |
| gat gtg tgt gag gac tca aat ggg gtg cat ctt gtg ctg gag ctt tgt | 689 |
| Asp Val Cys Glu Asp Ser Asn Gly Val His Leu Val Leu Glu Leu Cys | |
|           110               115              120 | |
| tct ggt ggg gag ctg ttt gat agg att gtt gca cag gat aag tat gct | 737 |
| Ser Gly Gly Glu Leu Phe Asp Arg Ile Val Ala Gln Asp Lys Tyr Ala | |
|       125               130              135 | |
| gag acg gaa gct gcc gcg gtg gtt cgc cag att gcg gcg ggg cta gag | 785 |
| Glu Thr Glu Ala Ala Ala Val Val Arg Gln Ile Ala Ala Gly Leu Glu | |
| 140                 145              150 | |
| gcg gtt cac aag gct gac att gtt cac agg gat ttg aag cct gag aat | 833 |
| Ala Val His Lys Ala Asp Ile Val His Arg Asp Leu Lys Pro Glu Asn | |
| 155                 160              165             170 | |
| tgc ctt ttc ttg gat tcc agg aag gac tct cct ctc aag atc atg gac | 881 |
| Cys Leu Phe Leu Asp Ser Arg Lys Asp Ser Pro Leu Lys Ile Met Asp | |
|                175              180             185 | |
| ttt ggg ttg agc tct gtt gag gag ttc act gac cct gtt gtt ggg ttg | 929 |
| Phe Gly Leu Ser Ser Val Glu Glu Phe Thr Asp Pro Val Val Gly Leu | |
|           190               195              200 | |
| ttt gga tcc att gat tat gtt tca cca gag gct ctt tct caa ggg aag | 977 |
| Phe Gly Ser Ile Asp Tyr Val Ser Pro Glu Ala Leu Ser Gln Gly Lys | |
|       205               210              215 | |
| atc act gcc aag agt gac atg tgg tct ctg gga gtg att cta tat atc | 1025 |
| Ile Thr Ala Lys Ser Asp Met Trp Ser Leu Gly Val Ile Leu Tyr Ile | |
| 220                 225              230 | |
| ttg ctc tct gg gtatgttgtc tttcacttgt tgaaattgtt catattgtgt | 1076 |
| Leu Leu Ser Gly | |
| 235 | |
| tggttgctcc ccatccacct tttgcagagc ccatttggat acaagcttat tgatgtttat | 1136 |
| tgaagcttat ctactagaaa atgcactaaa taagcttcca caatactctt ggcttgcat | 1196 |
| ccaaacggct acttagtgca gtaaatatgg atgccaagaa ggaaatttta gtttctcact | 1256 |
| tattaggtgg cattagtctt tgaaacttaa aaaaaaaaac ccactgataa catgctcgaa | 1316 |
| aattattcta caattgatta tgaaaaatta attgttagaa tataatataa aagcattaaa | 1376 |
| gtgacccttta cccaacagct taagcttttg ggattaagtg gttatttgac atggtatcac | 1436 |
| tagggatggc aacgggtagg atcgggcatg ggttttacaa ttaccaaacc caaacccaaa | 1496 |
| tcccagaacc caaacccaaa cccaaacaca aacccttatg ggcgataaaa tgaaattcat | 1556 |
| gcccaaatcc attgggtttc ggatttaccc gaaactcaaa cccaaaccca ttagttaggt | 1616 |
| agcaactcaa tccagaactt actttcatat aaaagaaaag tgaaattcat ataagaaaa | 1676 |
| aaaaaacaaa tactattcat catcctcatc catcactaaa gtgagacaac aatagtttaa | 1736 |
| agtttacttt ctcaaacata caaaagtaca attaatcatc aaacactaag aacaaagttt | 1796 |
| ataaatatat atatgtatga gggttttttt gtaatttat gtttcgggta tctttgggtt | 1856 |
| cgggtttggg cggggtatgg gcatgaattt aactaatacc aaaatccaaa ctcataaatg | 1916 |

```
gcttcagtaa cgggcaaaac tcaaacccaa acccaaatcc agtcaactcg gattttgccc    1976
gtcaaatcgg atcgggtacc catgggtttg gcaaaatttt ccatccctag gtatcagagc    2036
ctctatgacc gagaggtcta gagttcgatc cttgctcccc tcactttcta attaaaaaag    2096
tggaatttaa ttaagcacat ggtaggtgga cctgtgcatt tatccacgct acaagcccaa    2156
agggctcttg cgtgaggagg cgtgttagaa tataatataa aaccattaaa gtgacccttta   2216 cccaacagct taagcttttg ggataagtgg ttgtttgaca ttaatacttg agagaaactt    2276
atatgaatag cttctgaatg atgttccata attcattttg agaaagaaaa aaagctaatc    2336
caaacatgtg ttagaaaatg aacatgcttg atcgtgatga ataactttc cttaaagtat     2396 ttcaagcact ctctaaattt cgtcttagag tttggatgca agaataccca ggataatcag    2456
ccttgattcg agtttgcaca agactaatga aaactcgaaa tgaagagaag tgattttctg    2516
gaaaacagag gatatgattg tgtgttatga attctgaaca tggactctat ttataggcaa    2576
aacagaacaa tatataaggt tgcgacccctt catatattgt gtctgttaac aacagtcgca   2636
aaaatcaaat tcaaaagag caaaaacaaa cggacgttac ggcaaccgcg tagccgtcgt     2696
tgcgtctaca agccgccact agcgcctcta cgcccacgcc tgtgacaccg gcgagggggtg   2756 gtgtgagtgg aatatgtgac ataaaagctt gggaccacca aactatgcac atgtggcact    2816
atatcctctt tttgtctctt tgttgaatgg ttgacattta atgatatata aatgctttga    2876
aaagttgctc cactttctat gtgagacttc attccaattc attcaatgca aaatcaacac    2936
acttatcatt ttggaacact aagtaattat tacaacaaca tgttgtaagg gaagtcatca    2996
cttcattaca tgaaaaataa atgagttatg agttggtctg ggtatcacct caaaattcct    3056
caaaattggg ggggggggg gggttaagga atgagttttt caataaatct ggtcactcaa     3116 cttttgcacat tatgctgacc agttgttcct tgcttcatta catatatttc cttgtaggaa   3176
catcaataga tggaagactt tttagtattt ctcttaagta atcaaactaa ctcagtatta    3236
tcctcctatg taactttttt cttttgcag g tat ccg cct ttc att gca caa aat    3290
                                 Tyr Pro Pro Phe Ile Ala Gln Asn
                                         240                 245 aat cgc caa aaa caa caa atg ata atc aat gtaagcaaca tctcgcgttg         3340
Asn Arg Gln Lys Gln Gln Met Ile Ile Asn
        250                 255 attaagtgtg tgtgtcttct taggtagaat gagtaatgca ggcagagtca aaattagcaa    3400
tgtaacaaga agtgatatat gttcaaatat attatccaag ttagttcctg gtttttttcc    3460
tttattttag attaatcata gtaacatatc acttttatca caaaaattat atagcacgcg    3520
cacacacata cactatattt agatagatat atagacacac catttgcatt ctgtaaaaaa    3580
attgcttacc aaatgaaaca ttttccaaca g ggg aat ttc agt ttc tat gag        3632
                                   Gly Asn Phe Ser Phe Tyr Glu
                                                       260 aag att tgg aag ggc att acc caa tca gcg aag caa ttg att tca agt       3680
Lys Ile Trp Lys Gly Ile Thr Gln Ser Ala Lys Gln Leu Ile Ser Ser
265                 270                 275 ctt ttg act gtt gat cca agt aag agg cct agt gct caa gag                3722
Leu Leu Thr Val Asp Pro Ser Lys Arg Pro Ser Ala Gln Glu
280                 285                 290 gtatatcaat tgtatattct tactaacttc actaatgtga actaggcagc atatctcatt     3782
ctttactaat aacatggaat gaagtgcatc tcctatgata agagcccttt atagcagaaa    3842
attgccataa aatccaatta catgcattca ttttttttta taaggacatc tgagggaaaa    3902
aaagtacttt ttctaataat atttttgctga tcagaaagca tgactaataa tcacttagca   3962
```

```
attccacaaa gtagcaatgc ctttgcatct caaatacagt atgcactttt cttcaacatt    4022
ttgcatcata ttattttcag tttcaaggtg ttttattgac ataattaagc acaacaataa    4082
ccccagacac aattctgttg tacttggaac ag ctc ttg agt cat cca tgg gtc       4135
                                   Leu Leu Ser His Pro Trp Val
                                       295             300 aga ggt gac aaa gcc aaa gat gag caa atg gac cct gag att gtc tca       4183
Arg Gly Asp Lys Ala Lys Asp Glu Gln Met Asp Pro Glu Ile Val Ser
            305                 310                 315 agg ctg cag agc ttt aat gca aga cgc aaa ctc cgc gca gct gca att       4231
Arg Leu Gln Ser Phe Asn Ala Arg Arg Lys Leu Arg Ala Ala Ala Ile
        320                 325                 330 gct agt gtt tgg agc agc aca atc ttc ctg aga acc aaa aag ctg aga       4279
Ala Ser Val Trp Ser Ser Thr Ile Phe Leu Arg Thr Lys Lys Leu Arg
        335                 340                 345 tcc ttg gta gga act tat gat ctc aaa gaa gag gaa att gaa agt ctc       4327
Ser Leu Val Gly Thr Tyr Asp Leu Lys Glu Glu Glu Ile Glu Ser Leu
    350                 355                 360 agg ata cac ttt aag aag at  gtaagtactc acaagtctcc aaattaatca          4377
Arg Ile His Phe Lys Lys Ile
365                 370 tagatagtta aattagtccc taaaaattta caatcggtta tcttagtcag tgaatcataa    4437
aaatttacac ttgaagtcct tcaattgtac tttgtagtca tattagtctt tccatcaagt    4497
acttcaggac taatttaacc aagaagacac atatgtagag actacttcga tggacaaaat    4557
gtcaatgtag acatctaaaa taagtttcat tattcaaaga ctaacatcat tgagcttgtg    4617
tttattgagt tgagactgtg ttgacaattt agtacaaata tttctgtgca gcacactagc    4677
atttgacaat tttgactaat tcctgtggtt gctaacag a tgt gga aat gga gac      4731
                                          Cys Gly Asn Gly Asp
                                                          375 aat gca act ctg tct gag ttt gtg gag gtg ctg aaa gca atg aag atg       4779
Asn Ala Thr Leu Ser Glu Phe Val Glu Val Leu Lys Ala Met Lys Met
        380                 385                 390 ccc tca ttg atc cct cta gca ccg cgt ata ttt gac ttg ttt gac aac       4827
Pro Ser Leu Ile Pro Leu Ala Pro Arg Ile Phe Asp Leu Phe Asp Asn
    395                 400                 405 aac cgt gat gga aca att gac atg aga gag ata cta tgt ggg ttt tct       4875
Asn Arg Asp Gly Thr Ile Asp Met Arg Glu Ile Leu Cys Gly Phe Ser
410                 415                 420 agc ctc aag aac tcc aaa gga gat gat gct ctc cgt ttg tgc ttc cag       4923
Ser Leu Lys Asn Ser Lys Gly Asp Asp Ala Leu Arg Leu Cys Phe Gln
425                 430                 435                 440 gtgagtcttt ttaagttccg gtcttggtag agcttatttt ctactataat aagtacttaa    4983
gcaggggttt ggttaagttt ataaaaatag ctcatgacat atataaactc ttttgagctt    5043
aattaacttg tatgaataac catttatact tacatctaag ctcttttgag ctaatttcaa    5103
taagtttctc aaattagatt atgagaatat cattagtgtt tgctgacata attgcttagt    5163
taacctattt actcaaacat atccatgaac acatgcacat agacaagaat gcacacatat    5223
agcagtgact cgtgagagct tcaatagtta catccaagaa tatcaattta tgaagcaaaa    5283
aagaaatatc atatatgaga gaagatagta gtattataag taattacata tttactaaca    5343
caaacttttg tgaaaagat gtggttgtta aatgacaaac aaaaagtttg taattgtaat    5403
tacaattatg ttatatgaat gaatgaatgt tacaattttc accaccctct aagtttcaac    5463
aactctggaa aaagactaca acaaacacaa gacaagaaa agaacaacc caaaagcatt     5523 tgatacagta caaagtaaaa gtgttcagca tgatcagcta attttcctca ctgattttct    5583
```

-continued

| | |
|---|---|
| tggccaacag atg tat gac aca gat aga tca ggg tgc atc acc aag gaa<br>           Met Tyr Asp Thr Asp Arg Ser Gly Cys Ile Thr Lys Glu<br>                         445                       450 | 5632 |
| gaa gta gca tcc atg ctc tgt gtaattaatg caccttcctt tcaattaact<br>Glu Val Ala Ser Met Leu Cys<br> 455               460 | 5683 |
| atagccttat cttgtgactt tcttctttct aacacaaatc aattcactga acag gct<br>                                                                  Ala | 5740 |
| ttg cca gag gaa tgt ctt cca gct gat atc act gaa cct ggg aaa ttg<br>Leu Pro Glu Glu Cys Leu Pro Ala Asp Ile Thr Glu Pro Gly Lys Leu<br>              465                    470                    475 | 5788 |
| gat gag ata ttt gac tta atg gat gcc aac agt gat gga aaa gtt aca<br>Asp Glu Ile Phe Asp Leu Met Asp Ala Asn Ser Asp Gly Lys Val Thr<br>             480                    485                    490 | 5836 |
| ttt gaa gaa ttc aaa gct gct atg cag aga gat agc tct ctc caa gac<br>Phe Glu Glu Phe Lys Ala Ala Met Gln Arg Asp Ser Ser Leu Gln Asp<br>495                    500                    505 | 5884 |
| atg ctc ctc tct tct ctt cgt cca tca tag tttttttttt tttccattca<br>Met Leu Leu Ser Ser Leu Arg Pro Ser<br>510                    515 | 5934 |
| tggtgttatg gtctttcaaa ctttgatatt gactacacct tttacgtttc ttttaatctc | 5994 |
| ttttggggct atccttctct ttgaggtatt catactacat ggaaaaaggg tggtaaagag | 6054 |
| ggtgaaattg tgtcatctaa cttttgctat gacaactagg aacttttgca ttctcatgta | 6114 |
| atactacaac tagcttaaga gagcggctca atgaatgtca aggcttaaaa tgaaatttaa | 6174 |
| gaggagattt tttaaattaa ttaaatagtt ttattgaaat tattgtaatt ctattttta | 6234 |
| tattaatctt ttgtagtttg agttaagtta ttaatcattt aacatttctt ttttgaatta | 6294 |
| atcatagaat aaattgtcaa tcaatttaat cacagttgat agttgaggca ctgttgatat | 6354 |
| tagataaggc aaataatagt aaagttaatt cattgaatat tgagagggga aaacaaagaa | 6414 |
| cggtttataa tcttgatgat aataattttg aaagaatgga ggtagaagat ttcaattgca | 6474 |
| atatatgaaa a | 6485 |

```
<210> SEQ ID NO 5
<211> LENGTH: 1557
<212> TYPE: DNA
<213> ORGANISM: Lotus japonicus
<220> FEATURE:
<221> NAME/KEY: CDS
<222> LOCATION: (1)..(1557)

<400> SEQUENCE: 5
```

| | |
|---|---|
| atg gga tat gat caa acc aga aag ctc tct gat gag tat gag att tca<br>Met Gly Tyr Asp Gln Thr Arg Lys Leu Ser Asp Glu Tyr Glu Ile Ser<br>1                    5                    10                    15 | 48 |
| gag att cta gga aga ggt gga ttc tct gtt gtc aga aaa gga acc aaa<br>Glu Ile Leu Gly Arg Gly Gly Phe Ser Val Val Arg Lys Gly Thr Lys<br>           20                    25                    30 | 96 |
| aaa tca ggc aat gag aaa acc caa gta gcc atc aaa aca ctc aga agg<br>Lys Ser Gly Asn Glu Lys Thr Gln Val Ala Ile Lys Thr Leu Arg Arg<br>     35                    40                    45 | 144 |
| tta ggt agt tct ccc tct ggg aca ggt ggt gga cag aag agc aca gca<br>Leu Gly Ser Ser Pro Ser Gly Thr Gly Gly Gly Gln Lys Ser Thr Ala<br>50                    55                    60 | 192 |
| act gtg atg ggg ttc cct tct ttg aga cag gtt tca gtc tca gat gct<br>Thr Val Met Gly Phe Pro Ser Leu Arg Gln Val Ser Val Ser Asp Ala<br>65                      70                    75                    80 | 240 |
| ttg ctc acc aat gag att ctt gtg atg agg agg ata gtg gaa aac gtt | 288 |

-continued

| | | | | | | | | | | | | | | | |
|---|---|---|---|---|---|---|---|---|---|---|---|---|---|---|---|
| Leu | Leu | Thr | Asn | Glu | Ile | Leu | Val | Met | Arg | Ile | Val | Glu | Asn | Val | |
| | | | | 85 | | | | 90 | | | | 95 | | | |

| tcg | cca | cat | cca | aac | gtg | att | gat | ctc | tat | gat | gtg | tgt | gag | gac | tca | 336 |
|---|---|---|---|---|---|---|---|---|---|---|---|---|---|---|---|---|
| Ser | Pro | His | Pro | Asn | Val | Ile | Asp | Leu | Tyr | Asp | Val | Cys | Glu | Asp | Ser | |
| | | | 100 | | | | | 105 | | | | | 110 | | | |

| aat | ggg | gtg | cat | ctt | gtg | ctg | gag | ctt | tgt | tct | ggt | ggg | gag | ctg | ttt | 384 |
|---|---|---|---|---|---|---|---|---|---|---|---|---|---|---|---|---|
| Asn | Gly | Val | His | Leu | Val | Leu | Glu | Leu | Cys | Ser | Gly | Gly | Glu | Leu | Phe | |
| | | | 115 | | | | | 120 | | | | | 125 | | | |

| gat | agg | att | gtt | gca | cag | gat | aag | tat | gct | gag | acg | gaa | gct | gcc | gcg | 432 |
|---|---|---|---|---|---|---|---|---|---|---|---|---|---|---|---|---|
| Asp | Arg | Ile | Val | Ala | Gln | Asp | Lys | Tyr | Ala | Glu | Thr | Glu | Ala | Ala | Ala | |
| | 130 | | | | | 135 | | | | | 140 | | | | | |

| gtg | gtt | cgc | cag | att | gcg | gcg | ggg | cta | gag | gcg | gtt | cac | aag | gct | gac | 480 |
|---|---|---|---|---|---|---|---|---|---|---|---|---|---|---|---|---|
| Val | Val | Arg | Gln | Ile | Ala | Ala | Gly | Leu | Glu | Ala | Val | His | Lys | Ala | Asp | |
| 145 | | | | | 150 | | | | | 155 | | | | | 160 | |

| att | gtt | cac | agg | gat | ttg | aag | cct | gag | aat | tgc | ctt | ttc | ttg | gat | tcc | 528 |
|---|---|---|---|---|---|---|---|---|---|---|---|---|---|---|---|---|
| Ile | Val | His | Arg | Asp | Leu | Lys | Pro | Glu | Asn | Cys | Leu | Phe | Leu | Asp | Ser | |
| | | | | 165 | | | | | 170 | | | | | 175 | | |

| agg | aag | gac | tct | cct | ctc | aag | atc | atg | gac | ttt | ggg | ttg | agc | tct | gtt | 576 |
|---|---|---|---|---|---|---|---|---|---|---|---|---|---|---|---|---|
| Arg | Lys | Asp | Ser | Pro | Leu | Lys | Ile | Met | Asp | Phe | Gly | Leu | Ser | Ser | Val | |
| | | | 180 | | | | | 185 | | | | | 190 | | | |

| gag | gag | ttc | act | gac | cct | gtt | gtt | ggg | ttg | ttt | gga | tcc | att | gat | tat | 624 |
|---|---|---|---|---|---|---|---|---|---|---|---|---|---|---|---|---|
| Glu | Glu | Phe | Thr | Asp | Pro | Val | Val | Gly | Leu | Phe | Gly | Ser | Ile | Asp | Tyr | |
| | | 195 | | | | | 200 | | | | | 205 | | | | |

| gtt | tca | cca | gag | gct | ctt | tct | caa | ggg | aag | atc | act | gcc | aag | agt | gac | 672 |
|---|---|---|---|---|---|---|---|---|---|---|---|---|---|---|---|---|
| Val | Ser | Pro | Glu | Ala | Leu | Ser | Gln | Gly | Lys | Ile | Thr | Ala | Lys | Ser | Asp | |
| | 210 | | | | | 215 | | | | | 220 | | | | | |

| atg | tgg | tct | ctg | gga | gtg | att | cta | tat | atc | ttg | ctc | tct | ggg | tat | ccg | 720 |
|---|---|---|---|---|---|---|---|---|---|---|---|---|---|---|---|---|
| Met | Trp | Ser | Leu | Gly | Val | Ile | Leu | Tyr | Ile | Leu | Leu | Ser | Gly | Tyr | Pro | |
| 225 | | | | | 230 | | | | | 235 | | | | | 240 | |

| cct | ttc | att | gca | caa | aat | aat | cgc | caa | aaa | caa | caa | atg | ata | atc | aat | 768 |
|---|---|---|---|---|---|---|---|---|---|---|---|---|---|---|---|---|
| Pro | Phe | Ile | Ala | Gln | Asn | Asn | Arg | Gln | Lys | Gln | Gln | Met | Ile | Ile | Asn | |
| | | | | 245 | | | | | 250 | | | | | 255 | | |

| ggg | aat | ttc | agt | ttc | tat | gag | aag | att | tgg | aag | ggc | att | acc | caa | tca | 816 |
|---|---|---|---|---|---|---|---|---|---|---|---|---|---|---|---|---|
| Gly | Asn | Phe | Ser | Phe | Tyr | Glu | Lys | Ile | Trp | Lys | Gly | Ile | Thr | Gln | Ser | |
| | | | 260 | | | | | 265 | | | | | 270 | | | |

| gcg | aag | caa | ttg | att | tca | agt | ctt | ttg | act | gtt | gat | cca | agt | aag | agg | 864 |
|---|---|---|---|---|---|---|---|---|---|---|---|---|---|---|---|---|
| Ala | Lys | Gln | Leu | Ile | Ser | Ser | Leu | Leu | Thr | Val | Asp | Pro | Ser | Lys | Arg | |
| | | 275 | | | | | 280 | | | | | 285 | | | | |

| cct | agt | gct | caa | gag | ctc | ttg | agt | cat | cca | tgg | gtc | aga | ggt | gac | aaa | 912 |
|---|---|---|---|---|---|---|---|---|---|---|---|---|---|---|---|---|
| Pro | Ser | Ala | Gln | Glu | Leu | Leu | Ser | His | Pro | Trp | Val | Arg | Gly | Asp | Lys | |
| | 290 | | | | | 295 | | | | | 300 | | | | | |

| gcc | aaa | gat | gag | caa | atg | gac | cct | gag | att | gtc | tca | agg | ctg | cag | agc | 960 |
|---|---|---|---|---|---|---|---|---|---|---|---|---|---|---|---|---|
| Ala | Lys | Asp | Glu | Gln | Met | Asp | Pro | Glu | Ile | Val | Ser | Arg | Leu | Gln | Ser | |
| 305 | | | | | 310 | | | | | 315 | | | | | 320 | |

| ttt | aat | gca | aga | cgc | aaa | ctc | cgc | gca | gct | gca | att | gct | agt | gtt | tgg | 1008 |
|---|---|---|---|---|---|---|---|---|---|---|---|---|---|---|---|---|
| Phe | Asn | Ala | Arg | Arg | Lys | Leu | Arg | Ala | Ala | Ala | Ile | Ala | Ser | Val | Trp | |
| | | | | 325 | | | | | 330 | | | | | 335 | | |

| agc | agc | aca | atc | ttc | ctg | aga | acc | aaa | aag | ctg | aga | tcc | ttg | gta | gga | 1056 |
|---|---|---|---|---|---|---|---|---|---|---|---|---|---|---|---|---|
| Ser | Ser | Thr | Ile | Phe | Leu | Arg | Thr | Lys | Lys | Leu | Arg | Ser | Leu | Val | Gly | |
| | | | 340 | | | | | 345 | | | | | 350 | | | |

| act | tat | gat | ctc | aaa | gaa | gag | gaa | att | gaa | agt | ctc | agg | ata | cac | ttt | 1104 |
|---|---|---|---|---|---|---|---|---|---|---|---|---|---|---|---|---|
| Thr | Tyr | Asp | Leu | Lys | Glu | Glu | Glu | Ile | Glu | Ser | Leu | Arg | Ile | His | Phe | |
| | | 355 | | | | | 360 | | | | | 365 | | | | |

| aag | aag | ata | tgt | gga | aat | gga | gac | aat | gca | act | ctg | tct | gag | ttt | gtg | 1152 |
|---|---|---|---|---|---|---|---|---|---|---|---|---|---|---|---|---|
| Lys | Lys | Ile | Cys | Gly | Asn | Gly | Asp | Asn | Ala | Thr | Leu | Ser | Glu | Phe | Val | |
| | 370 | | | | | 375 | | | | | 380 | | | | | |

| gag | gtg | ctg | aaa | gca | atg | aag | atg | ccc | tca | ttg | atc | cct | cta | gca | ccg | 1200 |
|---|---|---|---|---|---|---|---|---|---|---|---|---|---|---|---|---|
| Glu | Val | Leu | Lys | Ala | Met | Lys | Met | Pro | Ser | Leu | Ile | Pro | Leu | Ala | Pro | |
| 385 | | | | | 390 | | | | | 395 | | | | | 400 | |

| cgt | ata | ttt | gac | ttg | ttt | gac | aac | aac | cgt | gat | gga | aca | att | gac | atg | 1248 |

```
Arg Ile Phe Asp Leu Phe Asp Asn Asn Arg Asp Gly Thr Ile Asp Met
                405                 410                 415 aga gag ata cta tgt ggg ttt tct agc ctc aag aac tcc aaa gga gat         1296
Arg Glu Ile Leu Cys Gly Phe Ser Ser Leu Lys Asn Ser Lys Gly Asp
            420                 425                 430 gat gct ctc cgt ttg tgc ttc cag atg tat gac aca gat aga tca ggg         1344
Asp Ala Leu Arg Leu Cys Phe Gln Met Tyr Asp Thr Asp Arg Ser Gly
        435                 440                 445 tgc atc acc aag gaa gaa gta gca tcc atg ctc tgt gct ttg cca gag         1392
Cys Ile Thr Lys Glu Glu Val Ala Ser Met Leu Cys Ala Leu Pro Glu
    450                 455                 460 gaa tgt ctt cca gct gat atc act gaa cct ggg aaa ttg gat gag ata         1440
Glu Cys Leu Pro Ala Asp Ile Thr Glu Pro Gly Lys Leu Asp Glu Ile
465                 470                 475                 480 ttt gac tta atg gat gcc aac agt gat gga aaa gtt aca ttt gaa gaa         1488
Phe Asp Leu Met Asp Ala Asn Ser Asp Gly Lys Val Thr Phe Glu Glu
                485                 490                 495 ttc aaa gct gct atg cag aga gat agc tct ctc caa gac atg ctc ctc         1536
Phe Lys Ala Ala Met Gln Arg Asp Ser Ser Leu Gln Asp Met Leu Leu
            500                 505                 510 tct tct ctt cgt cca tca tag                                             1557
Ser Ser Leu Arg Pro Ser
        515

<210> SEQ ID NO 6
<211> LENGTH: 518
<212> TYPE: PRT
<213> ORGANISM: Lotus japonicus

<400> SEQUENCE: 6

Met Gly Tyr Asp Gln Thr Arg Lys Leu Ser Asp Glu Tyr Glu Ile Ser
1               5                   10                  15

Glu Ile Leu Gly Arg Gly Gly Phe Ser Val Val Arg Lys Gly Thr Lys
            20                  25                  30

Lys Ser Gly Asn Glu Lys Thr Gln Val Ala Ile Lys Thr Leu Arg Arg
        35                  40                  45

Leu Gly Ser Ser Pro Ser Gly Thr Gly Gly Gln Lys Ser Thr Ala
    50                  55                  60

Thr Val Met Gly Phe Pro Ser Leu Arg Gln Val Ser Val Ser Asp Ala
65                  70                  75                  80

Leu Leu Thr Asn Glu Ile Leu Val Met Arg Arg Ile Val Glu Asn Val
                85                  90                  95

Ser Pro His Pro Asn Val Ile Asp Leu Tyr Asp Val Cys Glu Asp Ser
            100                 105                 110

Asn Gly Val His Leu Val Leu Glu Leu Cys Ser Gly Gly Glu Leu Phe
        115                 120                 125

Asp Arg Ile Val Ala Gln Asp Lys Tyr Ala Glu Thr Glu Ala Ala Ala
    130                 135                 140

Val Val Arg Gln Ile Ala Ala Gly Leu Glu Ala Val His Lys Ala Asp
145                 150                 155                 160

Ile Val His Arg Asp Leu Lys Pro Glu Asn Cys Leu Phe Leu Asp Ser
                165                 170                 175

Arg Lys Asp Ser Pro Leu Lys Ile Met Asp Phe Gly Leu Ser Ser Val
            180                 185                 190

Glu Glu Phe Thr Asp Pro Val Val Gly Leu Phe Gly Ser Ile Asp Tyr
        195                 200                 205

Val Ser Pro Glu Ala Leu Ser Gln Gly Lys Ile Thr Ala Lys Ser Asp
    210                 215                 220
```

```
Met Trp Ser Leu Gly Val Ile Leu Tyr Ile Leu Leu Ser Gly Tyr Pro
225                 230                 235                 240

Pro Phe Ile Ala Gln Asn Asn Arg Gln Lys Gln Gln Met Ile Ile Asn
                245                 250                 255

Gly Asn Phe Ser Phe Tyr Glu Lys Ile Trp Lys Gly Ile Thr Gln Ser
            260                 265                 270

Ala Lys Gln Leu Ile Ser Ser Leu Leu Thr Val Asp Pro Ser Lys Arg
        275                 280                 285

Pro Ser Ala Gln Glu Leu Leu Ser His Pro Trp Val Arg Gly Asp Lys
    290                 295                 300

Ala Lys Asp Glu Gln Met Asp Pro Glu Ile Val Ser Arg Leu Gln Ser
305                 310                 315                 320

Phe Asn Ala Arg Arg Lys Leu Arg Ala Ala Ile Ala Ser Val Trp
                325                 330                 335

Ser Ser Thr Ile Phe Leu Arg Thr Lys Lys Leu Arg Ser Leu Val Gly
            340                 345                 350

Thr Tyr Asp Leu Lys Glu Glu Ile Glu Ser Leu Arg Ile His Phe
        355                 360                 365

Lys Lys Ile Cys Gly Asn Gly Asp Asn Ala Thr Leu Ser Glu Phe Val
        370                 375                 380

Glu Val Leu Lys Ala Met Lys Met Pro Ser Leu Ile Pro Leu Ala Pro
385                 390                 395                 400

Arg Ile Phe Asp Leu Phe Asp Asn Asn Arg Asp Gly Thr Ile Asp Met
                405                 410                 415

Arg Glu Ile Leu Cys Gly Phe Ser Ser Leu Lys Asn Ser Lys Gly Asp
                420                 425                 430

Asp Ala Leu Arg Leu Cys Phe Gln Met Tyr Asp Thr Asp Arg Ser Gly
            435                 440                 445

Cys Ile Thr Lys Glu Glu Val Ala Ser Met Leu Cys Ala Leu Pro Glu
        450                 455                 460

Glu Cys Leu Pro Ala Asp Ile Thr Glu Pro Gly Lys Leu Asp Glu Ile
465                 470                 475                 480

Phe Asp Leu Met Asp Ala Asn Ser Asp Gly Lys Val Thr Phe Glu Glu
                485                 490                 495

Phe Lys Ala Ala Met Gln Arg Asp Ser Ser Leu Gln Asp Met Leu Leu
            500                 505                 510

Ser Ser Leu Arg Pro Ser
        515

<210> SEQ ID NO 7
<211> LENGTH: 523
<212> TYPE: PRT
<213> ORGANISM: Medicago truncatula
<220> FEATURE:
<221> NAME/KEY: MISC_FEATURE
<222> LOCATION: (271)..(271)
<223> OTHER INFORMATION: Xaa can be any naturally occurring amino acid
      excluding Thr or Ser

<400> SEQUENCE: 7

Met Gly Tyr Gly Thr Arg Lys Leu Ser Asp Glu Tyr Glu Val Ser Glu
1               5                   10                  15

Ile Leu Gly Arg Gly Gly Phe Ser Val Val Arg Lys Gly Thr Lys Lys
            20                  25                  30

Ser Ser Ile Glu Glu Lys Ser Gln Ser Gln Val Ala Ile Lys Thr
        35                  40                  45
```

-continued

```
Leu Arg Arg Leu Gly Ala Ser Asn Asn Pro Ser Gly Leu Pro Arg Lys
 50                  55                  60

Lys Asp Ile Gly Glu Lys Ser Thr Ile Gly Phe Pro Thr Met Arg Gln
 65                      70                  75                  80

Val Ser Val Ser Asp Thr Leu Leu Thr Asn Glu Ile Leu Val Met Arg
                 85                  90                  95

Arg Ile Val Glu Asn Val Ser Pro His Pro Asn Val Ile Asp Leu Tyr
                100                 105                 110

Asp Val Tyr Glu Asp Thr Asn Gly Val His Leu Val Leu Glu Leu Cys
            115                 120                 125

Ser Gly Gly Glu Leu Phe Asp Arg Ile Val Ala Gln Asp Lys Tyr Ser
130                 135                 140

Glu Thr Glu Ala Ala Thr Val Val His Gln Ile Ala Ser Gly Leu Glu
145                 150                 155                 160

Ala Val His Arg Ala Asn Ile Val His Arg Asp Leu Lys Pro Glu Asn
                165                 170                 175

Cys Leu Phe Leu Asp Val Arg Lys Asp Ser Pro Leu Lys Ile Met Asp
            180                 185                 190

Phe Gly Leu Ser Ser Val Glu Glu Phe Thr Asp Pro Val Val Gly Leu
        195                 200                 205

Phe Gly Ser Ile Asp Tyr Val Ser Pro Glu Ala Leu Ser Gln Gly Lys
210                 215                 220

Ile Thr Thr Lys Ser Asp Met Trp Ser Leu Gly Val Ile Leu Tyr Ile
225                 230                 235                 240

Leu Leu Ser Gly Tyr Pro Pro Phe Ile Ala Gln Asn Asn Arg Gln Lys
                245                 250                 255

Gln Gln Met Ile Met Asn Gly Asn Phe Ser Phe Tyr Glu Lys Xaa Trp
            260                 265                 270

Lys Gly Ile Ser Gln Pro Ala Lys Asn Leu Ile Ser Ser Leu Leu Thr
        275                 280                 285

Val Asp Pro Ser Lys Arg Pro Ser Ala Leu Glu Leu Leu Ser Asp Pro
290                 295                 300

Trp Val Lys Gly Glu Lys Ala Lys Asp Val Gln Met Asp Pro Glu Ile
305                 310                 315                 320

Val Ser Arg Leu Gln Ser Phe Asn Ala Arg Arg Lys Leu Arg Ala Ala
                325                 330                 335

Ala Ile Ala Ser Val Trp Ser Ser Thr Ile Phe Leu Arg Thr Lys Lys
            340                 345                 350

Leu Lys Ser Leu Val Gly Ser Tyr Asp Leu Lys Glu Glu Glu Ile Glu
        355                 360                 365

Asn Leu Arg Met His Phe Lys Lys Ile Cys Ala Asp Arg Asp Asn Ala
370                 375                 380

Thr Leu Ser Glu Phe Glu Glu Val Leu Lys Ala Met Asn Met Leu Ser
385                 390                 395                 400

Leu Ile Pro Phe Ala Ser Arg Ile Phe Asp Leu Phe Asp Asn Asn Arg
                405                 410                 415

Asp Gly Thr Val Asp Met Arg Glu Ile Leu Cys Gly Phe Ser Ser Leu
            420                 425                 430

Lys Asn Ser Lys Gly Glu Asp Ala Leu Arg Leu Cys Phe Gln Met Tyr
        435                 440                 445

Asp Thr Asp Arg Ser Gly Cys Ile Ser Lys Glu Glu Val Ala Ser Met
450                 455                 460

Leu Arg Ala Leu Pro Tyr Asp Cys Leu Pro Thr Asp Ile Thr Glu Pro
465                 470                 475                 480
```

```
Gly Lys Leu Asp Glu Ile Phe Asp Leu Met Asp Ala Asn Asn Asp Gly
            485                 490                 495

Lys Val Thr Phe Asp Glu Phe Lys Ala Ala Met Gln Arg Asp Ser Ser
            500                 505                 510

Leu Gln Asp Val Val Leu Ser Ser Ile Arg Pro
            515                 520

<210> SEQ ID NO 8
<211> LENGTH: 520
<212> TYPE: PRT
<213> ORGANISM: Pisum sativum
<220> FEATURE:
<221> NAME/KEY: MISC_FEATURE
<222> LOCATION: (279)..(279)
<223> OTHER INFORMATION: Xaa can be any naturally occurring amino acid
      excluding Thr or Ser

<400> SEQUENCE: 8

Met Gly Tyr Gly Thr Arg Lys Leu Ser Asp Val Tyr Glu Val Ser Glu
1               5                   10                  15

Ile Leu Gly Arg Gly Gly Phe Ser Val Val Arg Lys Gly Thr Arg Lys
            20                  25                  30

Ser Asn Asn Asp Asp Glu Lys Ser Gln Ser Gln Ser Lys Ser Gln Ser
        35                  40                  45

Gln Ser Gln Val Ala Ile Lys Thr Leu Arg Arg Leu Gly Thr Ser Asn
    50                  55                  60

Asn Leu Pro Arg Lys Lys Asp Gly Gly Glu Asn Ser Thr Glu Thr Met
65                  70                  75                  80

Met Lys Phe Pro Thr Met Arg Gln Val Ser Val Ser Asp Ala Leu Leu
                85                  90                  95

Thr Asn Glu Ile Leu Val Met Arg Arg Ile Val Glu Asn Val Ser Pro
            100                 105                 110

His Pro Asn Val Ile Asp Leu Tyr Asp Val Tyr Glu Asp Thr Asn Gly
        115                 120                 125

Val His Leu Val Leu Glu Leu Cys Ser Gly Gly Glu Leu Phe Asp Arg
    130                 135                 140

Ile Val Ala Gln Asp Lys Tyr Ser Glu Thr Glu Ala Ser Thr Val Val
145                 150                 155                 160

His Gln Ile Val Ala Gly Leu Glu Ala Ile His Arg Ala Asn Ile Ile
                165                 170                 175

His Arg Asp Leu Lys Pro Glu Asn Cys Leu Phe Leu Ser Val Gly Lys
            180                 185                 190

Asp Ser Ser Leu Lys Ile Met Asp Phe Gly Leu Ser Ser Val Glu Glu
        195                 200                 205

Phe Thr Asp Pro Val Val Gly Leu Phe Gly Ser Ile Asp Tyr Val Ser
    210                 215                 220

Pro Glu Ala Leu Ser Gln Gly Lys Ile Thr Thr Lys Ser Asp Met Trp
225                 230                 235                 240

Ser Leu Gly Val Ile Leu Tyr Ile Leu Leu Ser Gly Tyr Pro Pro Phe
                245                 250                 255

Ile Ala Gln Asn Asn Arg Gln Lys Gln Gln Met Ile Leu Asn Gly Asn
            260                 265                 270

Phe Ser Phe Tyr Glu Lys Xaa Trp Lys Gly Ile Ser Gln Ser Ala Lys
        275                 280                 285

Asn Leu Ile Ser Ser Leu Leu Thr Val Asp Pro Ala Lys Arg Pro Ser
    290                 295                 300
```

-continued

```
Ala Gln Glu Leu Leu Ser Asp Pro Trp Val Lys Gly Glu Lys Ala Lys
305                 310                 315                 320

Asp Asp Gln Met Asp Pro Glu Ile Val Ser Arg Leu Gln Arg Phe Asn
            325                 330                 335

Ala Arg Arg Lys Leu Arg Ala Ala Ile Ala Ser Val Trp Ser Ser
        340                 345                 350

Thr Ile Phe Leu Arg Thr Lys Lys Leu Lys Ser Leu Val Gly Ser Tyr
            355                 360                 365

Asp Leu Lys Glu Asp Glu Ile Glu Asn Leu Arg Met His Phe Lys Lys
        370                 375                 380

Ile Cys Ala Asp Arg Asp Asn Ala Thr Leu Cys Glu Phe Glu Glu Val
385                 390                 395                 400

Leu Lys Ala Met Lys Met Pro Ser Leu Ile Pro Phe Ala Ala Arg Ile
                405                 410                 415

Phe Asp Leu Phe Asp Asn Asn Arg Asp Gly Thr Val Asp Met Arg Glu
            420                 425                 430

Ile Leu Cys Gly Phe Ser Ser Leu Lys Asn Ser Lys Gly Glu Asp Ala
        435                 440                 445

Leu Arg Leu Cys Phe Gln Ala Arg Asp Arg Ser Gly Cys Ile Thr Lys
    450                 455                 460

Glu Glu Val Ala Ser Met Leu Arg Ala Leu Pro Tyr Asp Cys Leu Pro
465                 470                 475                 480

Thr Asp Ile Thr Glu Pro Gly Lys Leu Asp Glu Ile Phe Asp Leu Met
                485                 490                 495

Asp Ala Asn Ser Asp Gly Lys Val Thr Phe Asp Glu Phe Lys Ala Ala
            500                 505                 510

Met Gln Arg Asp Ser Ser Leu Gln
        515                 520

<210> SEQ ID NO 9
<211> LENGTH: 517
<212> TYPE: PRT
<213> ORGANISM: Nicotiana tabacum
<220> FEATURE:
<221> NAME/KEY: MISC_FEATURE
<222> LOCATION: (264)..(264)
<223> OTHER INFORMATION: Xaa can be any naturally occurring amino acid
      excluding Thr or Ser

<400> SEQUENCE: 9

Met Gly Gln Arg Glu Asp Gly Lys Thr Leu Ser Asp Glu Tyr Glu Val
1               5                   10                  15

Thr Asp Ile Leu Gly Arg Gly Gly Phe Ser Val Val Arg Arg Gly Thr
            20                  25                  30

Arg Arg Arg Thr Leu His Ser Gly Gln His His Glu Val Val Ala Ile
        35                  40                  45

Lys Thr Leu Arg Arg Phe Gly Pro Pro Ala Pro Glu Lys Lys Ser
    50                  55                  60

Leu Asn Lys Ser Arg Val Pro Gln Ala Ala Leu Ile Ser Glu Thr Leu
65                  70                  75                  80

Leu Thr Asn Glu Leu Leu Val Met Ile Lys Ile Val Glu Asp Val Ser
                85                  90                  95

Pro His Pro Asn Val Ile His Leu Tyr Asp Val Cys Glu Asp Pro Ser
            100                 105                 110

Gly Val His Leu Ile Leu Glu Leu Cys Ser Gly Gly Glu Leu Phe Asp
        115                 120                 125

Arg Ile Ala Gly Gln Ala Arg Tyr Asn Glu Ala Gly Ala Ala Ala Val
```

```
            130                 135                 140
Val Arg Gln Ile Ala Lys Gly Leu Glu Ala Leu His Gly Ala Ser Ile
145                 150                 155                 160

Val His Arg Asp Leu Lys Pro Glu Asn Cys Leu Phe Leu Asn Lys Asp
                165                 170                 175

Glu Asn Ser Pro Leu Lys Ile Met Asp Phe Gly Leu Ser Ser Ile Glu
            180                 185                 190

Asp Phe Ala Asn Pro Val Val Gly Leu Phe Gly Ser Ile Asp Tyr Val
        195                 200                 205

Ser Pro Glu Ala Leu Ser Arg Glu Asn Ile Thr Thr Lys Ser Asp Ile
    210                 215                 220

Trp Ser Leu Gly Val Ile Leu Tyr Ile Leu Leu Ser Gly Tyr Pro Pro
225                 230                 235                 240

Phe Ile Ala Pro Ser Asn Arg Lys Lys Gln Gln Met Ile Leu Asn Gly
                245                 250                 255

Gln Phe Ser Phe Asp Glu Lys Xaa Trp Lys Asn Ile Ser Ser Ser Ala
            260                 265                 270

Lys Gln Leu Ile Ser Ser Leu Leu Lys Val Asp Pro Asn Met Arg Pro
        275                 280                 285

Thr Ala Gln Glu Ile Leu Glu His Pro Trp Val Thr Gly Asp Leu Ala
    290                 295                 300

Lys Gln Glu Gln Met Asp Ala Glu Ile Val Ser Arg Leu Gln Ser Phe
305                 310                 315                 320

Asn Ser Arg Arg Lys Phe Arg Ala Ala Ala Met Ala Ser Val Leu Ser
                325                 330                 335

Ser Ser Phe Ser Leu Arg Thr Lys Lys Leu Lys Lys Leu Val Gly Ser
            340                 345                 350

Tyr Asp Leu Lys Pro Glu Glu Leu Gln Asn Leu Ser His Asn Phe Lys
        355                 360                 365

Lys Ile Cys Lys Asn Gly Glu Asn Ser Thr Leu Leu Glu Phe Glu Glu
    370                 375                 380

Val Leu Lys Ala Met Glu Met Ser Ser Leu Val Pro Leu Ala Pro Arg
385                 390                 395                 400

Ile Phe Asp Leu Phe Asp Asn Asn Arg Asp Gly Thr Val Asp Met Arg
                405                 410                 415

Glu Ile Ile Gly Gly Phe Ser Ser Leu Lys Tyr Ser Gln Gly Asp Asp
            420                 425                 430

Ala Leu Arg Leu Cys Phe Gln Met Tyr Asp Thr Asp Arg Ser Gly Cys
        435                 440                 445

Ile Ser Lys Glu Glu Val Ala Ser Met Leu Arg Ala Leu Pro Glu Asp
    450                 455                 460

Cys Leu Pro Ile Asn Ile Thr Glu Pro Gly Lys Leu Asp Glu Ile Phe
465                 470                 475                 480

Asp Leu Met Asp Ala Asn Ser Asp Gly Lys Val Thr Phe Asp Glu Phe
                485                 490                 495

Lys Ala Ala Met Gln Arg Asp Ser Ser Leu Gln Asp Val Val Leu Ser
            500                 505                 510

Ser Leu Arg Pro Ser
        515

<210> SEQ ID NO 10
<211> LENGTH: 517
<212> TYPE: PRT
<213> ORGANISM: Nicotiana tabacum
<220> FEATURE:
```

```
<221> NAME/KEY: MISC_FEATURE
<222> LOCATION: (264)..(264)
<223> OTHER INFORMATION: Xaa can be any naturally occurring amino acid
      excluding Thr or Ser

<400> SEQUENCE: 10
```

| Met | Gly | Gln | Arg | Glu | Asp | Ile | Arg | Thr | Leu | Ser | Asn | Glu | Tyr | Glu | Val |
|-----|-----|-----|-----|-----|-----|-----|-----|-----|-----|-----|-----|-----|-----|-----|-----|
| 1 | | | | 5 | | | | | 10 | | | | | 15 | |

| Thr | Asp | Ile | Pro | Arg | Arg | Gly | Gly | Leu | Ser | Val | Val | Arg | Arg | Gly | Thr |
| | | | 20 | | | | | 25 | | | | | 30 | | |

| Arg | Arg | Arg | Thr | Leu | His | Ser | Gly | Gln | His | His | Glu | Val | Val | Ala | Ile |
| | | 35 | | | | | 40 | | | | | 45 | | | |

| Lys | Thr | Leu | Arg | Arg | Phe | Gly | Pro | Pro | Ala | Pro | Glu | Lys | Lys | Ser |
| | 50 | | | | | 55 | | | | 60 | | | | | |

| Leu | Asn | Lys | Ser | Arg | Val | Pro | Gln | Ala | Ala | Leu | Ile | Ser | Glu | Thr | Leu |
| 65 | | | | | 70 | | | | | 75 | | | | | 80 |

| Leu | Thr | Asn | Glu | Leu | Leu | Val | Met | Ile | Lys | Ile | Val | Glu | Asp | Val | Ser |
| | | | | 85 | | | | | 90 | | | | | 95 | |

| Pro | His | Pro | Asn | Val | Ile | His | Leu | Tyr | Asp | Val | Cys | Glu | Asp | Pro | Ser |
| | | | 100 | | | | | 105 | | | | | 110 | | |

| Gly | Val | His | Leu | Ile | Leu | Glu | Leu | Cys | Ser | Gly | Gly | Glu | Leu | Phe | Asp |
| | | | 115 | | | | | 120 | | | | | 125 | | |

| Arg | Ile | Ala | Gly | Gln | Ala | Arg | Tyr | Asn | Glu | Glu | Gly | Ala | Ala | Ala | Val |
| | 130 | | | | | 135 | | | | | 140 | | | | |

| Val | Arg | Gln | Ile | Ala | Lys | Gly | Leu | Glu | Ala | Leu | His | Gly | Ala | Ser | Ile |
| 145 | | | | | 150 | | | | | 155 | | | | | 160 |

| Val | His | Arg | Asp | Leu | Lys | Pro | Glu | Asn | Cys | Leu | Phe | Leu | Asn | Lys | Asp |
| | | | 165 | | | | | 170 | | | | | 175 | | |

| Glu | Asn | Ser | Pro | Leu | Lys | Ile | Met | Asp | Phe | Gly | Leu | Ser | Ser | Ile | Glu |
| | | | 180 | | | | | 185 | | | | | 190 | | |

| Asp | Phe | Ala | Asn | Pro | Val | Val | Gly | Leu | Phe | Gly | Ser | Ile | Asp | Tyr | Val |
| | | 195 | | | | | 200 | | | | | 205 | | | |

| Ser | Pro | Glu | Ala | Leu | Ser | Arg | Glu | Lys | Ile | Thr | Thr | Lys | Ser | Asp | Ile |
| | 210 | | | | | 215 | | | | | 220 | | | | |

| Trp | Ser | Leu | Gly | Val | Ile | Leu | Tyr | Ile | Leu | Leu | Ser | Gly | Tyr | Pro | Pro |
| 225 | | | | | 230 | | | | | 235 | | | | | 240 |

| Phe | Ile | Ala | Pro | Ser | Asn | Arg | Gln | Lys | Gln | Gln | Met | Ile | Leu | Asn | Gly |
| | | | 245 | | | | | 250 | | | | | 255 | | |

| Gln | Phe | Ser | Phe | Asp | Glu | Lys | Xaa | Trp | Lys | Asn | Ile | Ser | Ser | Ser | Ala |
| | | 260 | | | | | 265 | | | | | 270 | | | |

| Lys | Gln | Leu | Ile | Ser | Ser | Leu | Leu | Lys | Val | Asp | Pro | Asn | Met | Arg | Pro |
| | 275 | | | | | 280 | | | | | 285 | | | | |

| Thr | Ala | Gln | Glu | Ile | Leu | Glu | His | Pro | Trp | Val | Thr | Gly | Asp | Leu | Ala |
| | 290 | | | | | 295 | | | | | 300 | | | | |

| Lys | Gln | Glu | Gln | Met | Asp | Ala | Glu | Ile | Val | Ser | Arg | Leu | Gln | Ser | Phe |
| 305 | | | | | 310 | | | | | 315 | | | | | 320 |

| Asn | Ala | Arg | Arg | Lys | Phe | Arg | Ala | Ala | Ala | Met | Ala | Ser | Ile | Leu | Ser |
| | | | 325 | | | | | 330 | | | | | 335 | | |

| Ser | Ser | Phe | Ser | Leu | Arg | Thr | Lys | Lys | Leu | Lys | Lys | Leu | Val | Gly | Ser |
| | | 340 | | | | | 345 | | | | | 350 | | | |

| Tyr | Asp | Leu | Lys | Pro | Glu | Glu | Leu | Glu | Asn | Leu | Ser | His | Asn | Phe | Lys |
| | | 355 | | | | | 360 | | | | | 365 | | | |

| Lys | Ile | Cys | Lys | Asn | Gly | Glu | Asn | Ser | Thr | Leu | Leu | Glu | Phe | Glu | Glu |
| | 370 | | | | | 375 | | | | | 380 | | | | |

| Val | Leu | Lys | Ala | Met | Glu | Met | Ser | Ser | Leu | Val | Pro | Leu | Ala | Pro | Arg |

```
                385                 390                 395                 400
Ile Phe Asp Leu Phe Asp Asn Asn Arg Asp Gly Thr Val Asp Met Arg
                    405                 410                 415

Glu Ile Ile Gly Gly Phe Ser Ser Leu Lys Tyr Ser Gln Gly Asp Asp
                420                 425                 430

Ala Leu Arg Leu Cys Phe Gln Val Tyr Asp Thr Asp Arg Ser Gly Cys
            435                 440                 445

Ile Ser Lys Glu Glu Val Glu Ser Met Leu Arg Ala Leu Pro Glu Asp
        450                 455                 460

Cys Leu Pro Ile Asn Ile Thr Glu Pro Gly Lys Leu Asp Glu Ile Phe
465                 470                 475                 480

Asp Leu Met Asp Ala Asn Ser Asp Gly Lys Val Thr Phe Asp Glu Phe
                485                 490                 495

Lys Ala Ala Met Gln Arg Asp Ser Ser Leu Gln Asp Val Val Leu Ser
                500                 505                 510

Ser Leu Arg Pro Asn
            515

<210> SEQ ID NO 11
<211> LENGTH: 520
<212> TYPE: PRT
<213> ORGANISM: Lilium longiflorum
<220> FEATURE:
<221> NAME/KEY: MISC_FEATURE
<222> LOCATION: (267)..(267)
<223> OTHER INFORMATION: Xaa can be any naturally occurring amino acid
      excluding Thr or Ser

<400> SEQUENCE: 11

Met Ser Arg His Glu Ser Arg Lys Leu Ser Asp Asp Tyr Glu Val Val
1               5                   10                  15

Asp Val Leu Gly Lys Gly Gly Phe Ser Val Val Arg Arg Gly Ile Ser
            20                  25                  30

Lys Ser Arg Gly Lys Asn Asn Asp Val Ala Ile Lys Thr Leu Arg Arg
        35                  40                  45

Tyr Gly Tyr Thr Leu Pro Gly Ala Gln Arg Ser Gln Pro Gly Gln Arg
    50                  55                  60

Gly Leu Ser Pro Leu Gly Met Pro Thr Leu Lys Gln Val Ser Val Ser
65                  70                  75                  80

Asp Ala Leu Leu Thr Asn Glu Ile Leu Val Met Arg Arg Ile Val Glu
                85                  90                  95

Asp Val Ser Pro His Pro Asn Val Ile His Leu His Asp Val Tyr Glu
            100                 105                 110

Asp Ala Asn Gly Val His Leu Val Leu Glu Leu Cys Ser Gly Gly Glu
        115                 120                 125

Leu Phe Asp Arg Ile Val Ala Gln Asp Arg Tyr Ser Glu Ser Glu Ala
    130                 135                 140

Ala Glu Val Val Gln Gln Ile Ala Ser Gly Leu Ala Ala Leu His Lys
145                 150                 155                 160

Ser Thr Ile Ile His Arg Asp Leu Lys Pro Glu Asn Cys Leu Phe Leu
                165                 170                 175

Asn Gln Glu Lys Arg Ser Thr Leu Lys Ile Met Asp Phe Gly Leu Ser
            180                 185                 190

Ser Val Glu Asp Phe Thr Asp Pro Ile Val Ala Leu Phe Gly Ser Ile
        195                 200                 205

Asp Tyr Val Ser Pro Glu Ala Leu Ser Gln Arg Gln Val Ser Ser Ala
    210                 215                 220
```

```
Ser Asp Met Trp Ser Leu Gly Val Ile Leu Tyr Ile Leu Leu Ser Gly
225                 230                 235                 240

Cys Pro Pro Phe His Ala Pro Ser Asn Arg Glu Lys Gln Gln Arg Ile
            245                 250                 255

Leu Ala Gly Asp Phe Ser Phe Glu Glu His Xaa Trp Lys Thr Ile Thr
        260                 265                 270

Ser Ser Ala Lys Asp Leu Ile Ser Ser Leu Leu Ser Val Asp Pro Tyr
    275                 280                 285

Lys Arg Pro Thr Ala Asn Asp Leu Leu Lys His Pro Trp Val Ile Gly
290                 295                 300

Asp Ser Ala Lys Gln Glu Leu Ile Glu Pro Glu Val Val Ser Arg Leu
305                 310                 315                 320

Arg Ser Phe Asn Ala Arg Arg Lys Leu Arg Ala Ala Ile Ala Ser
            325                 330                 335

Val Leu Ser Ser Lys Val Leu Leu Arg Thr Lys Lys Leu Lys Asn Leu
        340                 345                 350

Leu Gly Ser His Asp Met Lys Ser Glu Glu Leu Glu Asn Leu Arg Ala
        355                 360                 365

His Phe Lys Arg Ile Cys Ala Asn Gly Asp Asn Ala Thr Leu Pro Glu
        370                 375                 380

Phe Glu Glu Val Leu Lys Ala Met Lys Met Asn Ser Leu Ile Pro Leu
385                 390                 395                 400

Ala Pro Arg Val Phe Asp Leu Phe Asp Asn Asn Arg Asp Gly Thr Ile
            405                 410                 415

Asp Met Arg Glu Ile Leu Cys Gly Leu Ser Asn Leu Arg Asn Ser Gln
        420                 425                 430

Gly Asp Asp Ala Leu Gln Leu Cys Phe Gln Met Tyr Asp Ala Asp Arg
        435                 440                 445

Ser Gly Cys Ile Ser Lys Glu Glu Leu Ala Ser Met Leu Arg Ala Leu
    450                 455                 460

Pro Glu Asp Cys Val Pro Ala Asp Ile Thr Glu Pro Gly Lys Leu Asp
465                 470                 475                 480

Glu Ile Phe Asp Gln Met Asp Ala Asn Ser Asp Gly Val Val Thr Phe
            485                 490                 495

Asp Glu Phe Lys Ala Ala Met Gln Arg Asp Ser Ser Leu Gln Asp Val
        500                 505                 510

Val Leu Ser Ser Leu Arg Thr Ile
        515                 520

<210> SEQ ID NO 12
<211> LENGTH: 3384
<212> TYPE: DNA
<213> ORGANISM: Oryza sativa
<220> FEATURE:
<221> NAME/KEY: exon
<222> LOCATION: (1)..(707)
<220> FEATURE:
<221> NAME/KEY: Intron
<222> LOCATION: (708)..(789)
<220> FEATURE:
<221> NAME/KEY: exon
<222> LOCATION: (790)..(845)
<220> FEATURE:
<221> NAME/KEY: Intron
<222> LOCATION: (846)..(1741)
<220> FEATURE:
<221> NAME/KEY: exon
<222> LOCATION: (1742)..(1851)
<220> FEATURE:
<221> NAME/KEY: Intron
```

```
<222> LOCATION: (1852)..(1946)
<220> FEATURE:
<221> NAME/KEY: exon
<222> LOCATION: (1947)..(2179)
<220> FEATURE:
<221> NAME/KEY: Intron
<222> LOCATION: (2180)..(2620)
<220> FEATURE:
<221> NAME/KEY: exon
<222> LOCATION: (2621)..(2828)
<220> FEATURE:
<221> NAME/KEY: Intron
<222> LOCATION: (2829)..(3017)
<220> FEATURE:
<221> NAME/KEY: exon
<222> LOCATION: (3018)..(3078)
<220> FEATURE:
<221> NAME/KEY: Intron
<222> LOCATION: (3079)..(3208)
<220> FEATURE:
<221> NAME/KEY: exon
<222> LOCATION: (3209)..(3384)

<400> SEQUENCE: 12 atg tcc aag act gag agc aga aag ttg tcc gat gac tat gaa gtt gtg        48
Met Ser Lys Thr Glu Ser Arg Lys Leu Ser Asp Asp Tyr Glu Val Val
1               5                   10                  15 gat gtt ctt ggc cgg ggc ggg ttc tca ata gta agg agg gga gtg agc        96
Asp Val Leu Gly Arg Gly Gly Phe Ser Ile Val Arg Arg Gly Val Ser
                20                  25                  30 aag tct gaa gag aag acc cag gtt gcc atc aag act ctg agg agg ctc       144
Lys Ser Glu Glu Lys Thr Gln Val Ala Ile Lys Thr Leu Arg Arg Leu
            35                  40                  45 ggc ccg gcg atg gcg ggt atg aag cag ggg aca aag ccc gtg ccc ggc       192
Gly Pro Ala Met Ala Gly Met Lys Gln Gly Thr Lys Pro Val Pro Gly
        50                  55                  60 tcc ggc ctg ccg atg tgg aaa cag gta tcg atc tcc gac gcg ctg ctg       240
Ser Gly Leu Pro Met Trp Lys Gln Val Ser Ile Ser Asp Ala Leu Leu
65                  70                  75                  80 acg aac gag ata ctc gtc atg agg agg ata gtg gag agc gtt gcg cca       288
Thr Asn Glu Ile Leu Val Met Arg Arg Ile Val Glu Ser Val Ala Pro
                85                  90                  95 cat cct aat gtc atc aac ctg cat gat gtg tat gaa gat gtg cat ggt       336
His Pro Asn Val Ile Asn Leu His Asp Val Tyr Glu Asp Val His Gly
                100                 105                 110 gtg cac ctc gtc ctt gag ctg tgc tcg ggt ggt gag ctt ttt gat cgg       384
Val His Leu Val Leu Glu Leu Cys Ser Gly Gly Glu Leu Phe Asp Arg
            115                 120                 125 att gtg ggg cgt gac cgg tac tcg gag ttc gat gcg gcc tgc gtc att       432
Ile Val Gly Arg Asp Arg Tyr Ser Glu Phe Asp Ala Ala Cys Val Ile
        130                 135                 140 cgt cag att gct agc ggg ctg gag gct ctt cat aag gca agc att gta       480
Arg Gln Ile Ala Ser Gly Leu Glu Ala Leu His Lys Ala Ser Ile Val
145                 150                 155                 160 cac agg gac ctg aag ccg gag aat tgt ctg ttc tct gac aaa gat gag       528
His Arg Asp Leu Lys Pro Glu Asn Cys Leu Phe Ser Asp Lys Asp Glu
                165                 170                 175 aag tcc aca ctg aag atc atg gat ttt ggt ttg agt tct gtc gaa gat       576
Lys Ser Thr Leu Lys Ile Met Asp Phe Gly Leu Ser Ser Val Glu Asp
                180                 185                 190 ttc agt gac cca atc gtc gcg ctg ttt ggg tca ata gat tat gtt tca       624
Phe Ser Asp Pro Ile Val Ala Leu Phe Gly Ser Ile Asp Tyr Val Ser
            195                 200                 205 ccg gag gct cta tcc agg cag gag gtt tca gct gct agt gat atg tgg       672
Pro Glu Ala Leu Ser Arg Gln Glu Val Ser Ala Ala Ser Asp Met Trp
        210                 215                 220
```

```
tct gtt ggg gta att ctg tac att ctt tta tct gg  gtatgttggc               717
Ser Val Gly Val Ile Leu Tyr Ile Leu Leu Ser Gly
225                 230                 235 cattttcttg ttatagttcc cttgattagg attattttcg tagttttaag cctggtagtt        777
tgtgtatttc ag a tgc cca cca ttt cat gct gca acc aat cga gaa aag          826
              Cys Pro Pro Phe His Ala Ala Thr Asn Arg Glu Lys
                                240                 245 cag caa agg atc ctg caa g taagtttcct gagctaactc tggtcaaatt               875
Gln Gln Arg Ile Leu Gln
    250 gttgcttcaa tggtgttcaa aatggtttgg aatattctgg ttcgcatttg acgataccta        935 ttaaacactt cgggcaattt tagtggaagc agaatcatta taagtattct gatcaagatg        995 atttataagt atctttgcat tttctaatga agcagaatta ttataattct ggcccgtgaa       1055 tgtgagggtg tttttcttgc aaaaaatgga attttggtga gagttacatg tagctgacct       1115 cgagtgtgag tcgccatac ggttttccag tcccaaatta tgtgttgggc atttgattca        1175 ctctaaaatt tcagcatgag tgtgaagttg ttagcctttt atcagtgggt ttgcagcaaa       1235 tgacattgca tagtttggag atctgcctgc caatcattgc tgaaatgtcg tcttttggta       1295 gttgttagca cttcagttta tacctgcatt gtcctatatt ttgtccagtt ctagtagaaa       1355 aagttgccct gagatgtcaa atcaatagca gttggccagt agctaactag accttacatt       1415 ttactgaaaa ggtgtaaaag aatgttctct tccacaaaag acacatggat tggattgtac       1475 attttccaat gaaaaacacg aactgagtca gtatggatat ggggctactg gctagtcaa        1535 atgttgttca gtaaaccact gaaaaaataa ataaactgtg ccgtttgttt ctgaagaatt       1595 atgggttcca ttatcaatag tgcctttgaa taacatgact ataagaggag gatttgtagt       1655 ccttgtgtta ggcaccaatt attcgaaaat gcctgtatta atcaggaact tgctctaatg       1715 gcatataatt tgtgtgcttc ttcagg gt  gaa ttc agt ttt cag gac cac ata        1767
                                Gly Glu Phe Ser Phe Gln Asp His Ile
                                              255                 260 tgg aaa aca ata tct tca tcc gcg aaa gat ttg att tcg cgc ctt ctt         1815
Trp Lys Thr Ile Ser Ser Ser Ala Lys Asp Leu Ile Ser Arg Leu Leu
    265                 270                 275 tct gtt caa cct tac aaa agg cca aca gca agt gat gtctgtctca              1861
Ser Val Gln Pro Tyr Lys Arg Pro Thr Ala Ser Asp
280                 285                 290 tatgctccct tttcagcata ttaccatgtt agctaagata ctataactgt tcttaatttg       1921
aatatcatgt gtcatttgaa accag ctt ctg agg cat cct tgg gtg att gga         1973
                            Leu Leu Arg His Pro Trp Val Ile Gly
                                            295                 300 gac tgc gcc aag caa gat ctc atg gat gca gag gtc gtc tca aaa ctg         2021
Asp Cys Ala Lys Gln Asp Leu Met Asp Ala Glu Val Val Ser Lys Leu
                305                 310                 315 caa aag ttc aat gct aga agg aaa ttg cgg gca gct gcg ata gcc agc         2069
Gln Lys Phe Asn Ala Arg Arg Lys Leu Arg Ala Ala Ala Ile Ala Ser
            320                 325                 330 gtt ttg agc tgc aaa gtg gca ttg agg act aaa agg ctg aga aat ctt         2117
Val Leu Ser Cys Lys Val Ala Leu Arg Thr Lys Arg Leu Arg Asn Leu
        335                 340                 345 tta gga acc cat gac ctt acc tca gag gag ctg gat aat ctg cgg ctt         2165
Leu Gly Thr His Asp Leu Thr Ser Glu Glu Leu Asp Asn Leu Arg Leu
    350                 355                 360 cat ttt gga cga at  gtgagtatca tgacttgatc agcctaaaac ctcttgtgta         2219
His Phe Gly Arg Ile
365
```

```
attactagaa ttttgggact agcatttctc agttagtaat ttgaggaaca ctacagttgc   2279
tttaaggggg agtcatatat ccttgtcttc tctgaaaaca aatgttttt tttccaacac    2339 tgaagaagtc ccaattttgc aggagtatat ttgcacatat catatatcat gtgcagccca   2399
ttttattagg attttaggag tagaagatat gtgctatgat gaactgtgaa attaacaccg   2459
aaaagattta taagcagaaa gcggtagcct tttttccctt tgccagagaa gcttcagaag   2519
ttcagatttc tcgtaaaacc ttcatagttt taggatttaa acatgacaca tatgatgttc   2579
caatcgaaaa gtataacact aagcaagtgc tctttatgca g a tgt gca gat gga     2633
                                              Cys Ala Asp Gly
                                                      370 gaa aac gcc act ctg tca gag ttt gag cag gtg ctg aga gca atg aaa   2681
Glu Asn Ala Thr Leu Ser Glu Phe Glu Gln Val Leu Arg Ala Met Lys
    375                 380                 385 atg gac tca ctg att ccc cta gct ccc cgc gta ttc gat ctg ttc gac   2729
Met Asp Ser Leu Ile Pro Leu Ala Pro Arg Val Phe Asp Leu Phe Asp
390                 395                 400                 405 aac aac cgt gat gga acc gtc gac atg aga gag atc ctg tgt ggg ttc   2777
Asn Asn Arg Asp Gly Thr Val Asp Met Arg Glu Ile Leu Cys Gly Phe
                410                 415                 420 tcc agc ctc agg aac tca cga ggc gat gat gct ctt cgc ttg tgc ttc   2825
Ser Ser Leu Arg Asn Ser Arg Gly Asp Asp Ala Leu Arg Leu Cys Phe
            425                 430                 435 cag gtaaaaattt ccaaatgcac tcgactcaaa ctgaagtggc agcccttcca         2878
Gln atttatgtac aggaatatca gaaacattgc atgatatcat atcatacata acttcaaatt   2938
caattaaaat tcataacaag agaggtattt cagcatctga tcatgagcac acaaaaaaaa   2998
actgcatttt tctttcag atg tac gac gct gat cgg tca ggc tgc atc agc    3050
                    Met Tyr Asp Ala Asp Arg Ser Gly Cys Ile Ser
                                440                 445 aag gaa gag ctg gca tca atg ctc cga g taagaactcc taaaaaagga         3098
Lys Glu Glu Leu Ala Ser Met Leu Arg
450                 455 aaaccaaatc tttgctcttc ttgagatggc ttgttcatgt ctcttttcaa gttttgagtt   3158
gaaaatctga cgagctgctg ttcatctgaa cttttggtgat cctcacaagg cg ttg      3213
                                                          Ala Leu
                                                              460 ccg gag gag tgc ctg cca ggc gac ata acg gag ccg ggg aag ctg gac   3261
Pro Glu Glu Cys Leu Pro Gly Asp Ile Thr Glu Pro Gly Lys Leu Asp
                465                 470                 475 gag gtg ttc gac cag atg gac gcc gac agc gac ggc aag gtc acc ttc   3309
Glu Val Phe Asp Gln Met Asp Ala Asp Ser Asp Gly Lys Val Thr Phe
            480                 485                 490 gac gag ttc aag gcc gcc atg aac aag gac agc gcc ctc cag gac gtc   3357
Asp Glu Phe Lys Ala Ala Met Asn Lys Asp Ser Ala Leu Gln Asp Val
        495                 500                 505 ctc ctc tcc tcc ctc cgc cca cag tag                                3384
Leu Leu Ser Ser Leu Arg Pro Gln
    510                 515

<210> SEQ ID NO 13
<211> LENGTH: 1551
<212> TYPE: DNA
<213> ORGANISM: Oryza sativa
<220> FEATURE:
<221> NAME/KEY: CDS
<222> LOCATION: (1)..(1551)

<400> SEQUENCE: 13
```

```
atg tcc aag act gag agc aga aag ttg tcc gat gac tat gaa gtt gtg      48
Met Ser Lys Thr Glu Ser Arg Lys Leu Ser Asp Asp Tyr Glu Val Val
1               5                   10                  15 gat gtt ctt ggc cgg ggc ggg ttc tca ata gta agg agg gga gtg agc      96
Asp Val Leu Gly Arg Gly Gly Phe Ser Ile Val Arg Arg Gly Val Ser
            20                  25                  30 aag tct gaa gag aag acc cag gtt gcc atc aag act ctg agg agg ctc     144
Lys Ser Glu Glu Lys Thr Gln Val Ala Ile Lys Thr Leu Arg Arg Leu
        35                  40                  45 ggc ccg gcg atg gcg ggt atg aag cag ggg aca aag ccc gtg ccc ggc     192
Gly Pro Ala Met Ala Gly Met Lys Gln Gly Thr Lys Pro Val Pro Gly
    50                  55                  60 tcc ggc ctg ccg atg tgg aaa cag gta tcg atc tcc gac gcg ctg ctg     240
Ser Gly Leu Pro Met Trp Lys Gln Val Ser Ile Ser Asp Ala Leu Leu
65              70                  75                  80 acg aac gag ata ctc gtc atg agg agg ata gtg gag agc gtt gcg cca     288
Thr Asn Glu Ile Leu Val Met Arg Arg Ile Val Glu Ser Val Ala Pro
                85                  90                  95 cat cct aat gtc atc aac ctg cat gat gtg tat gaa gat gtg cat ggt     336
His Pro Asn Val Ile Asn Leu His Asp Val Tyr Glu Asp Val His Gly
            100                 105                 110 gtg cac ctc gtc ctt gag ctg tgc tcg ggt ggt gag ctt ttt gat cgg     384
Val His Leu Val Leu Glu Leu Cys Ser Gly Gly Glu Leu Phe Asp Arg
        115                 120                 125 att gtg ggg cgt gac cgg tac tcg gag ttc gat gcg gcc tgc gtc att     432
Ile Val Gly Arg Asp Arg Tyr Ser Glu Phe Asp Ala Ala Cys Val Ile
    130                 135                 140 cgt cag att gct agc ggg ctg gag gct ctt cat aag gca agc att gta     480
Arg Gln Ile Ala Ser Gly Leu Glu Ala Leu His Lys Ala Ser Ile Val
145                 150                 155                 160 cac agg gac ctg aag ccg gag aat tgt ctg ttc tct gac aaa gat gag     528
His Arg Asp Leu Lys Pro Glu Asn Cys Leu Phe Ser Asp Lys Asp Glu
                165                 170                 175 aag tcc aca ctg aag atc atg gat ttt ggt ttg agt tct gtc gaa gat     576
Lys Ser Thr Leu Lys Ile Met Asp Phe Gly Leu Ser Ser Val Glu Asp
            180                 185                 190 ttc agt gac cca atc gtc gcg ctg ttt ggg tca ata gat tat gtt tca     624
Phe Ser Asp Pro Ile Val Ala Leu Phe Gly Ser Ile Asp Tyr Val Ser
        195                 200                 205 ccg gag gct cta tcc agg cag gag gtt tca gct gct agt gat atg tgg     672
Pro Glu Ala Leu Ser Arg Gln Glu Val Ser Ala Ala Ser Asp Met Trp
    210                 215                 220 tct gtt ggg gta att ctg tac att ctt tta tct gga tgc cca cca ttt     720
Ser Val Gly Val Ile Leu Tyr Ile Leu Leu Ser Gly Cys Pro Pro Phe
225                 230                 235                 240 cat gct gca acc aat cga gaa aag cag caa agg atc ctg caa ggt gaa     768
His Ala Ala Thr Asn Arg Glu Lys Gln Gln Arg Ile Leu Gln Gly Glu
                245                 250                 255 ttc agt ttt cag gac cac ata tgg aaa aca ata tct tca tcc gcg aaa     816
Phe Ser Phe Gln Asp His Ile Trp Lys Thr Ile Ser Ser Ser Ala Lys
            260                 265                 270 gat ttg att tcg cgc ctt ctt tct gtt caa cct tac aaa agg cca aca     864
Asp Leu Ile Ser Arg Leu Leu Ser Val Gln Pro Tyr Lys Arg Pro Thr
        275                 280                 285 gca agt gat ctt ctg agg cat cct tgg gtg att gga gac tgc gcc aag     912
Ala Ser Asp Leu Leu Arg His Pro Trp Val Ile Gly Asp Cys Ala Lys
    290                 295                 300 caa gat ctc atg gat gca gag gtc gtc tca aaa ctg caa aag ttc aat     960
Gln Asp Leu Met Asp Ala Glu Val Val Ser Lys Leu Gln Lys Phe Asn
305                 310                 315                 320
```

```
gct aga agg aaa ttg cgg gca gct gcg ata gcc agc gtt ttg agc tgc     1008
Ala Arg Arg Lys Leu Arg Ala Ala Ala Ile Ala Ser Val Leu Ser Cys
            325                 330                 335 aaa gtg gca ttg agg act aaa agg ctg aga aat ctt tta gga acc cat     1056
Lys Val Ala Leu Arg Thr Lys Arg Leu Arg Asn Leu Leu Gly Thr His
        340                 345                 350 gac ctt acc tca gag gag ctg gat aat ctg cgg ctt cat ttt gga cga     1104
Asp Leu Thr Ser Glu Glu Leu Asp Asn Leu Arg Leu His Phe Gly Arg
    355                 360                 365 ata tgt gca gat gga gaa aac gcc act ctg tca gag ttt gag cag gtg     1152
Ile Cys Ala Asp Gly Glu Asn Ala Thr Leu Ser Glu Phe Glu Gln Val
370                 375                 380 ctg aga gca atg aaa atg gac tca ctg att ccc cta gct ccc cgc gta     1200
Leu Arg Ala Met Lys Met Asp Ser Leu Ile Pro Leu Ala Pro Arg Val
385                 390                 395                 400 ttc gat ctg ttc gac aac aac cgt gat gga acc gtc gac atg aga gag     1248
Phe Asp Leu Phe Asp Asn Asn Arg Asp Gly Thr Val Asp Met Arg Glu
            405                 410                 415 atc ctg tgt ggg ttc tcc agc ctc agg aac tca cga ggc gat gat gct     1296
Ile Leu Cys Gly Phe Ser Ser Leu Arg Asn Ser Arg Gly Asp Asp Ala
        420                 425                 430 ctt cgc ttg tgc ttc cag atg tac gac gct gat cgg tca ggc tgc atc     1344
Leu Arg Leu Cys Phe Gln Met Tyr Asp Ala Asp Arg Ser Gly Cys Ile
    435                 440                 445 agc aag gaa gag ctg gca tca atg ctc cga gcg ttg ccg gag gag tgc     1392
Ser Lys Glu Glu Leu Ala Ser Met Leu Arg Ala Leu Pro Glu Glu Cys
450                 455                 460 ctg cca ggc gac ata acg gag ccg ggg aag ctg gac gag gtg ttc gac     1440
Leu Pro Gly Asp Ile Thr Glu Pro Gly Lys Leu Asp Glu Val Phe Asp
465                 470                 475                 480 cag atg gac gcc gac agc gac ggc aag gtc acc ttc gac gag ttc aag     1488
Gln Met Asp Ala Asp Ser Asp Gly Lys Val Thr Phe Asp Glu Phe Lys
            485                 490                 495 gcc gcc atg aac aag gac agc gcc ctc cag gac gtc ctc ctc tcc tcc     1536
Ala Ala Met Asn Lys Asp Ser Ala Leu Gln Asp Val Leu Leu Ser Ser
        500                 505                 510 ctc cgc cca cag tag                                                 1551
Leu Arg Pro Gln
    515
```

<210> SEQ ID NO 14
<211> LENGTH: 516
<212> TYPE: PRT
<213> ORGANISM: Oryza sativa

<400> SEQUENCE: 14

```
Met Ser Lys Thr Glu Ser Arg Lys Leu Ser Asp Asp Tyr Glu Val Val
1               5                   10                  15

Asp Val Leu Gly Arg Gly Gly Phe Ser Ile Val Arg Arg Gly Val Ser
            20                  25                  30

Lys Ser Glu Glu Lys Thr Gln Val Ala Ile Lys Thr Leu Arg Arg Leu
        35                  40                  45

Gly Pro Ala Met Ala Gly Met Lys Gln Gly Thr Lys Pro Val Pro Gly
    50                  55                  60

Ser Gly Leu Pro Met Trp Lys Gln Val Ser Ile Ser Asp Ala Leu Leu
65                  70                  75                  80

Thr Asn Glu Ile Leu Val Met Arg Arg Ile Val Glu Ser Val Ala Pro
                85                  90                  95

His Pro Asn Val Ile Asn Leu His Asp Val Tyr Glu Asp Val His Gly
```

```
                100                 105                 110
    Val His Leu Val Leu Glu Leu Cys Ser Gly Gly Glu Leu Phe Asp Arg
                115                 120                 125

Ile Val Gly Arg Asp Arg Tyr Ser Glu Phe Asp Ala Ala Cys Val Ile
                130                 135                 140

Arg Gln Ile Ala Ser Gly Leu Glu Ala Leu His Lys Ala Ser Ile Val
    145                 150                 155                 160

His Arg Asp Leu Lys Pro Glu Asn Cys Leu Phe Ser Lys Asp Glu
                165                 170                 175

Lys Ser Thr Leu Lys Ile Met Asp Phe Gly Leu Ser Ser Val Glu Asp
                180                 185                 190

Phe Ser Asp Pro Ile Val Ala Leu Phe Gly Ser Ile Asp Tyr Val Ser
                195                 200                 205

Pro Glu Ala Leu Ser Arg Gln Glu Val Ser Ala Ala Ser Asp Met Trp
                210                 215                 220

Ser Val Gly Val Ile Leu Tyr Ile Leu Leu Ser Gly Cys Pro Pro Phe
    225                 230                 235                 240

His Ala Ala Thr Asn Arg Glu Lys Gln Gln Arg Ile Leu Gln Gly Glu
                245                 250                 255

Phe Ser Phe Gln Asp His Ile Trp Lys Thr Ile Ser Ser Ala Lys
                260                 265                 270

Asp Leu Ile Ser Arg Leu Leu Ser Val Gln Pro Tyr Lys Arg Pro Thr
                275                 280                 285

Ala Ser Asp Leu Leu Arg His Pro Trp Val Ile Gly Asp Cys Ala Lys
                290                 295                 300

Gln Asp Leu Met Asp Ala Glu Val Val Ser Lys Leu Gln Lys Phe Asn
    305                 310                 315                 320

Ala Arg Arg Lys Leu Arg Ala Ala Ala Ile Ala Ser Val Leu Ser Cys
                325                 330                 335

Lys Val Ala Leu Arg Thr Lys Arg Leu Arg Asn Leu Leu Gly Thr His
                340                 345                 350

Asp Leu Thr Ser Glu Glu Leu Asp Asn Leu Arg Leu His Phe Gly Arg
                355                 360                 365

Ile Cys Ala Asp Gly Glu Asn Ala Thr Leu Ser Glu Phe Glu Gln Val
                370                 375                 380

Leu Arg Ala Met Lys Met Asp Ser Leu Ile Pro Leu Ala Pro Arg Val
    385                 390                 395                 400

Phe Asp Leu Phe Asp Asn Asn Arg Asp Gly Thr Val Asp Met Arg Glu
                405                 410                 415

Ile Leu Cys Gly Phe Ser Ser Leu Arg Asn Ser Arg Gly Asp Asp Ala
                420                 425                 430

Leu Arg Leu Cys Phe Gln Met Tyr Asp Ala Asp Arg Ser Gly Cys Ile
                435                 440                 445

Ser Lys Glu Glu Leu Ala Ser Met Leu Arg Ala Leu Pro Glu Glu Cys
                450                 455                 460

Leu Pro Gly Asp Ile Thr Glu Pro Gly Lys Leu Asp Glu Val Phe Asp
    465                 470                 475                 480

Gln Met Asp Ala Asp Ser Asp Gly Lys Val Thr Phe Asp Glu Phe Lys
                485                 490                 495

Ala Ala Met Asn Lys Asp Ser Ala Leu Gln Asp Val Leu Leu Ser Ser
                500                 505                 510

Leu Arg Pro Gln
                515
```

```
<210> SEQ ID NO 15
<211> LENGTH: 504
<212> TYPE: PRT
<213> ORGANISM: Physcomitrella patens
<220> FEATURE:
<221> NAME/KEY: MISC_FEATURE
<222> LOCATION: (252)..(252)
<223> OTHER INFORMATION: Xaa can be any naturally occurring amino acid
      excluding Thr or Ser

<400> SEQUENCE: 15
```

Met Ser Asp Pro Tyr Gly Arg Arg Leu Leu Val Asp Asp Phe His Val
1               5                   10                  15

Gly Pro Val Leu Gly Thr Gly Gly Phe Ser Val Val Arg Ala Gly Val
            20                  25                  30

Arg Lys Gln Asp Asn Leu Gln Val Ala Ile Lys Thr Leu Lys Lys Phe
        35                  40                  45

Gly Tyr Gly Arg Gly Asp His Gly Arg Pro Gly Ala Gln Met Ser Gln
    50                  55                  60

Ala Glu Ala Leu Val Lys Asn Glu Ile Met Val Met Met Arg Ile Val
65                  70                  75                  80

Asp Glu Val Ser Pro His Pro Asn Val Ile His Leu Ile Asp Val Tyr
                85                  90                  95

Glu Asp Asp Gly Ala Val His Leu Val Leu Glu Leu Cys Arg Gly Gly
            100                 105                 110

Glu Leu Phe Asp Arg Ile Val Gln His Glu Arg Tyr Ser Glu Arg Asp
        115                 120                 125

Ala Ala Lys Val Val Arg Gln Ile Ala Ser Gly Leu Ala Ala Leu His
    130                 135                 140

Gln Ala Gln Ile Val His Arg Asp Leu Lys Pro Glu Asn Cys Leu Tyr
145                 150                 155                 160

Val Asn Pro Leu Ala Glu Ala Pro Leu Lys Ile Met Asp Phe Gly Leu
                165                 170                 175

Ser Tyr Ile His His Asn Thr Asn Ser Ile Val Gly Ile Phe Gly Ser
            180                 185                 190

Ile Asp Tyr Met Ala Pro Glu Gln Leu Ser Leu Ser Gly Ile Met Pro
        195                 200                 205

Ala Asn Asp Met Trp Ser Leu Gly Val Ile Leu Tyr Ile Leu Leu Cys
    210                 215                 220

Gly Tyr Pro Pro Phe Arg Ala Arg Ser Ser Arg Asp Lys Gln Met Gln
225                 230                 235                 240

Ile Leu Thr Gly Ser Tyr Ser Met Glu Glu Glu Xaa Trp Arg Gly Ile
                245                 250                 255

Ser His Glu Ala Lys Gln Leu Ile Arg Arg Leu Leu Ser Val Asp Pro
            260                 265                 270

Phe Ala Arg Pro Thr Ala Arg Glu Leu Leu Ser His Pro Trp Val Ser
        275                 280                 285

Gly Asp Ile Ala Asn Arg Asp Leu Leu His Lys Asp Val Phe Met Arg
    290                 295                 300

Leu Gln His Phe Asn Ala Arg Arg Lys Phe Arg Ala Thr Ala Tyr Ala
305                 310                 315                 320

Ser Ile Val Arg Thr Lys Phe Leu Leu Arg Thr Arg Tyr Leu Lys Glu
                325                 330                 335

Leu Leu Gly Asp Arg Val Leu Thr Asp Ser Glu Leu Glu Ala Leu Arg
            340                 345                 350

Val Asn Phe Met Arg Ile Ser Ser Asn Gly Gln Thr Ala Thr Leu Lys

```
                      355                 360                 365
Glu Phe Glu Glu Val Leu Arg Ser Ile Asn Leu His Cys Phe Val Pro
    370                 375                 380

Leu Ala Pro Arg Ile Phe Glu Leu Phe Asp Tyr Asn His Asp Gly Gly
385                 390                 395                 400

Ile Asp Leu Arg Glu Val Val Cys Gly Phe Ser Leu Leu Arg Thr Ser
                405                 410                 415

His Leu Asp Asp Ala Leu Gln Met Cys Phe Lys Ile Tyr Asp Arg Asp
            420                 425                 430

Asp Ser Gly Tyr Ile Ser Lys Gly Glu Leu Ala Arg Val Leu Gly Ala
        435                 440                 445

Leu Pro Glu Asp Tyr Leu Pro Ala Asp Ile Ser Gln Val Gln Met Asp
    450                 455                 460

Asp Ile Phe Glu His Val Asp Thr Asp Ser Asp Gly Arg Ile Ser Tyr
465                 470                 475                 480

Gln Glu Phe Arg Arg Ala Leu Ser Leu Gln Asp Ala Val Met Asn His
                485                 490                 495

Phe Arg Met Glu Gly Gln Val Gln
            500
```

```
<210> SEQ ID NO 16
<211> LENGTH: 6485
<212> TYPE: DNA
<213> ORGANISM: Lotus japonicus
<220> FEATURE:
<221> NAME/KEY: 5'UTR
<222> LOCATION: (1)..(323)
<220> FEATURE:
<221> NAME/KEY: exon
<222> LOCATION: (324)..(1036)
<220> FEATURE:
<221> NAME/KEY: Intron
<222> LOCATION: (1037)..(3265)
<220> FEATURE:
<221> NAME/KEY: exon
<222> LOCATION: (3266)..(3320)
<220> FEATURE:
<221> NAME/KEY: Intron
<222> LOCATION: (3321)..(3611)
<220> FEATURE:
<221> NAME/KEY: exon
<222> LOCATION: (3612)..(3722)
<220> FEATURE:
<221> NAME/KEY: Intron
<222> LOCATION: (3723)..(4114)
<220> FEATURE:
<221> NAME/KEY: exon
<222> LOCATION: (4115)..(4347)
<220> FEATURE:
<221> NAME/KEY: Intron
<222> LOCATION: (4348)..(4715)
<220> FEATURE:
<221> NAME/KEY: exon
<222> LOCATION: (4716)..(4923)
<220> FEATURE:
<221> NAME/KEY: Intron
<222> LOCATION: (4924)..(5593)
<220> FEATURE:
<221> NAME/KEY: exon
<222> LOCATION: (5594)..(5653)
<220> FEATURE:
<221> NAME/KEY: Intron
<222> LOCATION: (5654)..(5737)
<220> FEATURE:
<221> NAME/KEY: exon
<222> LOCATION: (5738)..(5914)
<220> FEATURE:
<221> NAME/KEY: 3'UTR
<222> LOCATION: (5915)..(6485)
```

```
<400> SEQUENCE: 16
ttttcaagtc ggctaaatag tgaatagaag aattttagag tacaaaatgg tagcagttga       60
ctctctctct gtcccttcta aaacagcccc taccagccat tgtttattct cttgtaccta      120
tctgaatttg cttcatattt tatgccataa actaatgcag aaactctcac aaaggctaat      180
gtcaacatca accattttca atacgcgttt tgtaggccga tcattgaaac ttgaagtcat      240
gttatattat acatacctct tctcattgat cattgaacat tttctgagtc tgaaaagatt      300
ccaatatttt caaacactct gcc atg gga tat gat caa acc aga aag ctc tct      353
                          Met Gly Tyr Asp Gln Thr Arg Lys Leu Ser
                            1               5                  10 gat gag tat gag att tca gag att cta gga aga ggt gga ttc tct gtt      401
Asp Glu Tyr Glu Ile Ser Glu Ile Leu Gly Arg Gly Gly Phe Ser Val
                15                  20                  25 gtc aga aaa gga acc aaa aaa tca ggc aat gag aaa acc caa gta gcc      449
Val Arg Lys Gly Thr Lys Lys Ser Gly Asn Glu Lys Thr Gln Val Ala
            30                  35                  40 atc aaa aca ctc aga agg tta ggt agt tct ccc tct ggg aca ggt ggt      497
Ile Lys Thr Leu Arg Arg Leu Gly Ser Ser Pro Ser Gly Thr Gly Gly
        45                  50                  55 gga cag aag agc aca gca act gtg atg ggg ttc cct tct ttg aga cag      545
Gly Gln Lys Ser Thr Ala Thr Val Met Gly Phe Pro Ser Leu Arg Gln
 60                  65                  70 gtt tca gtc tca gat gct ttg ctc acc aat gag att ctt gtg atg agg      593
Val Ser Val Ser Asp Ala Leu Leu Thr Asn Glu Ile Leu Val Met Arg
 75                  80                  85                  90 agg ata gtg gaa aac gtt tcg cca cat cca aac gtg att gat ctc tat      641
Arg Ile Val Glu Asn Val Ser Pro His Pro Asn Val Ile Asp Leu Tyr
                 95                 100                 105 gat gtg tgt gag gac tca aat ggg gtg cat ctt gtg ctg gag ctt tgt      689
Asp Val Cys Glu Asp Ser Asn Gly Val His Leu Val Leu Glu Leu Cys
            110                 115                 120 tct ggt ggg gag ctg ttt gat agg att gtt gca cag gat aag tat gct      737
Ser Gly Gly Glu Leu Phe Asp Arg Ile Val Ala Gln Asp Lys Tyr Ala
        125                 130                 135 gag acg gaa gct gcc gcg gtg gtt cgc cag att gcg gcg ggg cta gag      785
Glu Thr Glu Ala Ala Ala Val Val Arg Gln Ile Ala Ala Gly Leu Glu
    140                 145                 150 gcg gtt cac aag gct gac att gtt cac agg gat ttg aag cct gag aat      833
Ala Val His Lys Ala Asp Ile Val His Arg Asp Leu Lys Pro Glu Asn
155                 160                 165                 170 tgc ctt ttc ttg gat tcc agg aag gac tct cct ctc aag atc atg gac      881
Cys Leu Phe Leu Asp Ser Arg Lys Asp Ser Pro Leu Lys Ile Met Asp
                175                 180                 185 ttt ggg ttg agc tct gtt gag gag ttc act gac cct gtt gtt ggg ttg      929
Phe Gly Leu Ser Ser Val Glu Glu Phe Thr Asp Pro Val Val Gly Leu
            190                 195                 200 ttt gga tcc att gat tat gtt tca cca gag gct ctt tct caa ggg aag      977
Phe Gly Ser Ile Asp Tyr Val Ser Pro Glu Ala Leu Ser Gln Gly Lys
        205                 210                 215 atc act gcc aag agt gac atg tgg tct ctg gga gtg att cta tat atc     1025
Ile Thr Ala Lys Ser Asp Met Trp Ser Leu Gly Val Ile Leu Tyr Ile
    220                 225                 230 ttg ctc tct gg  gtatgttgtc tttcacttgt tgaaattgtt catattgtgt         1076
Leu Leu Ser Gly
235 tggttgctcc ccatccacct tttgcagagc ccatttggat acaagcttat tgatgtttat     1136 tgaagcttat ctactagaaa atgcactaaa taagcttcca caatactctt tggcttgcat     1196
```

-continued

```
ccaaacggct acttagtgca gtaaatatgg atgccaagaa ggaaattta gtttctcact      1256 tattaggtgg cattagtctt tgaaacttaa aaaaaaaaac ccactgataa catgctcgaa      1316
aatcattcta caattgatta tgaaaaatta attgttagaa tataatataa aagcattaaa      1376 gtgacctta cccaacagct taagcttttg ggattaagtg gttatttgac atggtatcac      1436
tagggatggc aacgggtagg atcgggcatg ggttttacaa ttaccaaacc caaacccaaa      1496
tcccagaacc caaacccaaa cccaaacaca aacccttatg ggcgataaaa tgaaattcat      1556
gcccaaatcc attgggtttc ggatttaccc gaaactcaaa cccaaaccca ttagttaggt      1616
agcaactcaa tccagaactt actttcatat aaaagaaaag tgaaattcat ataaagaaaa      1676
aaaaaacaaa tactattcat catcctcatc catcactaaa gtgagacaac aatagtttaa      1736
agtttacttt ctcaaacata caaaagtaca attaatcatc aaacactaag aacaaagttt      1796
ataaatatat atatgtatga gggttttttt gtaatttat gtttcgggta tctttgggtt      1856
cgggtttggg cggggtatgg gcatgaattt aactaatacc aaaatccaaa ctcataaatg      1916
gcttcagtaa cgggcaaaac tcaaacccaa acccaaatcc agtcaactcg attttgccc      1976 gtcaaatcgg atcgggtacc catgggtttg ggcaaaattt ccatccctag gtatcagagc      2036
ctctatgacc gagaggtcta gagttcgatc cttgctcccc tcactttcta attaaaaaag      2096
tggaatttaa ttaagcacat ggtaggtgga cctgtgcatt tatccacgct acaagcccaa      2156
agggctcttg cgtgaggagg cgtgttagaa tataatataa aaccattaaa gtgacccta      2216 cccaacagct taagcttttg ggataagtgg ttgtttgaca ttaatacttg agagaaactt      2276
atatgaatag cttctgaatg atgttccata attcattttg agaaagaaaa aaagctaatc      2336
caaacatgtg ttagaaaatg aacatgcttg atcgtgatga aataactttc cttaaagtat      2396
ttcaagcact ctctaaattt cgtcttagag tttggatgca agaatacca ggataatcag      2456 ccttgattcg agtttgcaca agactaatga aaactcgaaa tgaagagaag tgattttctg      2516
gaaaacagag gatatgattg tgtgttatga attctgaaca tggactctat ttataggcaa      2576
aacagaacaa tatataaggt tgcgacccct catatattgt gtctgttaac aacagtcgca      2636
aaaatcaaat tcaaaagag caaaaacaaa cggacgttac ggcaaccgcg tagccgtcgt      2696
tgcgtctaca agccgccact agcgcctcta cgcccacgcc tgtgacaccg gcgaggggtg      2756
gtgtgagtgg aatatgtgac ataaaagctt gggaccacca aactatgcac atgtggcact      2816
atatcctctt tttgtctctt tgttgaatgg ttgacattta atgatatata aatgctttga      2876
aaagttgctc cactttctat gtgagacttc attccaattc attcaatgca aaatcaacac      2936
acttatcatt ttggaacact aagtaattat tacaacaaca tgttgtaagg gaagtcatca      2996
cttcattaca tgaaaaataa atgagttatg agttggtctg ggtatcacct caaaattcct      3056
caaaattggg ggggggggg gggttaagga atgagttttt caataaatct ggtcactcaa      3116
ctttgcacat tatgctgacc agttgttcct tgcttcatta catatatttc cttgtaggaa      3176
catcaataga tggaagactt tttagtattt ctcttaagta atcaaactaa ctcagtatta      3236
tcctcctatg taacttttt cttttgcag g tat ccg cct ttc att gca caa aat      3290
                                  Tyr Pro Pro Phe Ile Ala Gln Asn
                                              240                 245 aat cgc caa aaa caa caa atg ata atc aat gtaagcaaca tctcgcgttg         3340
Asn Arg Gln Lys Gln Gln Met Ile Ile Asn
            250                 255 attaagtgtg tgtgtcttct taggtagaat gagtaatgca ggcagagtca aaattagcaa      3400
tgtaacaaga agtgatatat gttcaaatat attatccaag ttagttcctg ggttttttcc      3460
```

```
tttattttag attaatcata gtaacatatc acttttatca caaaaattat atagcacgcg      3520
cacacacata cactatattt agatagatat atagacacac catttgcatt ctgtaaaaaa      3580
attgcttacc aaatgaaaca ttttccaaca g ggg aat ttc agt ttc tat gag         3632
                                   Gly Asn Phe Ser Phe Tyr Glu
                                                   260 aag att tgg aag ggc att acc caa tca gcg aag caa ttg att tca agt        3680
Lys Ile Trp Lys Gly Ile Thr Gln Ser Ala Lys Gln Leu Ile Ser Ser
    265                 270                 275 ctt ttg act gtt gat cca agt aag agg cct agt gct caa gag                3722
Leu Leu Thr Val Asp Pro Ser Lys Arg Pro Ser Ala Gln Glu
280             285                 290 gtatatcaat tgtatattct tactaacttc actaatgtga actaggcagc atatctcatt      3782
ctttactaat aacatggaat gaagtgcatc tcctatgata agagcccttt atagcagaaa      3842
attgccataa aatccaatta catgcattca tttttttta taaggacatc tgagggaaaa       3902
aaagtacttt ttctaataat attttgctga tcagaaagca tgactaataa tcacttagca     3962
attccacaaa gtagcaatgc ctttgcatct caaatacagt atgcacattt cttcaacatt     4022
ttgcatcata ttattttcag tttcaaggtg ttttattgac ataattaagc acaacaataa     4082
ccccagacac aattctgttg tacttggaac ag ctc ttg agt cat cca tgg gtc       4135
                                   Leu Leu Ser His Pro Trp Val
                                                   295         300 aga ggt gac aaa gcc aaa gat gag caa atg gac cct gag att gtc tca        4183
Arg Gly Asp Lys Ala Lys Asp Glu Gln Met Asp Pro Glu Ile Val Ser
            305                 310                 315 agg ctg cag agc ttt aat gca aga cgc aaa ctc cgc gca gct gca att        4231
Arg Leu Gln Ser Phe Asn Ala Arg Arg Lys Leu Arg Ala Ala Ala Ile
        320                 325                 330 gct agt gtt tgg agc agc aca atc ttc ctg aga acc aaa aag ctg aga        4279
Ala Ser Val Trp Ser Ser Thr Ile Phe Leu Arg Thr Lys Lys Leu Arg
    335                 340                 345 tcc ttg gta gga act tat gat ctc aaa gaa gag gaa att gaa agt ctc        4327
Ser Leu Val Gly Thr Tyr Asp Leu Lys Glu Glu Glu Ile Glu Ser Leu
350                 355                 360 agg ata cac ttt aag aag at gtaagtactc acaagtctcc aaattaatca            4377
Arg Ile His Phe Lys Lys Ile
365                 370 tagatagtta aattagtccc taaaaattta caatcggtta tcttagtcag tgaatcataa      4437
aaatttacac ttgaagtcct tcaattgtac tttgtagtca tattagtctt tccatcaagt     4497
acttcaggac taatttaacc aagaagacac atatgtagag actacttcga tggacaaaat     4557
gtcaatgtag acatctaaaa taagtttcat tattcaaaga ctaacatcat tgagcttgtg     4617
tttattgagt tgagactgtg ttgacaattt agtacaaata tttctgtgca gcacactagc     4677
atttgacaat tttgactaat tcctgtggtt gctaacag a tgt gga aat gga gac       4731
                                            Cys Gly Asn Gly Asp
                                                            375 aat gca act ctg tct gag ttt gtg gag gtg ctg aaa gca atg aag atg        4779
Asn Ala Thr Leu Ser Glu Phe Val Glu Val Leu Lys Ala Met Lys Met
            380                 385                 390 ccc tca ttg atc cct cta gca ccg cgt ata ttt gac ttg ttt gac aac        4827
Pro Ser Leu Ile Pro Leu Ala Pro Arg Ile Phe Asp Leu Phe Asp Asn
        395                 400                 405 aac cgt gat gga aca att gac atg aga gag ata cta tgt ggg ttt tct        4875
Asn Arg Asp Gly Thr Ile Asp Met Arg Glu Ile Leu Cys Gly Phe Ser
    410                 415                 420 agc ctc aag aac tcc aaa gga gat gat gct ctc cgt ttg tgc ttc cag        4923
Ser Leu Lys Asn Ser Lys Gly Asp Asp Ala Leu Arg Leu Cys Phe Gln
```

```
425              430              435              440
gtgagtcttt ttaagttccg gtcttggtag agcttatttt ctactataat aagtacttaa    4983
gcagggtttt ggttaagttt ataaaaatag ctcatgacat atataaactc ttttgagctt    5043
aattaacttg tatgaataac catttatact tacatctaag ctcttttgag ctaatttcaa    5103
taagtttctc aaattagatt atgagaatat cattagtgtt tgctgacata attgcttagt    5163 taacctatt actcaaacat atccatgaac acatgcacat agacaagaat gcacacatat     5223
agcagtgact cgtgagagct tcaatagtta catccaagaa tatcaattta tgaagcaaaa    5283
aagaaatatc atatatgaga gaagatagta gtattataag taattacata tttactaaca   5343
caaacttttg tgaaaaagat gtggttgtta aatgacaaac aaaaagtttg taattgtaat    5403
tacaattatg ttatatgaat gaatgaatgt tacaattttc accaccctct aagtttcaac    5463
aactctggaa aaagactaca acaaacacaa gacaagaaa agaaacaacc caaaagcatt      5523
tgatacagta caaagtaaaa gtgttcagca tgatcagcta atttttcctca ctgattttct    5583
```
tggccaacag atg tat gac aca gat aga tca ggg tgc atc acc aag gaa      5632
         Met Tyr Asp Thr Asp Arg Ser Gly Cys Ile Thr Lys Glu
                           445                   450 gaa gta gca tcc atg ctc tgt gtaattaatg caccttcctt tcaattaact          5683
Glu Val Ala Ser Met Leu Cys
455                    460 atagccttat cttgtgactt tcttctttct aacacaaatc aattcactga acag gct       5740
                                                                           Ala ttg cca gag gaa tgt ctt cca gct gat atc act gaa cct ggg aaa ttg      5788
Leu Pro Glu Glu Cys Leu Pro Ala Asp Ile Thr Glu Pro Gly Lys Leu
         465                  470                  475 gat gag ata ttt gac tta atg gat gcc aac agt gat gga aaa gtt aca      5836
Asp Glu Ile Phe Asp Leu Met Asp Ala Asn Ser Asp Gly Lys Val Thr
       480                  485                  490 ttt gaa gaa ttc aaa gct gct atg cag aga gat agc tct ctc caa gac      5884
Phe Glu Glu Phe Lys Ala Ala Met Gln Arg Asp Ser Ser Leu Gln Asp
495                  500                  505 atg ctc ctc tct tct ctt cgt cca tca tag tttttttttt tttccattca        5934
Met Leu Leu Ser Ser Leu Arg Pro Ser
510                    515 tggtgttatg gtctttcaaa ctttgatatt gactacacct tttacgtttc ttttaatctc    5994
ttttggggct atccttctct tgaggtatt catactacat ggaaaaaggg tggtaaagag     6054
ggtgaaattg tgtcatctaa cttttgctat gacaactagg aacttttgca ttctcatgta    6114
atactacaac tagcttaaga gagcggctca atgaatgtca aggcttaaaa tgaaatttaa    6174
gaggagattt tttaaattaa ttaaatagtt ttattgaaat tattgtaatt ctatttttta    6234
tattaatctt ttgtagtttg agttaagtta ttaatcattt aacatttctt ttttgaatta    6294
atcatagaat aaattgtcaa tcaatttaat cacagttgat agttgaggca ctgttgatat    6354
tagataaggc aaataatagt aaagttaatt cattgaatat tgagagggga aaacaaagaa    6414
cggtttataa tcttgatgat aataattttg aaagaatgga ggtagaagat ttcaattgca    6474
atatatgaaa a                                                          6485

<210> SEQ ID NO 17
<211> LENGTH: 1557
<212> TYPE: DNA
<213> ORGANISM: Lotus japonicus
<220> FEATURE:
<221> NAME/KEY: CDS
<222> LOCATION: (1)..(1557)

<400> SEQUENCE: 17

```
atg gga tat gat caa acc aga aag ctc tct gat gag tat gag att tca      48
Met Gly Tyr Asp Gln Thr Arg Lys Leu Ser Asp Glu Tyr Glu Ile Ser
1               5                   10                  15 gag att cta gga aga ggt gga ttc tct gtt gtc aga aaa gga acc aaa      96
Glu Ile Leu Gly Arg Gly Gly Phe Ser Val Val Arg Lys Gly Thr Lys
            20                  25                  30 aaa tca ggc aat gag aaa acc caa gta gcc atc aaa aca ctc aga agg     144
Lys Ser Gly Asn Glu Lys Thr Gln Val Ala Ile Lys Thr Leu Arg Arg
        35                  40                  45 tta ggt agt tct ccc tct ggg aca ggt ggt gga cag aag agc aca gca     192
Leu Gly Ser Ser Pro Ser Gly Thr Gly Gly Gly Gln Lys Ser Thr Ala
50                  55                  60 act gtg atg ggg ttc cct tct ttg aga cag gtt tca gtc tca gat gct     240
Thr Val Met Gly Phe Pro Ser Leu Arg Gln Val Ser Val Ser Asp Ala
65                  70                  75                  80 ttg ctc acc aat gag att ctt gtg atg agg agg ata gtg gaa aac gtt     288
Leu Leu Thr Asn Glu Ile Leu Val Met Arg Arg Ile Val Glu Asn Val
                85                  90                  95 tcg cca cat cca aac gtg att gat ctc tat gat gtg tgt gag gac tca     336
Ser Pro His Pro Asn Val Ile Asp Leu Tyr Asp Val Cys Glu Asp Ser
            100                 105                 110 aat ggg gtg cat ctt gtg ctg gag ctt tgt tct ggt ggg gag ctg ttt     384
Asn Gly Val His Leu Val Leu Glu Leu Cys Ser Gly Gly Glu Leu Phe
        115                 120                 125 gat agg att gtt gca cag gat aag tat gct gag acg gaa gct gcc gcg     432
Asp Arg Ile Val Ala Gln Asp Lys Tyr Ala Glu Thr Glu Ala Ala Ala
130                 135                 140 gtg gtt cgc cag att gcg gcg ggg cta gag gcg gtt cac aag gct gac     480
Val Val Arg Gln Ile Ala Ala Gly Leu Glu Ala Val His Lys Ala Asp
145                 150                 155                 160 att gtt cac agg gat ttg aag cct gag aat tgc ctt ttc ttg gat tcc     528
Ile Val His Arg Asp Leu Lys Pro Glu Asn Cys Leu Phe Leu Asp Ser
                165                 170                 175 agg aag gac tct cct ctc aag atc atg gac ttt ggg ttg agc tct gtt     576
Arg Lys Asp Ser Pro Leu Lys Ile Met Asp Phe Gly Leu Ser Ser Val
            180                 185                 190 gag gag ttc act gac cct gtt gtt ggg ttg ttt gga tcc att gat tat     624
Glu Glu Phe Thr Asp Pro Val Val Gly Leu Phe Gly Ser Ile Asp Tyr
        195                 200                 205 gtt tca cca gag gct ctt tct caa ggg aag atc act gcc aag agt gac     672
Val Ser Pro Glu Ala Leu Ser Gln Gly Lys Ile Thr Ala Lys Ser Asp
210                 215                 220 atg tgg tct ctg gga gtg att cta tat atc ttg ctc tct ggg tat ccg     720
Met Trp Ser Leu Gly Val Ile Leu Tyr Ile Leu Leu Ser Gly Tyr Pro
225                 230                 235                 240 cct ttc att gca caa aat aat cgc caa aaa caa caa atg ata atc aat     768
Pro Phe Ile Ala Gln Asn Asn Arg Gln Lys Gln Gln Met Ile Ile Asn
                245                 250                 255 ggg aat ttc agt ttc tat gag aag att tgg aag ggc att acc caa tca     816
Gly Asn Phe Ser Phe Tyr Glu Lys Ile Trp Lys Gly Ile Thr Gln Ser
            260                 265                 270 gcg aag caa ttg att tca agt ctt ttg act gtt gat cca agt aag agg     864
Ala Lys Gln Leu Ile Ser Ser Leu Leu Thr Val Asp Pro Ser Lys Arg
        275                 280                 285 cct agt gct caa gag ctc ttg agt cat cca tgg gtc aga ggt gac aaa     912
Pro Ser Ala Gln Glu Leu Leu Ser His Pro Trp Val Arg Gly Asp Lys
290                 295                 300 gcc aaa gat gag caa atg gac cct gag att gtc tca agg ctg cag agc     960
Ala Lys Asp Glu Gln Met Asp Pro Glu Ile Val Ser Arg Leu Gln Ser
```

```
                    305                 310                 315                 320
ttt aat gca aga cgc aaa ctc cgc gca gct gca att gct agt gtt tgg         1008
Phe Asn Ala Arg Arg Lys Leu Arg Ala Ala Ala Ile Ala Ser Val Trp
                325                 330                 335 agc agc aca atc ttc ctg aga acc aaa aag ctg aga tcc ttg gta gga         1056
Ser Ser Thr Ile Phe Leu Arg Thr Lys Lys Leu Arg Ser Leu Val Gly
        340                 345                 350 act tat gat ctc aaa gaa gag gaa att gaa agt ctc agg ata cac ttt         1104
Thr Tyr Asp Leu Lys Glu Glu Glu Ile Glu Ser Leu Arg Ile His Phe
    355                 360                 365 aag aag ata tgt gga aat gga gac aat gca act ctg tct gag ttt gtg         1152
Lys Lys Ile Cys Gly Asn Gly Asp Asn Ala Thr Leu Ser Glu Phe Val
370                 375                 380 gag gtg ctg aaa gca atg aag atg ccc tca ttg atc cct cta gca ccg         1200
Glu Val Leu Lys Ala Met Lys Met Pro Ser Leu Ile Pro Leu Ala Pro
385                 390                 395                 400 cgt ata ttt gac ttg ttt gac aac aac cgt gat gga aca att gac atg         1248
Arg Ile Phe Asp Leu Phe Asp Asn Asn Arg Asp Gly Thr Ile Asp Met
            405                 410                 415 aga gag ata cta tgt ggg ttt tct agc ctc aag aac tcc aaa gga gat         1296
Arg Glu Ile Leu Cys Gly Phe Ser Ser Leu Lys Asn Ser Lys Gly Asp
        420                 425                 430 gat gct ctc cgt ttg tgc ttc cag atg tat gac aca gat aga tca ggg         1344
Asp Ala Leu Arg Leu Cys Phe Gln Met Tyr Asp Thr Asp Arg Ser Gly
    435                 440                 445 tgc atc acc aag gaa gaa gta gca tcc atg ctc tgt gct ttg cca gag         1392
Cys Ile Thr Lys Glu Glu Val Ala Ser Met Leu Cys Ala Leu Pro Glu
450                 455                 460 gaa tgt ctt cca gct gat atc act gaa cct ggg aaa ttg gat gag ata         1440
Glu Cys Leu Pro Ala Asp Ile Thr Glu Pro Gly Lys Leu Asp Glu Ile
465                 470                 475                 480 ttt gac tta atg gat gcc aac agt gat gga aaa gtt aca ttt gaa gaa         1488
Phe Asp Leu Met Asp Ala Asn Ser Asp Gly Lys Val Thr Phe Glu Glu
            485                 490                 495 ttc aaa gct gct atg cag aga gat agc tct ctc caa gac atg ctc ctc         1536
Phe Lys Ala Ala Met Gln Arg Asp Ser Ser Leu Gln Asp Met Leu Leu
        500                 505                 510 tct tct ctt cgt cca tca tag                                             1557
Ser Ser Leu Arg Pro Ser
    515

<210> SEQ ID NO 18
<211> LENGTH: 518
<212> TYPE: PRT
<213> ORGANISM: Lotus japonicus

<400> SEQUENCE: 18

Met Gly Tyr Asp Gln Thr Arg Lys Leu Ser Asp Glu Tyr Glu Ile Ser
1               5                   10                  15

Glu Ile Leu Gly Arg Gly Gly Phe Ser Val Val Arg Lys Gly Thr Lys
            20                  25                  30

Lys Ser Gly Asn Glu Lys Thr Gln Val Ala Ile Lys Thr Leu Arg Arg
        35                  40                  45

Leu Gly Ser Ser Pro Ser Gly Thr Gly Gly Gln Lys Ser Thr Ala
    50                  55                  60

Thr Val Met Gly Phe Pro Ser Leu Arg Gln Val Ser Val Ser Asp Ala
65                  70                  75                  80

Leu Leu Thr Asn Glu Ile Leu Val Met Arg Arg Ile Val Glu Asn Val
            85                  90                  95
```

```
Ser Pro His Pro Asn Val Ile Asp Leu Tyr Asp Val Cys Glu Asp Ser
            100                 105                 110

Asn Gly Val His Leu Val Leu Glu Leu Cys Ser Gly Glu Leu Phe
            115                 120                 125

Asp Arg Ile Val Ala Gln Asp Lys Tyr Ala Glu Thr Glu Ala Ala Ala
130                 135                 140

Val Val Arg Gln Ile Ala Ala Gly Leu Glu Ala Val His Lys Ala Asp
145                 150                 155                 160

Ile Val His Arg Asp Leu Lys Pro Glu Asn Cys Leu Phe Leu Asp Ser
                165                 170                 175

Arg Lys Asp Ser Pro Leu Lys Ile Met Asp Phe Gly Leu Ser Ser Val
            180                 185                 190

Glu Glu Phe Thr Asp Pro Val Val Gly Leu Phe Gly Ser Ile Asp Tyr
            195                 200                 205

Val Ser Pro Glu Ala Leu Ser Gln Gly Lys Ile Thr Ala Lys Ser Asp
            210                 215                 220

Met Trp Ser Leu Gly Val Ile Leu Tyr Ile Leu Leu Ser Gly Tyr Pro
225                 230                 235                 240

Pro Phe Ile Ala Gln Asn Asn Arg Gln Lys Gln Gln Met Ile Ile Asn
                245                 250                 255

Gly Asn Phe Ser Phe Tyr Glu Lys Ile Trp Lys Gly Ile Thr Gln Ser
            260                 265                 270

Ala Lys Gln Leu Ile Ser Ser Leu Leu Thr Val Asp Pro Ser Lys Arg
            275                 280                 285

Pro Ser Ala Gln Glu Leu Leu Ser His Pro Trp Val Arg Gly Asp Lys
290                 295                 300

Ala Lys Asp Glu Gln Met Asp Pro Glu Ile Val Ser Arg Leu Gln Ser
305                 310                 315                 320

Phe Asn Ala Arg Arg Lys Leu Arg Ala Ala Ile Ala Ser Val Trp
                325                 330                 335

Ser Ser Thr Ile Phe Leu Arg Thr Lys Lys Leu Arg Ser Leu Val Gly
            340                 345                 350

Thr Tyr Asp Leu Lys Glu Glu Ile Glu Ser Leu Arg Ile His Phe
            355                 360                 365

Lys Lys Ile Cys Gly Asn Gly Asp Asn Ala Thr Leu Ser Glu Phe Val
370                 375                 380

Glu Val Leu Lys Ala Met Lys Met Pro Ser Leu Ile Pro Leu Ala Pro
385                 390                 395                 400

Arg Ile Phe Asp Leu Phe Asp Asn Asn Arg Asp Gly Thr Ile Asp Met
                405                 410                 415

Arg Glu Ile Leu Cys Gly Phe Ser Ser Leu Lys Asn Ser Lys Gly Asp
            420                 425                 430

Asp Ala Leu Arg Leu Cys Phe Gln Met Tyr Asp Thr Asp Arg Ser Gly
            435                 440                 445

Cys Ile Thr Lys Glu Glu Val Ala Ser Met Leu Cys Ala Leu Pro Glu
            450                 455                 460

Glu Cys Leu Pro Ala Asp Ile Thr Glu Pro Gly Lys Leu Asp Glu Ile
465                 470                 475                 480

Phe Asp Leu Met Asp Ala Asn Ser Asp Gly Lys Val Thr Phe Glu Glu
                485                 490                 495

Phe Lys Ala Ala Met Gln Arg Asp Ser Ser Leu Gln Asp Met Leu Leu
            500                 505                 510

Ser Ser Leu Arg Pro Ser
            515
```

```
<210> SEQ ID NO 19
<211> LENGTH: 6485
<212> TYPE: DNA
<213> ORGANISM: Lotus japonicus
<220> FEATURE:
<221> NAME/KEY: 5'UTR
<222> LOCATION: (1)..(323)
<220> FEATURE:
<221> NAME/KEY: exon
<222> LOCATION: (324)..(1036)
<220> FEATURE:
<221> NAME/KEY: Intron
<222> LOCATION: (1037)..(3265)
<220> FEATURE:
<221> NAME/KEY: exon
<222> LOCATION: (3266)..(3320)
<220> FEATURE:
<221> NAME/KEY: Intron
<222> LOCATION: (3321)..(3611)
<220> FEATURE:
<221> NAME/KEY: exon
<222> LOCATION: (3612)..(3722)
<220> FEATURE:
<221> NAME/KEY: Intron
<222> LOCATION: (3723)..(4114)
<220> FEATURE:
<221> NAME/KEY: exon
<222> LOCATION: (4115)..(4347)
<220> FEATURE:
<221> NAME/KEY: Intron
<222> LOCATION: (4348)..(4715)
<220> FEATURE:
<221> NAME/KEY: exon
<222> LOCATION: (4716)..(4923)
<220> FEATURE:
<221> NAME/KEY: Intron
<222> LOCATION: (4924)..(5593)
<220> FEATURE:
<221> NAME/KEY: exon
<222> LOCATION: (5594)..(5653)
<220> FEATURE:
<221> NAME/KEY: Intron
<222> LOCATION: (5654)..(5737)
<220> FEATURE:
<221> NAME/KEY: exon
<222> LOCATION: (5738)..(5914)
<220> FEATURE:
<221> NAME/KEY: 3'UTR
<222> LOCATION: (5915)..(6485)

<400> SEQUENCE: 19
ttttcaagtc ggctaaatag tgaatagaag aattttagag tacaaaatgg tagcagttga      60
ctctctctct gtcccttcta aaacagcccc taccagccat tgtttattct cttgtaccta     120
tctgaatttg cttcatattt tatgccataa actaatgcag aaactctcac aaaggctaat     180
gtcaacatca accattttca atacgcgttt tgtaggccga tcattgaaac ttgaagtcat     240
gttatattat acatacctct tctcattgat cattgaacat tttctgagtc tgaaaagatt     300
ccaatatttt caaacactct gcc atg gga tat gat caa acc aga aag ctc tct     353
                         Met Gly Tyr Asp Gln Thr Arg Lys Leu Ser
                           1               5                  10 gat gag tat gag att tca gag att cta gga aga ggt gga ttc tct gtt     401
Asp Glu Tyr Glu Ile Ser Glu Ile Leu Gly Arg Gly Gly Phe Ser Val
             15                  20                  25 gtc aga aaa gga acc aaa aaa tca ggc aat gag aaa acc caa gta gcc     449
Val Arg Lys Gly Thr Lys Lys Ser Gly Asn Glu Lys Thr Gln Val Ala
         30                  35                  40 atc aaa aca ctc aga agg tta ggt agt tct ccc tct ggg aca ggt ggt     497
Ile Lys Thr Leu Arg Arg Leu Gly Ser Ser Pro Ser Gly Thr Gly Gly
     45                  50                  55
```

```
gga cag aag agc aca gca act gtg atg ggg ttc cct tct ttg aga cag       545
Gly Gln Lys Ser Thr Ala Thr Val Met Gly Phe Pro Ser Leu Arg Gln
     60                  65                  70 gtt tca gtc tca gat gct ttg ctc acc aat gag att ctt gtg atg agg       593
Val Ser Val Ser Asp Ala Leu Leu Thr Asn Glu Ile Leu Val Met Arg
 75                  80                  85                  90 agg ata gtg gaa aac gtt tcg cca cat cca aac gtg att gat ctc tat       641
Arg Ile Val Glu Asn Val Ser Pro His Pro Asn Val Ile Asp Leu Tyr
                 95                 100                 105 gat gtg tgt gag gac tca aat ggg gtg cat ctt gtg ctg gag ctt tgt       689
Asp Val Cys Glu Asp Ser Asn Gly Val His Leu Val Leu Glu Leu Cys
            110                 115                 120 tct ggt ggg gag ctg ttt gat agg att gtt gca cag gat aag tat gct       737
Ser Gly Gly Glu Leu Phe Asp Arg Ile Val Ala Gln Asp Lys Tyr Ala
        125                 130                 135 gag acg gaa gct gcc gcg gtg gtt cgc cag att gcg gcg ggg cta gag       785
Glu Thr Glu Ala Ala Ala Val Val Arg Gln Ile Ala Ala Gly Leu Glu
    140                 145                 150 gcg gtt cac aag gct gac att gtt cac agg gat ttg aag cct gag aat       833
Ala Val His Lys Ala Asp Ile Val His Arg Asp Leu Lys Pro Glu Asn
155                 160                 165                 170 tgc ctt ttc ttg gat tcc agg aag gac tct cct ctc aag atc atg gac       881
Cys Leu Phe Leu Asp Ser Arg Lys Asp Ser Pro Leu Lys Ile Met Asp
                175                 180                 185 ttt ggg ttg agc tct gtt gag gag ttc act gac cct gtt gtt ggg ttg       929
Phe Gly Leu Ser Ser Val Glu Glu Phe Thr Asp Pro Val Val Gly Leu
            190                 195                 200 ttt gga tcc att gat tat gtt tca cca gag gct ctt tct caa ggg aag       977
Phe Gly Ser Ile Asp Tyr Val Ser Pro Glu Ala Leu Ser Gln Gly Lys
        205                 210                 215 atc act gcc aag agt gac atg tgg tct ctg gga gtg att cta tat atc      1025
Ile Thr Ala Lys Ser Asp Met Trp Ser Leu Gly Val Ile Leu Tyr Ile
    220                 225                 230 ttg ctc tct gg  gtatgttgtc tttcacttgt tgaaattgtt catattgtgt          1076
Leu Leu Ser Gly
235 tggttgctcc ccatccacct tttgcagagc ccatttggat acaagcttat tgatgtttat    1136 tgaagcttat ctactagaaa atgcactaaa taagcttcca caatactctt tggcttgcat    1196 ccaaacggct acttagtgca gtaaatatgg atgccaagaa ggaaatttta gtttctcact    1256 tattaggtgg cattagtctt tgaaacttaa aaaaaaaaac ccactgataa catgctcgaa    1316 aattattcta caattgatta tgaaaaatta attgttagaa tataatataa aagcattaaa    1376 gtgacctttc cccaacagct taagcttttg ggattaagtg gttatttgac atggtatcac    1436 tagggatggc aacgggtagg atcgggcatg gttttacaa ttaccaaacc caaacccaaa     1496 tcccagaacc caaacccaaa cccaaacaca aacccttatg ggcgataaaa tgaaattcat    1556 gcccaaatcc attgggtttc ggatttaccc gaaactcaaa cccaaaccca ttagttaggt    1616 agcaactcaa tccagaactt actttcatat aaaagaaaag tgaaattcat ataagaaaa     1676 aaaaaacaaa tactattcat catcctcatc catcactaaa gtgagacaac aatagtttaa    1736 agtttacttt ctcaaacata caaaagtaca attaatcatc aaacactaag aacaaagttt    1796 ataaatatat atatgtatga gggtttttt gtaattttat gtttcgggta tctttgggtt     1856 cgggtttggg cggggtatgg gcatgaattt aactaatacc aaaatccaaa ctcataaatg    1916 gcttcagtaa cgggcaaaac tcaaacccaa acccaaatcc agtcaactcg gattttgccc    1976 gtcaaatcgg atcgggtacc catgggtttg ggcaaaattt ccatccctag gtatcagagc    2036
```

-continued

```
ctctatgacc gagaggtcta gagttcgatc cttgctcccc tcactttcta attaaaaaag    2096
tggaatttaa ttaagcacat ggtaggtgga cctgtgcatt tatccacgct acaagcccaa    2156
agggctcttg cgtgaggagg cgtgttagaa tataatataa aaccattaaa gtgacccctta   2216
cccaacagct taagctttt  ggataagtgg ttgtttgaca ttaatacttg agagaaactt    2276
atatgaatag cttctgaatg atgttccata attcattttg agaaagaaaa aaagctaatc    2336
caaacatgtg ttagaaaatg aacatgcttg atcgtgatga aataactttc cttaaagtat    2396
ttcaagcact ctctaaattt cgtcttagag tttggatgca agaatacccca ggataatcag   2456
ccttgattcg agtttgcaca agactaatga aaactcgaaa tgaagagaag tgattttctg    2516
gaaacagag  gatatgattg tgtgttatga attctgaaca tggactctat ttataggcaa    2576
aacagaacaa tatataaggt tgcgacccctt catatattgt gtctgttaac aacagtcgca   2636
aaaatcaaat tcaaaagag  caaaaacaaa cggacgttac ggcaaccgcg tagccgtcgt    2696
tgcgtctaca agccgccact agcgcctcta cgcccacgcc tgtgacaccg gcagggggtg    2756
gtgtgagtgg aatatgtgac ataaaagctt gggaccacca aactatgcac atgtggcact   2816
atatcctctt tttgtctctt tgttgaatgg ttgacattta atgatatata aatgctttga    2876
aaagttgctc cactttctat gtgagacttc attccaattc attcaatgca aaatcaacac   2936
acttatcatt ttggaacact aagtaattat tacaacaaca tgttgtaagg gaagtcatca    2996
cttcattaca tgaaaaataa atgagttatg agttggtctg ggtatcacct caaaattcct   3056
caaaattggg gggggggggg gggttaagga atgagttttt caataaatct ggtcactcaa    3116
ctttgcacat tatgctgacc agttgttcct tgcttcatta catatatttc cttgtaggaa    3176
catcaataga tggaagactt tttagtattt ctcttaagta atcaaactaa ctcagtatta    3236
tcctcctatg taacttttt  cttttgcag g tat ccg cct ttc att gca caa aat    3290
                                 Tyr Pro Pro Phe Ile Ala Gln Asn
                                              240              245
aat cgc caa aaa caa caa atg ata atc aat gtaagcaaca tctcgcgttg        3340
Asn Arg Gln Lys Gln Gln Met Ile Ile Asn
        250                 255
attaagtgtg tgtgtcttct taggtagaat gagtaatgca ggcagagtca aaattagcaa   3400
tgtaacaaga agtgatatat gttcaaatat attatccaag ttagttcctg ggttttttcc   3460
tttattttag attaatcata gtaacatatc acttttatca caaaaattat atagcacgcg    3520
cacacacata cactatattt agatagatat atagacacac catttgcatt ctgtaaaaaa   3580
attgcttacc aaatgaaaca ttttccaaca g ggg aat ttc agt ttc tat gag       3632
                                   Gly Asn Phe Ser Phe Tyr Glu
                                                        260
aag act tgg aag ggc att acc caa tca gcg aag caa ttg att tca agt     3680
Lys Thr Trp Lys Gly Ile Thr Gln Ser Ala Lys Gln Leu Ile Ser Ser
    265                 270                 275
ctt ttg act gtt gat cca agt aag agg cct agt gct caa gag              3722
Leu Leu Thr Val Asp Pro Ser Lys Arg Pro Ser Ala Gln Glu
280                 285                 290
gtatatcaat tgtatattct tactaacttc actaatgtga actaggcagc atatctcatt    3782
ctttactaat aacatggaat gaagtgcatc tcctatgata agagcccttt atagcagaaa    3842
attgccataa aatccaatta catgcattca tttttttta  taaggacatc tgagggaaaa    3902
aaagtacttt ttctaataat attttgctga tcagaaagca tgactaataa tcacttagca    3962
attccacaaa gtagcaatgc ctttgcatct caaatacagt atgcacattt cttcaacatt    4022
ttgcatcata ttattttcag tttcaaggtg ttttattgac ataattaagc acaacaataa   4082
```

-continued

| | |
|---|---|
| ccccagacac aattctgttg tacttggaac ag ctc ttg agt cat cca tgg gtc<br>                                                             Leu Leu Ser His Pro Trp Val<br>                                                                    295                    300 | 4135 |
| aga ggt gac aaa gcc aaa gat gag caa atg gac cct gag att gtc tca<br>Arg Gly Asp Lys Ala Lys Asp Glu Gln Met Asp Pro Glu Ile Val Ser<br>                   305                         310                         315 | 4183 |
| agg ctg cag agc ttt aat gca aga cgc aaa ctc cgc gca gct gca att<br>Arg Leu Gln Ser Phe Asn Ala Arg Arg Lys Leu Arg Ala Ala Ala Ile<br>        320                         325                        330 | 4231 |
| gct agt gtt tgg agc agc aca atc ttc ctg aga acc aaa aag ctg aga<br>Ala Ser Val Trp Ser Ser Thr Ile Phe Leu Arg Thr Lys Lys Leu Arg<br>       335                       340                       345 | 4279 |
| tcc ttg gta gga act tat gat ctc aaa gaa gag gaa att gaa agt ctc<br>Ser Leu Val Gly Thr Tyr Asp Leu Lys Glu Glu Glu Ile Glu Ser Leu<br> 350                      355                       360 | 4327 |
| agg ata cac ttt aag aag at  gtaagtactc acaagtctcc aaattaatca<br>Arg Ile His Phe Lys Lys Ile<br>365                  370 | 4377 |
| tagatagtta aattagtccc taaaaattta caatcggtta tcttagtcag tgaatcataa | 4437 |
| aaatttacac ttgaagtcct tcaattgtac tttgtagtca tattagtctt tccatcaagt | 4497 |
| acttcaggac taatttaacc aagaagacac atatgtagag actacttcga tggacaaaat | 4557 |
| gtcaatgtag acatctaaaa taagtttcat tattcaaaga ctaacatcat tgagcttgtg | 4617 |
| tttattgagt tgagactgtg ttgacaattt agtacaaata tttctgtgca gcacactagc | 4677 |
| atttgacaat tttgactaat tcctgtggtt gctaacag a tgt gga aat gga gac<br>                                                               Cys Gly Asn Gly Asp<br>                                                                            375 | 4731 |
| aat gca act ctg tct gag ttt gtg gag gtg ctg aaa gca atg aag atg<br>Asn Ala Thr Leu Ser Glu Phe Val Glu Val Leu Lys Ala Met Lys Met<br>       380                       385                       390 | 4779 |
| ccc tca ttg atc cct cta gca ccg cgt ata ttt gac ttg ttt gac aac<br>Pro Ser Leu Ile Pro Leu Ala Pro Arg Ile Phe Asp Leu Phe Asp Asn<br>        395                       400                       405 | 4827 |
| aac cgt gat gga aca att gac atg aga gag ata cta tgt ggg ttt tct<br>Asn Arg Asp Gly Thr Ile Asp Met Arg Glu Ile Leu Cys Gly Phe Ser<br>    410                       415                       420 | 4875 |
| agc ctc aag aac tcc aaa gga gat gat gct ctc cgt ttg tgc ttc cag<br>Ser Leu Lys Asn Ser Lys Gly Asp Asp Ala Leu Arg Leu Cys Phe Gln<br>425                  430                       435                       440 | 4923 |
| gtgagtcttt ttaagttccg gtcttggtag agcttatttt ctactataat aagtacttaa | 4983 |
| gcaggggttt ggttaagttt ataaaaatag ctcatgacat atataaactc ttttgagctt | 5043 |
| aattaacttg tatgaataac catttatact tacatctaag ctcttttgag ctaatttcaa | 5103 |
| taagtttctc aaattagatt atgagaatat cattagtgtt tgctgacata attgcttagt | 5163 |
| taacctattt actcaaacat atccatgaac acatgcacat agacaagaat gcacacatat | 5223 |
| agcagtgact cgtgagagct tcaatagtta catccaagaa tatcaattta tgaagcaaaa | 5283 |
| aagaaatatc atatatgaga aagatagta gtattataag taattacata tttactaaca | 5343 |
| caaactttg tgaaaagat gtggttgtta aatgacaaac aaaagtttg taattgtaat | 5403 |
| tacaattatg ttatatgaat gaatgaatgt tacaattttc accaccctct aagtttcaac | 5463 |
| aactctggaa aaagactaca acaaacacaa gacaagaaa agaacaacc caaaagcatt | 5523 |
| tgatacagta caaagtaaaa gtgttcagca tgatcagcta atttcctca ctgatttct | 5583 |
| tggccaacag atg tat gac aca gat aga tca ggg tgc atc acc aag gaa<br>              Met Tyr Asp Thr Asp Arg Ser Gly Cys Ile Thr Lys Glu<br>                                       445                         450 | 5632 |

```
gaa gta gca tcc atg ctc tgt gtaattaatg caccttcctt tcaattaact    5683
Glu Val Ala Ser Met Leu Cys
    455             460 atagccttat cttgtgactt tcttctttct aacacaaatc aattcactga acag gct  5740
                                                         Ala ttg cca gag gaa tgt ctt cca gct gat atc act gaa cct ggg aaa ttg 5788
Leu Pro Glu Glu Cys Leu Pro Ala Asp Ile Thr Glu Pro Gly Lys Leu
            465                 470                 475 gat gag ata ttt gac tta atg gat gcc aac agt gat gga aaa gtt aca 5836
Asp Glu Ile Phe Asp Leu Met Asp Ala Asn Ser Asp Gly Lys Val Thr
        480                 485                 490 ttt gaa gaa ttc aaa gct gct atg cag aga gat agc tct ctc caa gac 5884
Phe Glu Glu Phe Lys Ala Ala Met Gln Arg Asp Ser Ser Leu Gln Asp
    495                 500                 505 atg ctc ctc tct tct ctt cgt cca tca tag ttttttttt tttccattca    5934
Met Leu Leu Ser Ser Leu Arg Pro Ser
510                 515 tggtgttatg gtctttcaaa ctttgatatt gactacacct tttacgtttc ttttaatctc 5994 ttttggggct atccttctct tgaggtatt catactacat ggaaaaaggg tggtaaagag 6054 ggtgaaattg tgtcatctaa cttttgctat gacaactagg aacttttgca ttctcatgta 6114 atactacaac tagcttaaga gagcggctca atgaatgtca aggcttaaaa tgaaatttaa 6174 gaggagattt tttaaattaa ttaaatagtt ttattgaaat tattgtaatt ctattttta  6234 tattaatctt ttgtagtttg agttaagtta ttaatcattt aacatttctt ttttgaatta 6294 atcatagaat aaattgtcaa tcaatttaat cacagttgat agttgaggca ctgttgatat 6354 tagataaggc aaataatagt aaagttaatt cattgaatat tgagagggga aaacaaagaa 6414 cggtttataa tcttgatgat aataattttg aaagaatgga ggtagaagat ttcaattgca 6474 atatatgaaa a                                                     6485

<210> SEQ ID NO 20
<211> LENGTH: 1557
<212> TYPE: DNA
<213> ORGANISM: Lotus japonicus
<220> FEATURE:
<221> NAME/KEY: CDS
<222> LOCATION: (1)..(1557)

<400> SEQUENCE: 20 atg gga tat gat caa acc aga aag ctc tct gat gag tat gag att tca   48
Met Gly Tyr Asp Gln Thr Arg Lys Leu Ser Asp Glu Tyr Glu Ile Ser
1               5                   10                  15 gag att cta gga aga ggt gga ttc tct gtt gtc aga aaa gga acc aaa   96
Glu Ile Leu Gly Arg Gly Gly Phe Ser Val Val Arg Lys Gly Thr Lys
            20                  25                  30 aaa tca ggc aat gag aaa acc caa gta gcc atc aaa aca ctc aga agg  144
Lys Ser Gly Asn Glu Lys Thr Gln Val Ala Ile Lys Thr Leu Arg Arg
        35                  40                  45 tta ggt agt tct ccc tct ggg aca ggt ggt gga cag aag agc aca gca  192
Leu Gly Ser Ser Pro Ser Gly Thr Gly Gly Gly Gln Lys Ser Thr Ala
    50                  55                  60 act gtg atg ggg ttc cct tct ttg aga cag gtt tca gtc tca gat gct  240
Thr Val Met Gly Phe Pro Ser Leu Arg Gln Val Ser Val Ser Asp Ala
65                  70                  75                  80 ttg ctc acc aat gag att ctt gtg atg agg agg ata gtg gaa aac gtt  288
Leu Leu Thr Asn Glu Ile Leu Val Met Arg Arg Ile Val Glu Asn Val
                85                  90                  95 tcg cca cat cca aac gtg att gat ctc tat gat gtg tgt gag gac tca  336
Ser Pro His Pro Asn Val Ile Asp Leu Tyr Asp Val Cys Glu Asp Ser
```

```
                100                  105                  110
aat ggg gtg cat ctt gtg ctg gag ctt tgt tct ggt ggg gag ctg ttt        384
Asn Gly Val His Leu Val Leu Glu Leu Cys Ser Gly Gly Glu Leu Phe
        115                  120                  125 gat agg att gtt gca cag gat aag tat gct gag acg gaa gct gcc gcg        432
Asp Arg Ile Val Ala Gln Asp Lys Tyr Ala Glu Thr Glu Ala Ala Ala
130                 135                  140 gtg gtt cgc cag att gcg gcg ggg cta gag gcg gtt cac aag gct gac        480
Val Val Arg Gln Ile Ala Ala Gly Leu Glu Ala Val His Lys Ala Asp
145                 150                  155                  160 att gtt cac agg gat ttg aag cct gag aat tgc ctt ttc ttg gat tcc        528
Ile Val His Arg Asp Leu Lys Pro Glu Asn Cys Leu Phe Leu Asp Ser
            165                  170                  175 agg aag gac tct cct ctc aag atc atg gac ttt ggg ttg agc tct gtt        576
Arg Lys Asp Ser Pro Leu Lys Ile Met Asp Phe Gly Leu Ser Ser Val
            180                  185                  190 gag gag ttc act gac cct gtt gtt ggg ttg ttt gga tcc att gat tat        624
Glu Glu Phe Thr Asp Pro Val Val Gly Leu Phe Gly Ser Ile Asp Tyr
            195                  200                  205 gtt tca cca gag gct ctt tct caa ggg aag atc act gcc aag agt gac        672
Val Ser Pro Glu Ala Leu Ser Gln Gly Lys Ile Thr Ala Lys Ser Asp
210                 215                  220 atg tgg tct ctg gga gtg att cta tat atc ttg ctc tct ggg tat ccg        720
Met Trp Ser Leu Gly Val Ile Leu Tyr Ile Leu Leu Ser Gly Tyr Pro
225                 230                  235                  240 cct ttc att gca caa aat aat cgc caa aaa caa caa atg ata atc aat        768
Pro Phe Ile Ala Gln Asn Asn Arg Gln Lys Gln Gln Met Ile Ile Asn
                245                  250                  255 ggg aat ttc agt ttc tat gag aag act tgg aag ggc att acc caa tca        816
Gly Asn Phe Ser Phe Tyr Glu Lys Thr Trp Lys Gly Ile Thr Gln Ser
            260                  265                  270 gcg aag caa ttg att tca agt ctt ttg act gtt gat cca agt aag agg        864
Ala Lys Gln Leu Ile Ser Ser Leu Leu Thr Val Asp Pro Ser Lys Arg
        275                  280                  285 cct agt gct caa gag ctc ttg agt cat cca tgg gtc aga ggt gac aaa        912
Pro Ser Ala Gln Glu Leu Leu Ser His Pro Trp Val Arg Gly Asp Lys
290                 295                  300 gcc aaa gat gag caa atg gac cct gag att gtc tca agg ctg cag agc        960
Ala Lys Asp Glu Gln Met Asp Pro Glu Ile Val Ser Arg Leu Gln Ser
305                 310                  315                  320 ttt aat gca aga cgc aaa ctc cgc gca gct gca att gct agt gtt tgg       1008
Phe Asn Ala Arg Arg Lys Leu Arg Ala Ala Ala Ile Ala Ser Val Trp
                325                  330                  335 agc agc aca atc ttc ctg aga acc aaa aag ctg aga tcc ttg gta gga       1056
Ser Ser Thr Ile Phe Leu Arg Thr Lys Lys Leu Arg Ser Leu Val Gly
            340                  345                  350 act tat gat ctc aaa gaa gag gaa att gaa agt ctc agg ata cac ttt       1104
Thr Tyr Asp Leu Lys Glu Glu Glu Ile Glu Ser Leu Arg Ile His Phe
            355                  360                  365 aag aag ata tgt gga aat gga gac aat gca act ctg tct gag ttt gtg       1152
Lys Lys Ile Cys Gly Asn Gly Asp Asn Ala Thr Leu Ser Glu Phe Val
        370                  375                  380 gag gtg ctg aaa gca atg aag atg ccc tca ttg atc cct cta gca ccg       1200
Glu Val Leu Lys Ala Met Lys Met Pro Ser Leu Ile Pro Leu Ala Pro
385                 390                  395                  400 cgt ata ttt gac ttg ttt gac aac aac cgt gat gga aca att gac atg       1248
Arg Ile Phe Asp Leu Phe Asp Asn Asn Arg Asp Gly Thr Ile Asp Met
                405                  410                  415 aga gag ata cta tgt ggg ttt tct agc ctc aag aac tcc aaa gga gat       1296
Arg Glu Ile Leu Cys Gly Phe Ser Ser Leu Lys Asn Ser Lys Gly Asp
```

```
                    420                425                430
gat gct ctc cgt ttg tgc ttc cag atg tat gac aca gat aga tca ggg    1344
Asp Ala Leu Arg Leu Cys Phe Gln Met Tyr Asp Thr Asp Arg Ser Gly
        435                440                445 tgc atc acc aag gaa gaa gta gca tcc atg ctc tgt gct ttg cca gag    1392
Cys Ile Thr Lys Glu Glu Val Ala Ser Met Leu Cys Ala Leu Pro Glu
    450                455                460 gaa tgt ctt cca gct gat atc act gaa cct ggg aaa ttg gat gag ata    1440
Glu Cys Leu Pro Ala Asp Ile Thr Glu Pro Gly Lys Leu Asp Glu Ile
465                470                475                480 ttt gac tta atg gat gcc aac agt gat gga aaa gtt aca ttt gaa gaa    1488
Phe Asp Leu Met Asp Ala Asn Ser Asp Gly Lys Val Thr Phe Glu Glu
                485                490                495 ttc aaa gct gct atg cag aga gat agc tct ctc caa gac atg ctc ctc    1536
Phe Lys Ala Ala Met Gln Arg Asp Ser Ser Leu Gln Asp Met Leu Leu
            500                505                510 tct tct ctt cgt cca tca tag                                         1557
Ser Ser Leu Arg Pro Ser
            515
```

<210> SEQ ID NO 21
<211> LENGTH: 518
<212> TYPE: PRT
<213> ORGANISM: Lotus japonicus

<400> SEQUENCE: 21

```
Met Gly Tyr Asp Gln Thr Arg Lys Leu Ser Asp Glu Tyr Glu Ile Ser
1               5                   10                  15

Glu Ile Leu Gly Arg Gly Gly Phe Ser Val Val Arg Lys Gly Thr Lys
            20                  25                  30

Lys Ser Gly Asn Glu Lys Thr Gln Val Ala Ile Lys Thr Leu Arg Arg
        35                  40                  45

Leu Gly Ser Ser Pro Ser Gly Thr Gly Gly Gln Lys Ser Thr Ala
    50                  55                  60

Thr Val Met Gly Phe Pro Ser Leu Arg Gln Val Ser Val Ser Asp Ala
65                  70                  75                  80

Leu Leu Thr Asn Glu Ile Leu Val Met Arg Arg Ile Val Glu Asn Val
                85                  90                  95

Ser Pro His Pro Asn Val Ile Asp Leu Tyr Asp Val Cys Glu Asp Ser
            100                 105                 110

Asn Gly Val His Leu Val Leu Glu Leu Cys Ser Gly Gly Glu Leu Phe
        115                 120                 125

Asp Arg Ile Val Ala Gln Asp Lys Tyr Ala Glu Thr Glu Ala Ala Ala
    130                 135                 140

Val Val Arg Gln Ile Ala Ala Gly Leu Glu Ala Val His Lys Ala Asp
145                 150                 155                 160

Ile Val His Arg Asp Leu Lys Pro Glu Asn Cys Leu Phe Leu Asp Ser
                165                 170                 175

Arg Lys Asp Ser Pro Leu Lys Ile Met Asp Phe Gly Leu Ser Ser Val
            180                 185                 190

Glu Glu Phe Thr Asp Pro Val Val Gly Leu Phe Gly Ser Ile Asp Tyr
        195                 200                 205

Val Ser Pro Glu Ala Leu Ser Gln Gly Lys Ile Thr Ala Lys Ser Asp
    210                 215                 220

Met Trp Ser Leu Gly Val Ile Leu Tyr Ile Leu Leu Ser Gly Tyr Pro
225                 230                 235                 240

Pro Phe Ile Ala Gln Asn Asn Arg Gln Lys Gln Gln Met Ile Ile Asn
```

```
                  245                 250                 255
Gly Asn Phe Ser Phe Tyr Glu Lys Thr Trp Lys Gly Ile Thr Gln Ser
            260                 265                 270
Ala Lys Gln Leu Ile Ser Ser Leu Leu Thr Val Asp Pro Ser Lys Arg
        275                 280                 285
Pro Ser Ala Gln Glu Leu Leu Ser His Pro Trp Val Arg Gly Asp Lys
    290                 295                 300
Ala Lys Asp Glu Gln Met Asp Pro Glu Ile Val Ser Arg Leu Gln Ser
305                 310                 315                 320
Phe Asn Ala Arg Arg Lys Leu Arg Ala Ala Ile Ala Ser Val Trp
                325                 330                 335
Ser Ser Thr Ile Phe Leu Arg Thr Lys Lys Leu Arg Ser Leu Val Gly
            340                 345                 350
Thr Tyr Asp Leu Lys Glu Glu Ile Glu Ser Leu Arg Ile His Phe
        355                 360                 365
Lys Lys Ile Cys Gly Asn Gly Asp Asn Ala Thr Leu Ser Glu Phe Val
    370                 375                 380
Glu Val Leu Lys Ala Met Lys Met Pro Ser Leu Ile Pro Leu Ala Pro
385                 390                 395                 400
Arg Ile Phe Asp Leu Phe Asp Asn Asn Arg Asp Gly Thr Ile Asp Met
                405                 410                 415
Arg Glu Ile Leu Cys Gly Phe Ser Ser Leu Lys Asn Ser Lys Gly Asp
            420                 425                 430
Asp Ala Leu Arg Leu Cys Phe Gln Met Tyr Asp Thr Asp Arg Ser Gly
        435                 440                 445
Cys Ile Thr Lys Glu Glu Val Ala Ser Met Leu Cys Ala Leu Pro Glu
    450                 455                 460
Glu Cys Leu Pro Ala Asp Ile Thr Glu Pro Gly Lys Leu Asp Glu Ile
465                 470                 475                 480
Phe Asp Leu Met Asp Ala Asn Ser Asp Gly Lys Val Thr Phe Glu Glu
                485                 490                 495
Phe Lys Ala Ala Met Gln Arg Asp Ser Ser Leu Gln Asp Met Leu Leu
            500                 505                 510
Ser Ser Leu Arg Pro Ser
        515

<210> SEQ ID NO 22
<211> LENGTH: 30
<212> TYPE: DNA
<213> ORGANISM: Lotus japonicus
<220> FEATURE:
<221> NAME/KEY: misc_feature
<223> OTHER INFORMATION: primer

<400> SEQUENCE: 22
ggttgtttgg atccattgat tatgtttcac                              30

<210> SEQ ID NO 23
<211> LENGTH: 24
<212> TYPE: DNA
<213> ORGANISM: Lotus japonicus
<220> FEATURE:
<221> NAME/KEY: misc_feature
<223> OTHER INFORMATION: primer

<400> SEQUENCE: 23
catgggtacc cgatccgatt tgac                                    24
```

-continued

```
<210> SEQ ID NO 24
<211> LENGTH: 23
<212> TYPE: DNA
<213> ORGANISM: Lotus japonicus
<220> FEATURE:
<221> NAME/KEY: misc_feature
<223> OTHER INFORMATION: primer

<400> SEQUENCE: 24
gcgacccttc atatattgtg tct                                           23

<210> SEQ ID NO 25
<211> LENGTH: 28
<212> TYPE: DNA
<213> ORGANISM: Lotus japonicus
<220> FEATURE:
<221> NAME/KEY: misc_feature
<223> OTHER INFORMATION: primer

<400> SEQUENCE: 25
gtgttcatgg atatgtttga gtaaatag                                      28

<210> SEQ ID NO 26
<211> LENGTH: 518
<212> TYPE: PRT
<213> ORGANISM: Lotus japonicus
<220> FEATURE:
<221> NAME/KEY: MISC_FEATURE
<222> LOCATION: (265)..(265)
<223> OTHER INFORMATION: Xaa can be any naturally occurring amino acid
      excluding Thr or Ser

<400> SEQUENCE: 26
```

Met Gly Tyr Asp Gln Thr Arg Lys Leu Ser Asp Glu Tyr Glu Ile Ser
1               5                   10                  15

Glu Ile Leu Gly Arg Gly Gly Phe Ser Val Val Arg Lys Gly Thr Lys
            20                  25                  30

Lys Ser Gly Asn Glu Lys Thr Gln Val Ala Ile Lys Thr Leu Arg Arg
        35                  40                  45

Leu Gly Ser Ser Pro Ser Gly Thr Gly Gly Gln Lys Ser Thr Ala
    50                  55                  60

Thr Val Met Gly Phe Pro Ser Leu Arg Gln Val Ser Val Ser Asp Ala
65                  70                  75                  80

Leu Leu Thr Asn Glu Ile Leu Val Met Arg Arg Ile Val Glu Asn Val
                85                  90                  95

Ser Pro His Pro Asn Val Ile Asp Leu Tyr Asp Val Cys Glu Asp Ser
            100                 105                 110

Asn Gly Val His Leu Val Leu Glu Leu Cys Ser Gly Gly Glu Leu Phe
        115                 120                 125

Asp Arg Ile Val Ala Gln Asp Lys Tyr Ala Glu Thr Glu Ala Ala Ala
    130                 135                 140

Val Val Arg Gln Ile Ala Ala Gly Leu Glu Ala Val His Lys Ala Asp
145                 150                 155                 160

Ile Val His Arg Asp Leu Lys Pro Glu Asn Cys Leu Phe Leu Asp Ser
                165                 170                 175

Arg Lys Asp Ser Pro Leu Lys Ile Met Asp Phe Gly Leu Ser Ser Val
            180                 185                 190

Glu Glu Phe Thr Asp Pro Val Val Gly Leu Phe Gly Ser Ile Asp Tyr
        195                 200                 205

Val Ser Pro Glu Ala Leu Ser Gln Gly Lys Ile Thr Ala Lys Ser Asp
    210                 215                 220

Met Trp Ser Leu Gly Val Ile Leu Tyr Ile Leu Ser Gly Tyr Pro
225                 230                 235                 240

Pro Phe Ile Ala Gln Asn Asn Arg Gln Lys Gln Met Ile Ile Asn
            245                 250                 255

Gly Asn Phe Ser Phe Tyr Glu Lys Xaa Trp Lys Gly Ile Thr Gln Ser
        260                 265                 270

Ala Lys Gln Leu Ile Ser Ser Leu Leu Thr Val Asp Pro Ser Lys Arg
    275                 280                 285

Pro Ser Ala Gln Glu Leu Leu Ser His Pro Trp Val Arg Gly Asp Lys
290                 295                 300

Ala Lys Asp Glu Gln Met Asp Pro Glu Ile Val Ser Arg Leu Gln Ser
305                 310                 315                 320

Phe Asn Ala Arg Arg Lys Leu Arg Ala Ala Ile Ala Ser Val Trp
                325                 330                 335

Ser Ser Thr Ile Phe Leu Arg Thr Lys Lys Leu Arg Ser Leu Val Gly
            340                 345                 350

Thr Tyr Asp Leu Lys Glu Glu Ile Glu Ser Leu Arg Ile His Phe
                355                 360                 365

Lys Lys Ile Cys Gly Asn Gly Asp Asn Ala Thr Leu Ser Glu Phe Val
    370                 375                 380

Glu Val Leu Lys Ala Met Lys Met Pro Ser Leu Ile Pro Leu Ala Pro
385                 390                 395                 400

Arg Ile Phe Asp Leu Phe Asp Asn Asn Arg Asp Gly Thr Ile Asp Met
                405                 410                 415

Arg Glu Ile Leu Cys Gly Phe Ser Ser Leu Lys Asn Ser Lys Gly Asp
            420                 425                 430

Asp Ala Leu Arg Leu Cys Phe Gln Met Tyr Asp Thr Asp Arg Ser Gly
        435                 440                 445

Cys Ile Thr Lys Glu Glu Val Ala Ser Met Leu Cys Ala Leu Pro Glu
    450                 455                 460

Glu Cys Leu Pro Ala Asp Ile Thr Glu Pro Gly Lys Leu Asp Glu Ile
465                 470                 475                 480

Phe Asp Leu Met Asp Ala Asn Ser Asp Gly Lys Val Thr Phe Glu Glu
                485                 490                 495

Phe Lys Ala Ala Met Gln Arg Asp Ser Ser Leu Gln Asp Met Leu Leu
            500                 505                 510

Ser Ser Leu Arg Pro Ser
        515

<210> SEQ ID NO 27
<211> LENGTH: 516
<212> TYPE: PRT
<213> ORGANISM: Oryza sativa
<220> FEATURE:
<221> NAME/KEY: MISC_FEATURE
<222> LOCATION: (263)..(263)
<223> OTHER INFORMATION: Xaa can be any naturally occurring amino acid
      excluding Thr or Ser

<400> SEQUENCE: 27

Met Ser Lys Thr Glu Ser Arg Lys Leu Ser Asp Asp Tyr Glu Val Val
1               5                   10                  15

Asp Val Leu Gly Arg Gly Gly Phe Ser Ile Val Arg Gly Val Ser
            20                  25                  30

Lys Ser Glu Glu Lys Thr Gln Val Ala Ile Lys Thr Leu Arg Arg Leu
        35                  40                  45

Gly Pro Ala Met Ala Gly Met Lys Gln Gly Thr Lys Pro Val Pro Gly

-continued

```
                50                  55                  60
Ser Gly Leu Pro Met Trp Lys Gln Val Ser Ile Ser Asp Ala Leu Leu
 65                  70                  75                  80

Thr Asn Glu Ile Leu Val Met Arg Arg Ile Val Glu Ser Val Ala Pro
                 85                  90                  95

His Pro Asn Val Ile Asn Leu His Asp Val Tyr Glu Asp Val His Gly
                100                 105                 110

Val His Leu Val Leu Glu Leu Cys Ser Gly Gly Glu Leu Phe Asp Arg
            115                 120                 125

Ile Val Gly Arg Asp Arg Tyr Ser Glu Phe Asp Ala Ala Cys Val Ile
        130                 135                 140

Arg Gln Ile Ala Ser Gly Leu Glu Ala Leu His Lys Ala Ser Ile Val
145                 150                 155                 160

His Arg Asp Leu Lys Pro Glu Asn Cys Leu Phe Ser Asp Lys Asp Glu
                165                 170                 175

Lys Ser Thr Leu Lys Ile Met Asp Phe Gly Leu Ser Ser Val Glu Asp
                180                 185                 190

Phe Ser Asp Pro Ile Val Ala Leu Phe Gly Ser Ile Asp Tyr Val Ser
            195                 200                 205

Pro Glu Ala Leu Ser Arg Gln Glu Val Ser Ala Ala Ser Asp Met Trp
        210                 215                 220

Ser Val Gly Val Ile Leu Tyr Ile Leu Leu Ser Gly Cys Pro Pro Phe
225                 230                 235                 240

His Ala Ala Thr Asn Arg Glu Lys Gln Gln Arg Ile Leu Gln Gly Glu
                245                 250                 255

Phe Ser Phe Gln Asp His Xaa Trp Lys Thr Ile Ser Ser Ser Ala Lys
                260                 265                 270

Asp Leu Ile Ser Arg Leu Leu Ser Val Gln Pro Tyr Lys Arg Pro Thr
            275                 280                 285

Ala Ser Asp Leu Leu Arg His Pro Trp Val Ile Gly Asp Cys Ala Lys
        290                 295                 300

Gln Asp Leu Met Asp Ala Glu Val Val Ser Lys Leu Gln Lys Phe Asn
305                 310                 315                 320

Ala Arg Arg Lys Leu Arg Ala Ala Ile Ala Ser Val Leu Ser Cys
                325                 330                 335

Lys Val Ala Leu Arg Thr Lys Arg Leu Arg Asn Leu Leu Gly Thr His
            340                 345                 350

Asp Leu Thr Ser Glu Glu Leu Asp Asn Leu Arg Leu His Phe Gly Arg
        355                 360                 365

Ile Cys Ala Asp Gly Glu Asn Ala Thr Leu Ser Glu Phe Glu Gln Val
    370                 375                 380

Leu Arg Ala Met Lys Met Asp Ser Leu Ile Pro Leu Ala Pro Arg Val
385                 390                 395                 400

Phe Asp Leu Phe Asp Asn Asn Arg Asp Gly Thr Val Asp Met Arg Glu
                405                 410                 415

Ile Leu Cys Gly Phe Ser Ser Leu Arg Asn Ser Arg Gly Asp Asp Ala
            420                 425                 430

Leu Arg Leu Cys Phe Gln Met Tyr Asp Ala Asp Arg Ser Gly Cys Ile
        435                 440                 445

Ser Lys Glu Glu Leu Ala Ser Met Leu Arg Ala Leu Pro Glu Glu Cys
    450                 455                 460

Leu Pro Gly Asp Ile Thr Glu Pro Gly Lys Leu Asp Glu Val Phe Asp
465                 470                 475                 480
```

-continued

```
Gln Met Asp Ala Asp Ser Asp Gly Lys Val Thr Phe Asp Glu Phe Lys
            485                 490                 495

Ala Ala Met Asn Lys Asp Ser Ala Leu Gln Asp Val Leu Leu Ser Ser
            500                 505                 510

Leu Arg Pro Gln
        515
```